(12) United States Patent
Cha et al.

(10) Patent No.: US 11,926,607 B2
(45) Date of Patent: Mar. 12, 2024

(54) COMPOUND AND ORGANIC LIGHT EMITTING DEVICE COMPRISING THE SAME

(71) Applicant: LG CHEM, LTD., Seoul (KR)

(72) Inventors: Yongbum Cha, Daejeon (KR); Jaegoo Lee, Daejeon (KR); Sung Kil Hong, Daejeon (KR); Sung Jae Lee, Daejeon (KR); Hyeon Jin Mun, Daejeon (KR)

(73) Assignee: LG Chem, Ltd., Seoul (KR)

( * ) Notice: Subject to any disclaimer, the term of this patent is extended or adjusted under 35 U.S.C. 154(b) by 662 days.

(21) Appl. No.: 16/981,129

(22) PCT Filed: Jul. 3, 2019

(86) PCT No.: PCT/KR2019/008169
§ 371 (c)(1),
(2) Date: Sep. 15, 2020

(87) PCT Pub. No.: WO2020/036314
PCT Pub. Date: Feb. 20, 2020

(65) Prior Publication Data
US 2021/0053934 A1 Feb. 25, 2021

(30) Foreign Application Priority Data

Aug. 17, 2018 (KR) .................. 10-2018-0096137
Jun. 20, 2019 (KR) .................. 10-2019-0073543

(51) Int. Cl.
*C07D 311/82* (2006.01)
*C07D 405/10* (2006.01)
(Continued)

(52) U.S. Cl.
CPC .......... *C07D 311/82* (2013.01); *C07D 405/10* (2013.01); *C07D 491/048* (2013.01);
(Continued)

(58) Field of Classification Search
None
See application file for complete search history.

(56) References Cited

U.S. PATENT DOCUMENTS

2004/0251816 A1 12/2004 Lee et al.
2014/0299192 A1 10/2014 Lee et al.
(Continued)

FOREIGN PATENT DOCUMENTS

CN 104193736 A 12/2014
CN 106478611 A 3/2017
(Continued)

OTHER PUBLICATIONS

Machine English translation of Jeong et al. (KR 10-2016-0047670). Aug. 4, 2023.*
(Continued)

*Primary Examiner* — Jay Yang
(74) *Attorney, Agent, or Firm* — Bryan Cave Leighton Paisner LLP

(57) ABSTRACT

The present disclosure provides a compound represented by the following Chemical Formula 1, and an organic light emitting device including the same. The compound is used as a material of an organic material layer of the organic light emitting device.

[Chemical Formula 1]

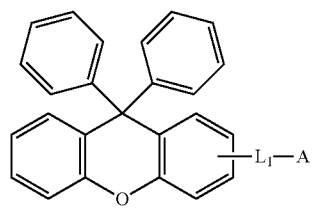

7 Claims, 1 Drawing Sheet

(51) Int. Cl.
*C07D 491/048* (2006.01)
*C07D 495/04* (2006.01)
*H01L 51/00* (2006.01)
*H10K 85/60* (2023.01)

(52) U.S. Cl.
CPC ......... *C07D 495/04* (2013.01); *H10K 85/654* (2023.02); *H10K 85/6574* (2023.02); *H10K 85/6576* (2023.02)

(56) References Cited

U.S. PATENT DOCUMENTS

| | | | |
|---|---|---|---|
| 2015/0162542 A1 | 1/2015 | Ryu et al. |
| 2015/0162543 A1 | 1/2015 | Lee et al. |
| 2015/0295181 A1 | 10/2015 | Mujiea-Fernaud et al. |
| 2016/0118599 A1 | 4/2016 | Jeong et al. |
| 2016/0218298 A1 | 7/2016 | Lee et al. |
| 2017/0054094 A1 | 2/2017 | Cheng et al. |
| 2017/0222157 A1 | 8/2017 | Jatsch et al. |
| 2018/0013074 A1 | 1/2018 | Zeng et al. |
| 2018/0159050 A1 | 6/2018 | Kim et al. |
| 2019/0189929 A1 | 6/2019 | Heo et al. |

FOREIGN PATENT DOCUMENTS

| | | |
|---|---|---|
| CN | 106800558 A | 6/2017 |
| CN | 107778219 A | 3/2018 |
| JP | H08259937 A | 10/1996 |
| JP | H10338871 A | 12/1998 |
| KR | 10-2000-0051826 A | 8/2000 |
| KR | 10-2014-0025120 A | 3/2014 |
| KR | 10-1380060 B1 | 4/2014 |
| KR | 10-2015-0034004 A | 4/2015 |
| KR | 10-2015-0106501 A | 9/2015 |
| KR | 10-2016-0047670 A | 5/2016 |
| KR | 10-2017-0032414 A | 3/2017 |
| KR | 10-2017-0121691 A | 11/2017 |
| KR | 10-2017-0135669 A | 12/2017 |
| KR | 10-2018-0066339 A | 6/2018 |
| KR | 10-2018-0076357 A | 7/2018 |
| WO | 2003-012890 A1 | 2/2003 |
| WO | 2014-030822 A1 | 2/2014 |
| WO | 2014-072017 A1 | 5/2014 |
| WO | 2018-030786 A1 | 2/2018 |

OTHER PUBLICATIONS

K. Gao, et al., "An "Ideal" Universal Host For Highly Efficient Full-Color, White Phosphorescent and Thermally Activated Delayed Fluorescent OLEDs With Extremely Simple and Unified Structure" Journal of Materials Chemistry C, 2017, 5(39), 10406-10416.

* cited by examiner

[FIG. 1]
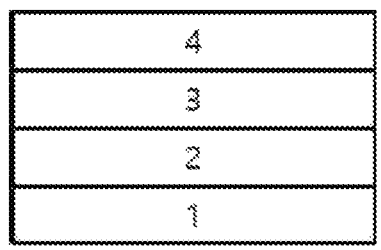
[FIG. 2]
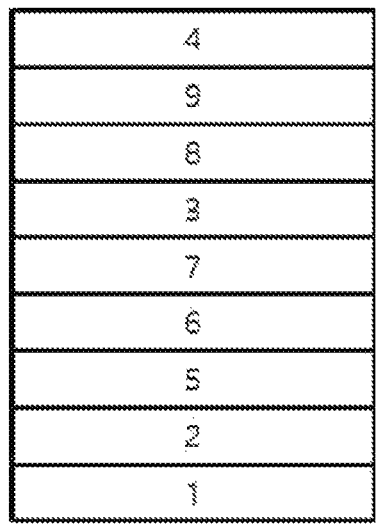

COMPOUND AND ORGANIC LIGHT EMITTING DEVICE COMPRISING THE SAME

CROSS-REFERENCE TO RELATED APPLICATION(S)

This application claims the benefits of the filing dates of Korean Patent Application No. 10-2018-0096137 filed with Korean Intellectual Property Office on Aug. 17, 2018, and Korean Patent Application No. 10-2019-0073543 filed with Korean Intellectual Property Office on Jun. 20, 2019, the entire contents of which are incorporated herein by reference.

TECHNICAL FIELD

The present invention relates to a novel compound and to an organic light emitting device including the same.

BACKGROUND ART

In general, an organic light emitting phenomenon refers to a phenomenon where electric energy is converted into light energy by using an organic material. The organic light emitting device using the organic light emitting phenomenon has characteristics such as a wide viewing angle, excellent contrast, a fast response time, and excellent luminance, driving voltage, and response speed, and thus many studies have proceeded thereon.

The organic light emitting device generally has a structure which includes an anode, a cathode, and an organic material layer interposed between the anode and the cathode. The organic material layer frequently has a multilayered structure that includes different materials in order to enhance efficiency and stability of the organic light emitting device, and for example, the organic material layer may be formed of a hole injection layer, a hole transport layer, a light emitting layer, an electron transport layer, an electron injection layer, and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in these organic light emitting devices.

PRIOR ART LITERATURE

Patent Literature (Patent Literature 1) Korean Patent Laid-open Publication No. 10-2000-0051826

DETAILED DESCRIPTION OF THE INVENTION

Technical Problem

An object of the present disclosure is to provide a novel organic light emitting material and an organic light emitting device including the same.

Technical Solution

In one aspect of the invention, a compound represented by the following Chemical Formula 1 is provided:

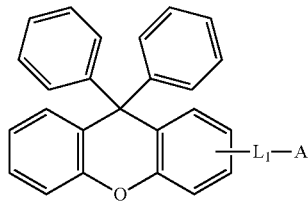

[Chemical Formula 1]

wherein in Chemical Formula 1,
$L_1$ is a single bond, or a substituted or unsubstituted $C_{6-60}$ arylene, and
A is any one selected from the following groups,

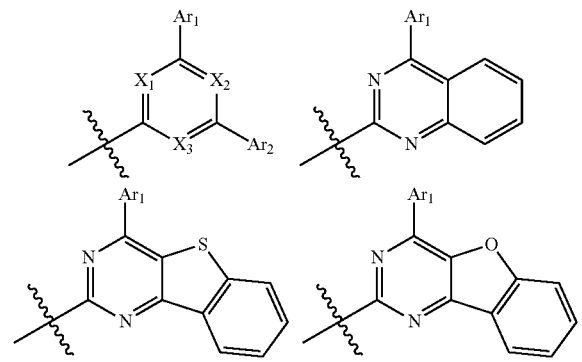

wherein $X_1$, $X_2$, and $X_3$ are each independently CH or N, provided that at least one of $X_1$, $X_2$, and $X_3$ is N, and
$Ar_1$ and $Ar_2$ are each independently a substituted or unsubstituted $C_{6-60}$ aryl, or a substituted or unsubstituted $C_{2-60}$ heteroaryl containing at least one of O and S.

In another aspect of the invention, an organic light emitting device is provided, the organic light emitting device includes: a first electrode; a second electrode provided to face the first electrode; and one or more organic material layers provided between the first electrode and the second electrode, wherein one or more layers of the organic material layers include the compound represented by Chemical Formula 1.

Advantageous Effects

The compound represented by Chemical Formula 1 described above can be used as a material of an organic material layer of an organic light emitting device, and may improve the efficiency, achieve a low driving voltage and/or improve lifetime characteristics of the organic light emitting device. In particular, the compound represented by Chemical Formula 1 described above can be used as a material for hole injection, hole transport, hole blocking and transport, light emitting, electron transport, or electron injection.

BRIEF DESCRIPTION OF DRAWINGS

FIG. 1 shows an example of an organic light emitting device including a substrate 1, an anode 2, a light emitting layer 3, and a cathode 4.

FIG. 2 shows an example of an organic light emitting device including a substrate 1, an anode 2, a hole injection layer 5, a hole transport layer 6, an electron blocking layer 7, a light emitting layer 3, a hole blocking layer 8, an electron transport layer 9, and a cathode 4.

DETAILED DESCRIPTION OF THE EMBODIMENTS

Hereinafter, the present invention will be described in more detail to help understanding of the present invention.

In one embodiment of the invention, a compound represented by Chemical Formula 1 is provided.

As used herein, the notation

means a bond linked to another substituent group.

As used herein, the term "substituted or unsubstituted" means being unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a hetero-cyclic group containing at least one of N, O, and S atoms, or being unsubstituted or substituted with a substituent to which two or more substituents are linked among the substituents exemplified above. For example, "the substituent to which two or more substituents are linked" may be a biphenyl group. That is, the biphenyl group may also be an aryl group, and may be interpreted as a substituent to which two phenyl groups are linked.

In the present specification, the number of carbon atoms of a carbonyl group is not particularly limited, but is preferably 1 to 40. Specifically, the carbonyl group may be a compound having the following structural formulae, but is not limited thereto.

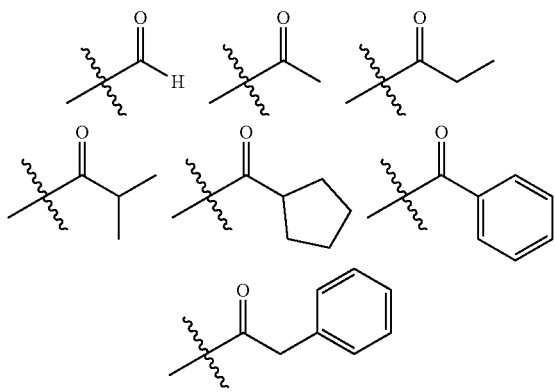

In the present specification, an ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be a compound having the following structural formulae, but is not limited thereto.

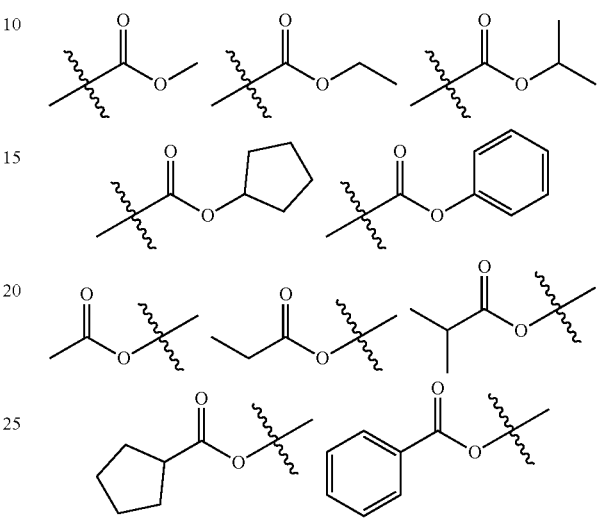

In the present specification, the number of carbon atoms of an imide group is not particularly limited, but is preferably 1 to 25. Specifically, the imide group may be a compound having the following structural formulae, but is not limited thereto.

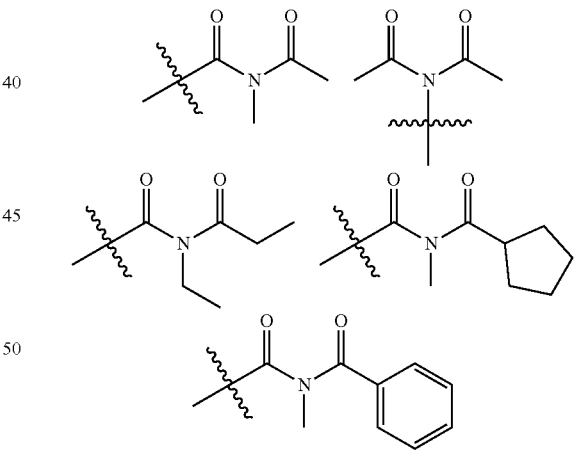

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, and iodine.

In the present specification, the alkyl group may be a straight chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentyl-methyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group may be a straight chain or branched chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group is not particularly limited, but preferably has 6 to 60 carbon atoms, and may be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group may be a phenyl group, a biphenyl group, a terphenyl group, or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, a fluorenyl group may be substituted, and two substituent groups may be bonded to each other to form a spiro structure. In the case where the fluorenyl group is substituted,

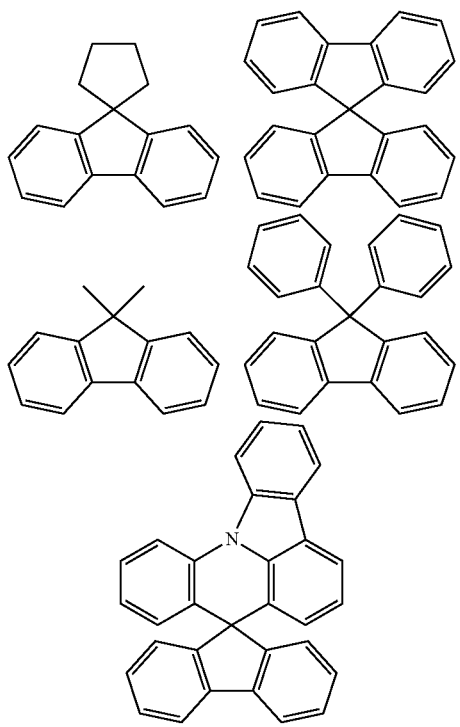

and the like can be formed. However, the structure is not limited thereto.

In the present specification, a heterocyclic group is one including one or more of O, N, Si, and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group, and the alkylamine group is the same as the aforementioned examples of the alkyl group. In the present specification, the heteroaryl in the heteroarylamine can be applied to the aforementioned description of the heterocyclic group. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but is formed by combining two substituent groups. In the present specification, the aforementioned description of the heterocyclic group can be applied, except that the heterocycle is not a monovalent group but is formed by combining two substituent groups.

Preferably, $L_1$ may be a single bond, or a substituted or unsubstituted $C_{6-20}$ arylene.

More preferably, $L_1$ may be a single bond, phenylene, biphenylylene, terphenylylene, quaterphenylylene, naphthylene, anthracenylene, fluorenylene, phenanthrenylene, pyrenylene, or triphenylenylene.

Most preferably, $L_1$ may be a single bond, phenylene, or biphenylylene.

Preferably, $Ar_1$ and $Ar_2$ may each independently be a substituted or unsubstituted $C_{6-20}$ aryl; or a substituted or unsubstituted $C_{6-20}$ heteroaryl containing at least one of O and S.

More preferably, the $Ar_1$ and $Ar_2$ may each independently be phenyl, biphenylyl, naphthyl, dibenzofuranyl, or dibenzothiophenyl.

Preferably, at least one of $Ar_1$ and $Ar_2$ may be a substituted or unsubstituted $C_{6-60}$ aryl.

More preferably, $Ar_1$ may be a substituted or unsubstituted $C_{6-60}$ aryl.

More preferably, $Ar_1$ may be a substituted or unsubstituted $C_{6-20}$ aryl.

Most preferably, $Ar_1$ may be phenyl, biphenylyl, or naphthyl.

The above-mentioned compound may be represented by any one of the following Chemical Formulas 1-1 to 1-3:

[Chemical Formula 1-1]

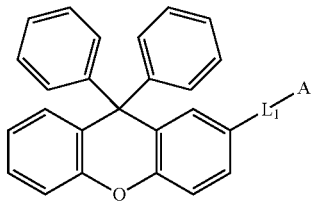

[Chemical Formula 1-2]

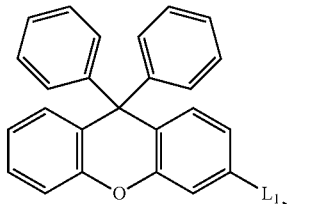

[Chemical Formula 1-3]

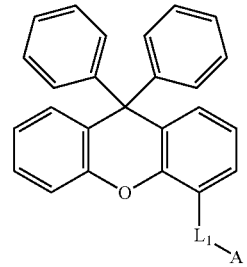

wherein in Chemical Formulas 1-1 to 1-3, $L_1$ and A are the same as defined above for Chemical Formula 1

Representative examples of the compound represented by Chemical Formula 1 are as follows:

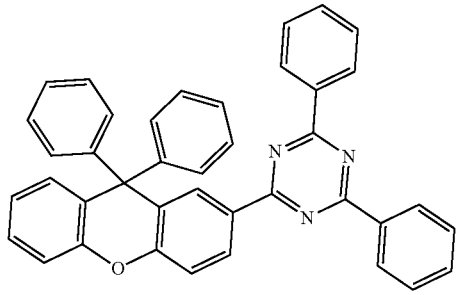

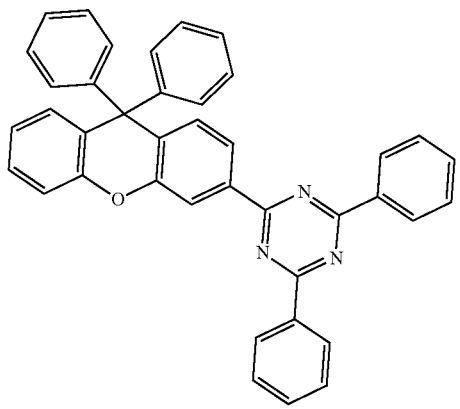

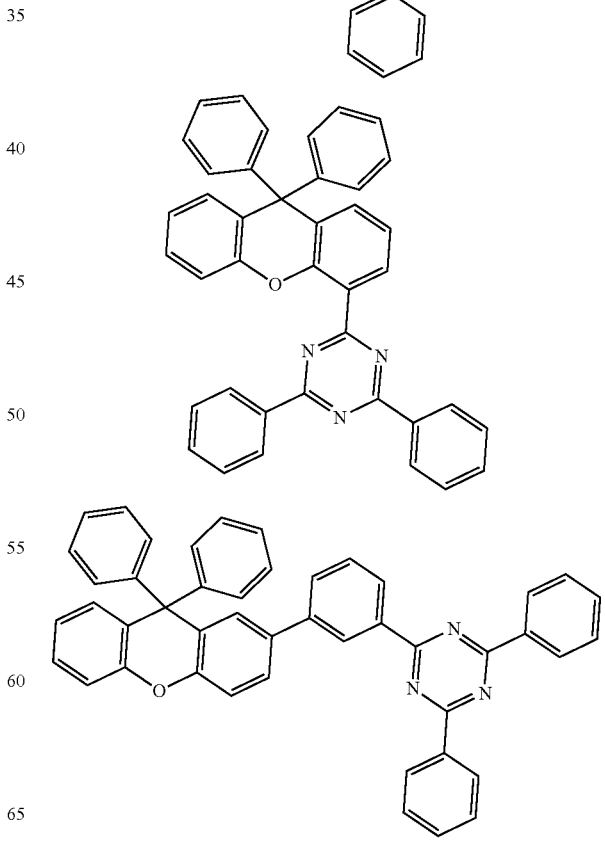

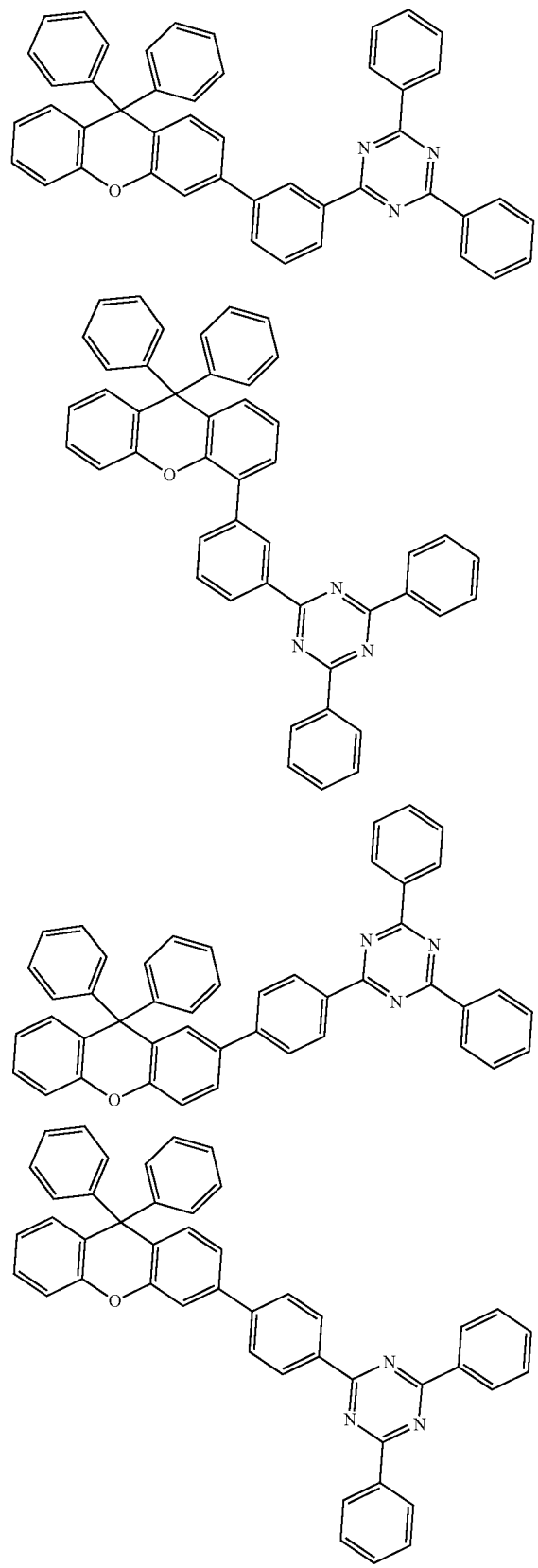
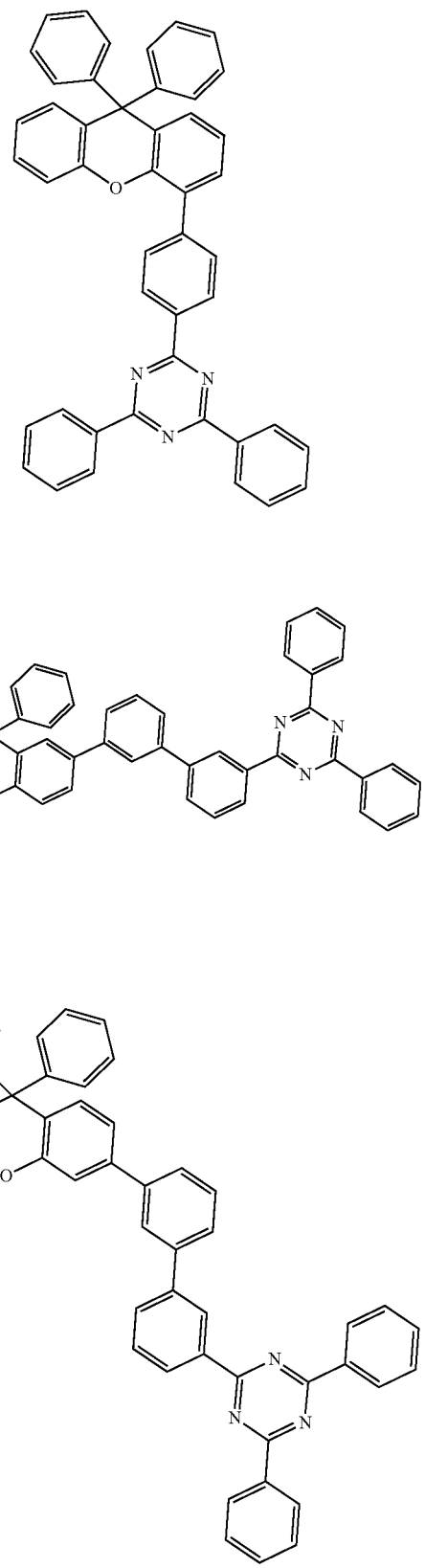

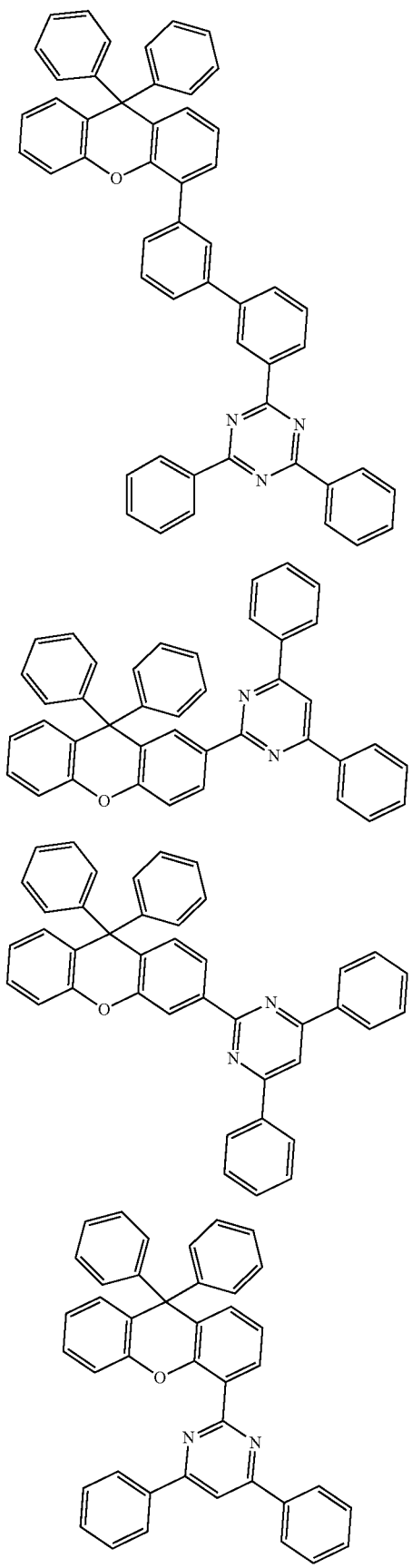
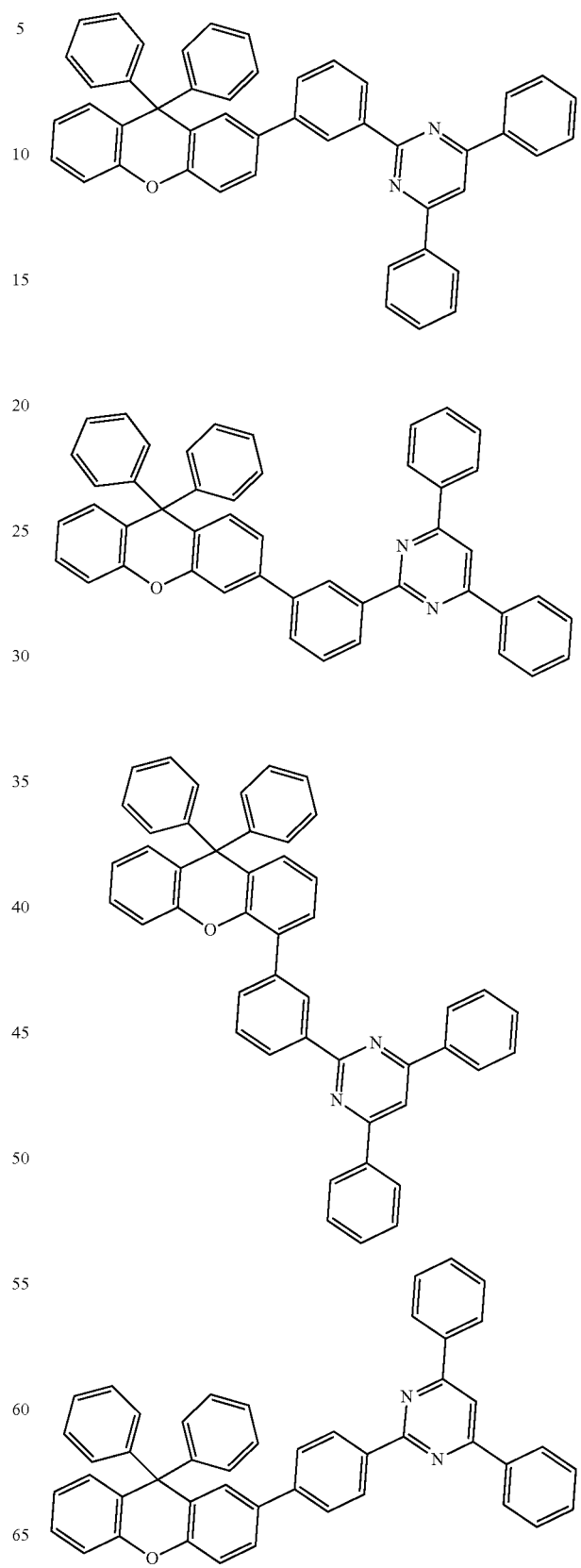

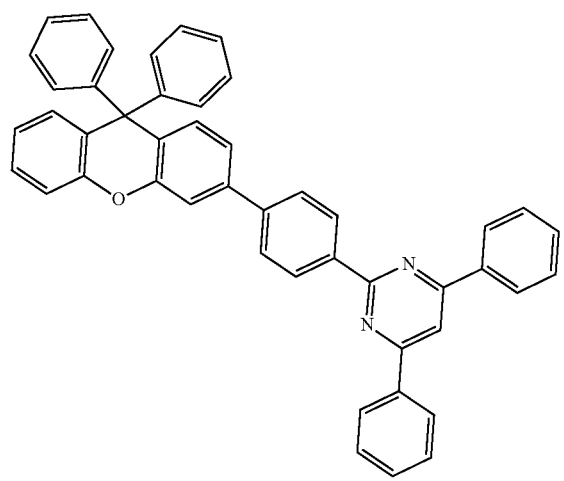
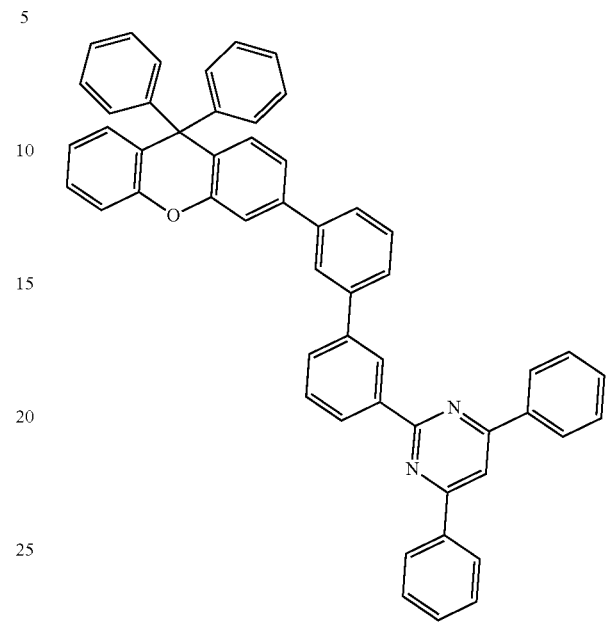
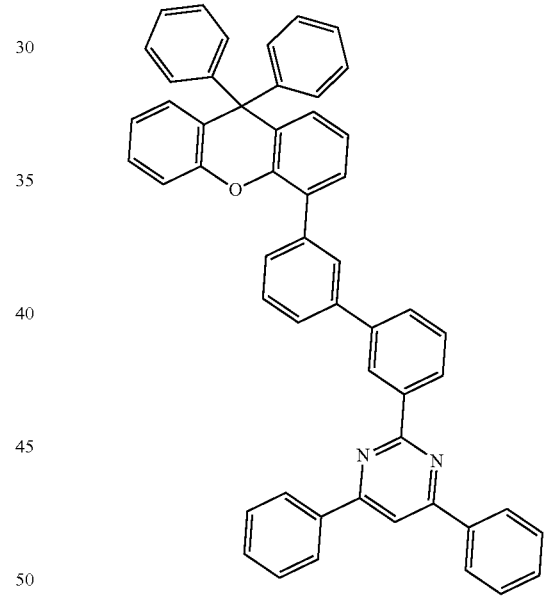
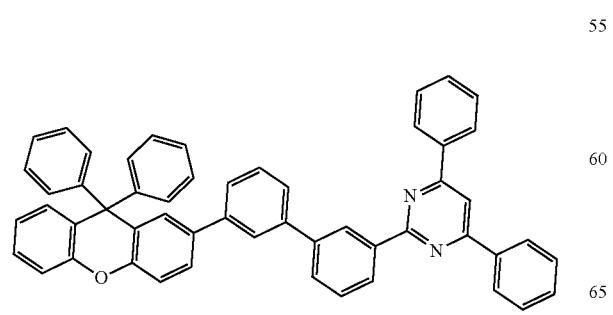
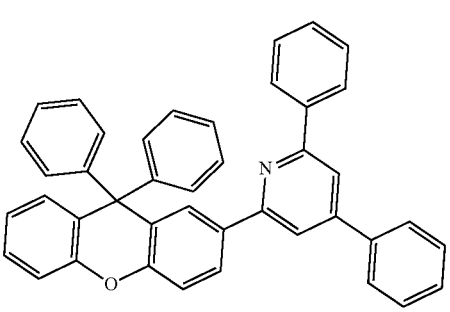

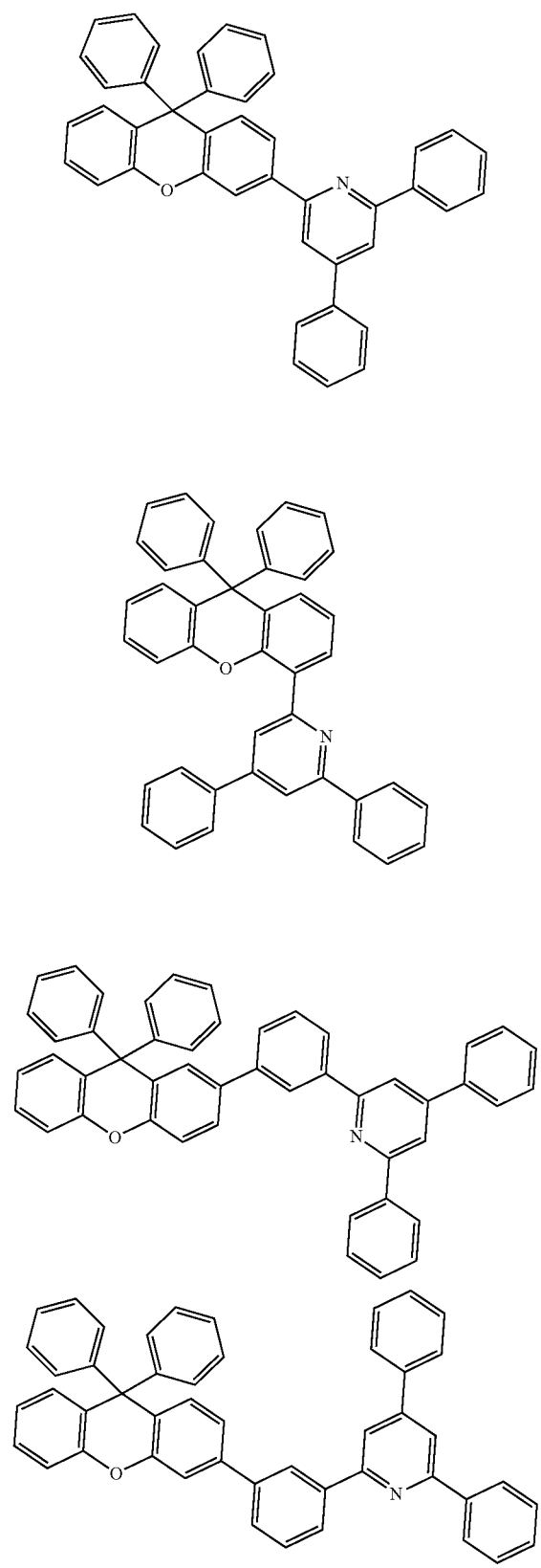
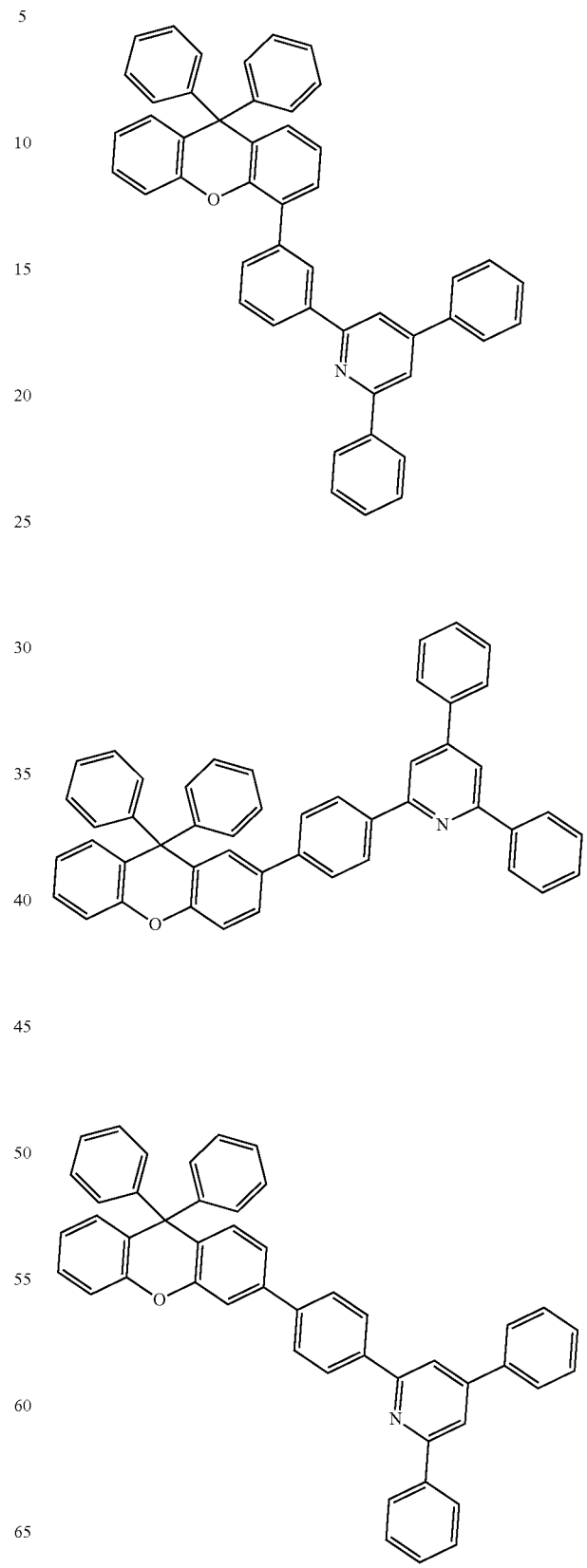

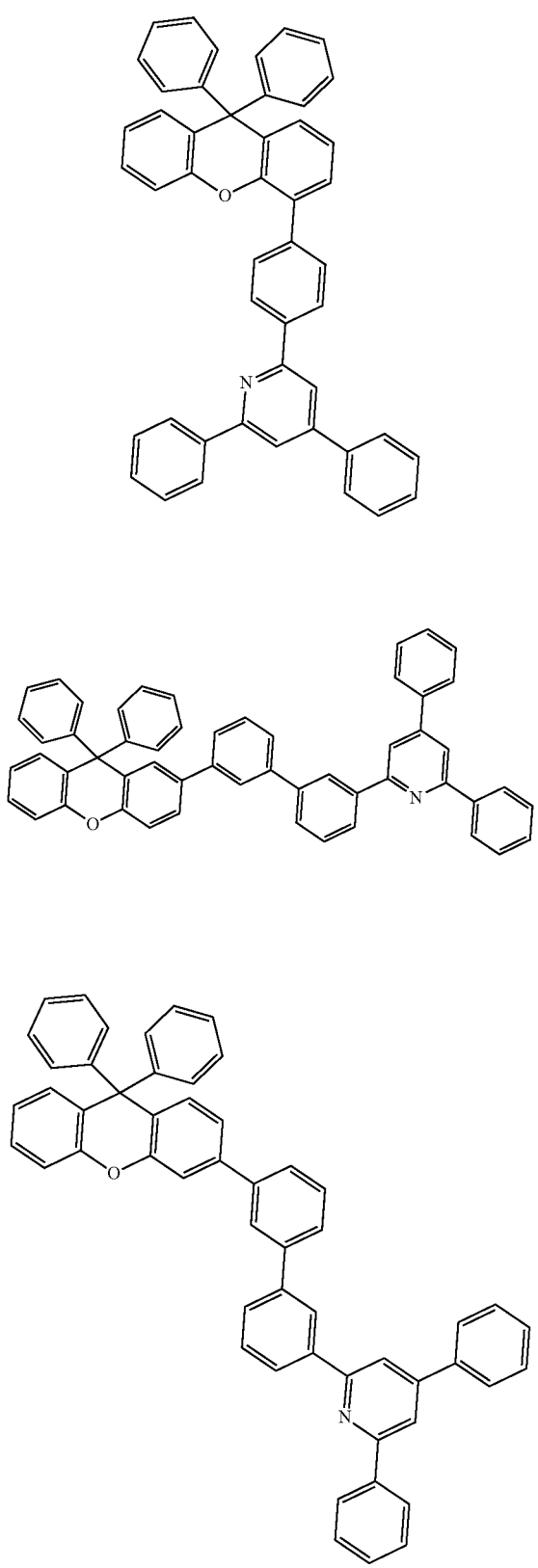
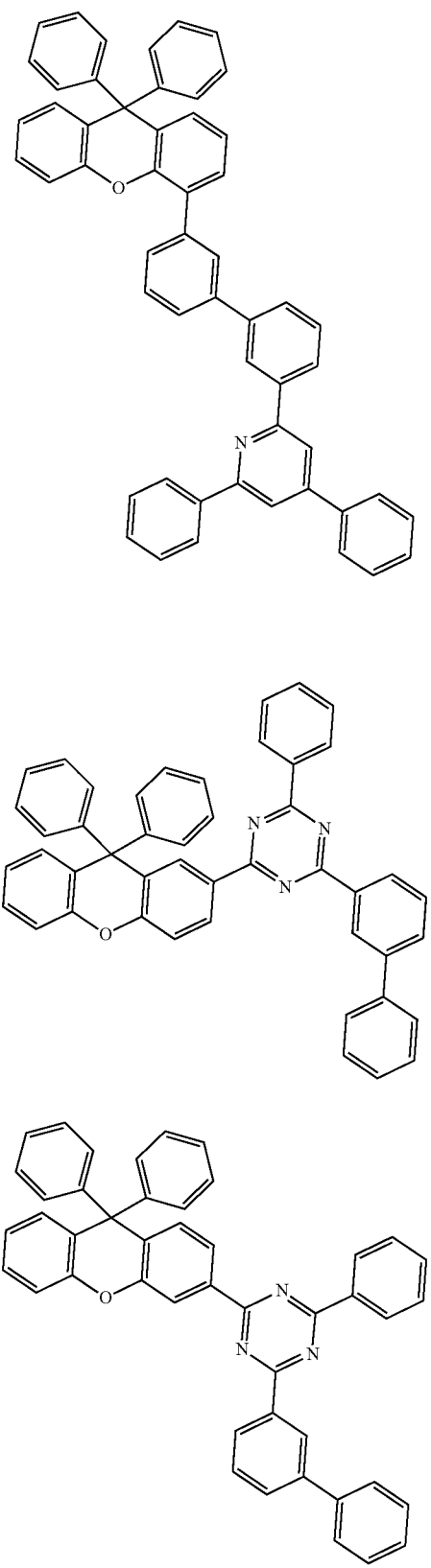

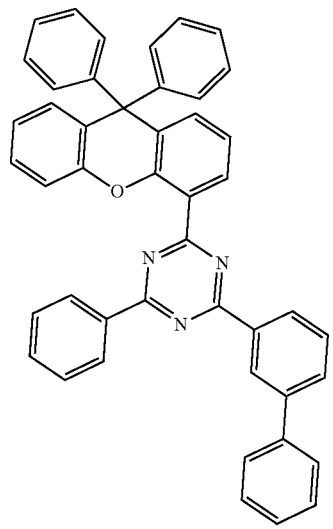
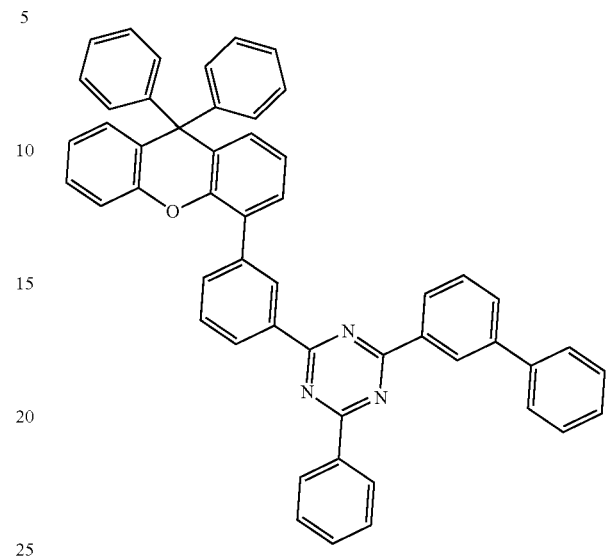
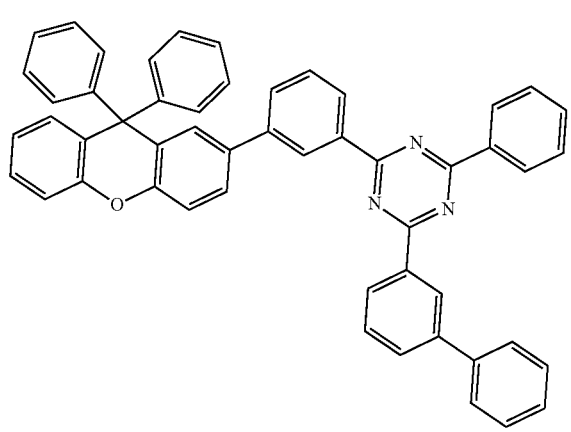
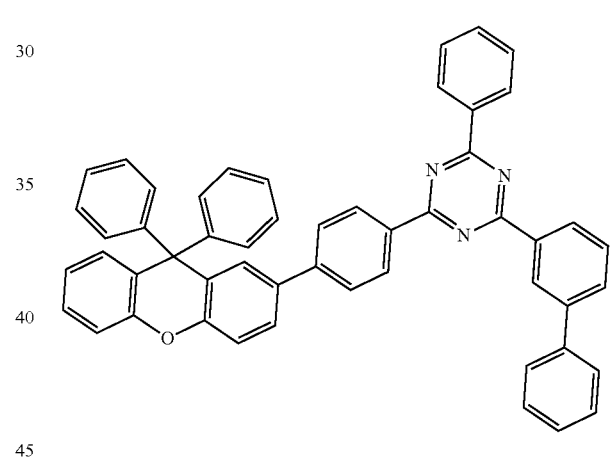
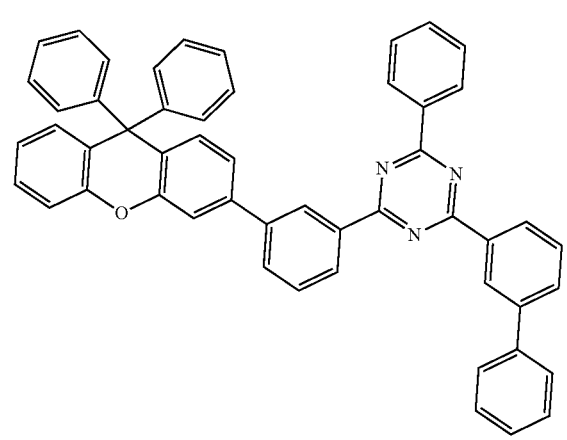
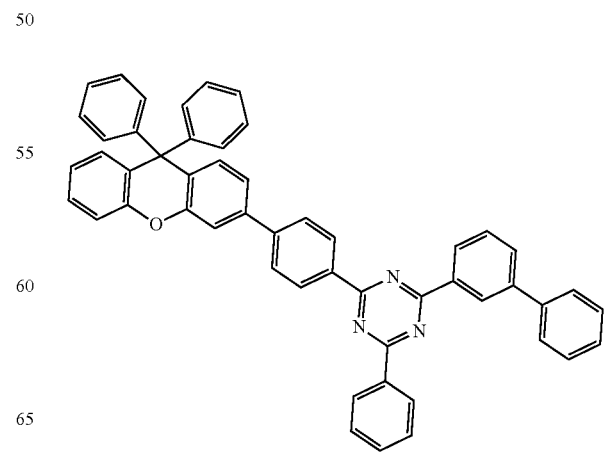

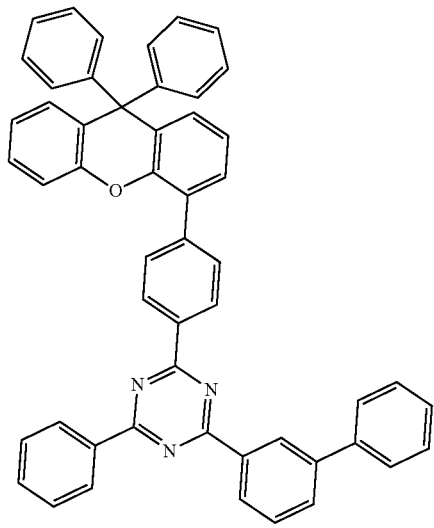
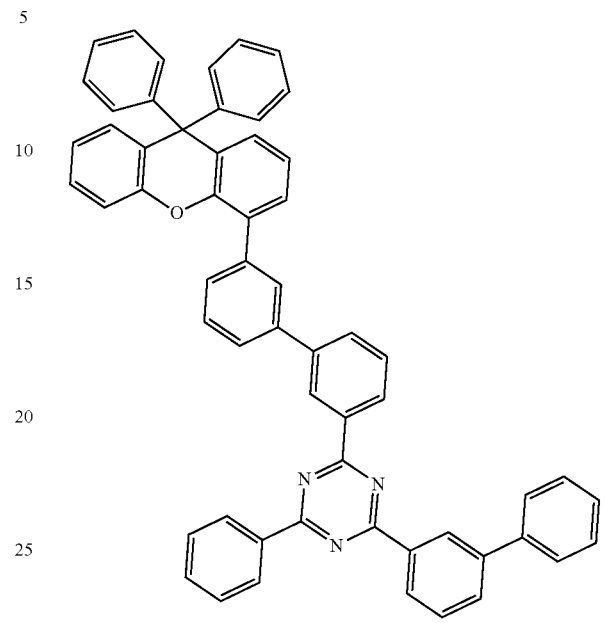
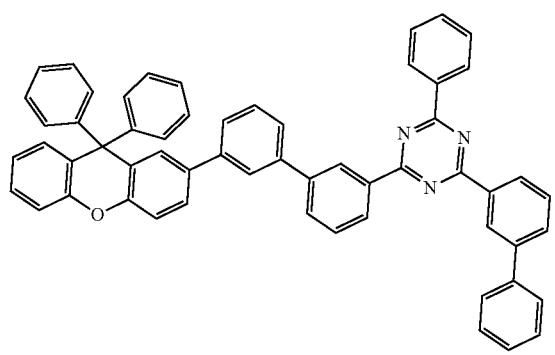
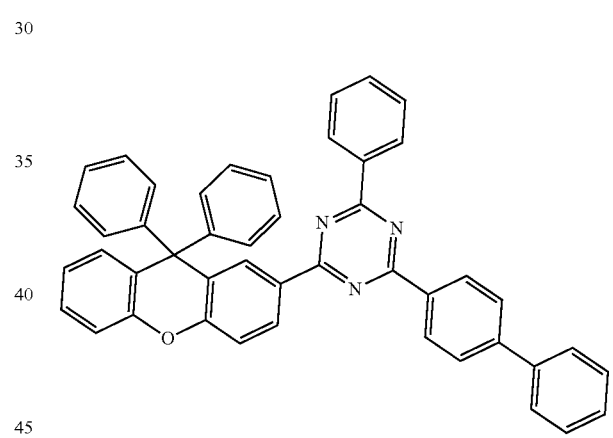
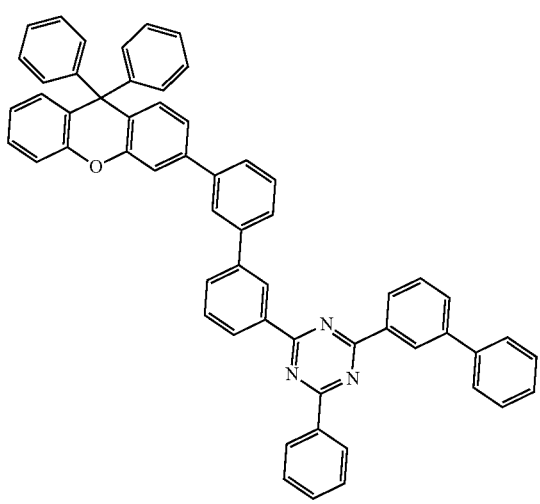
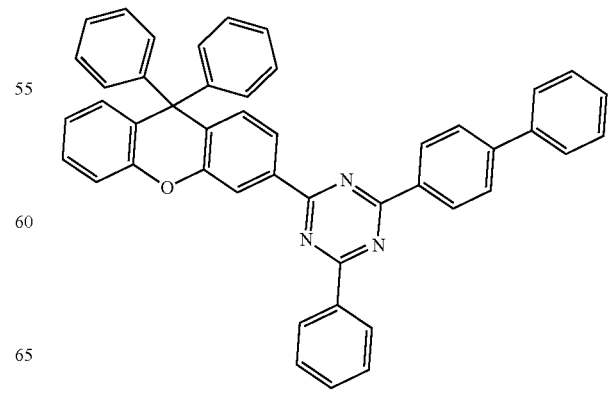

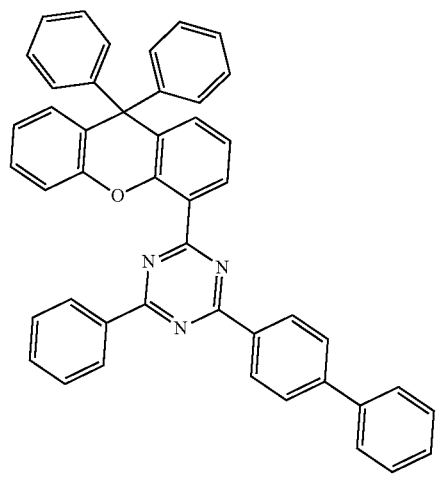
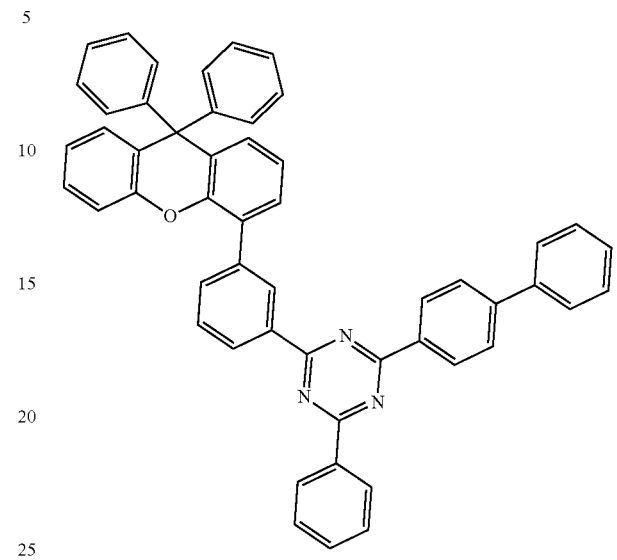
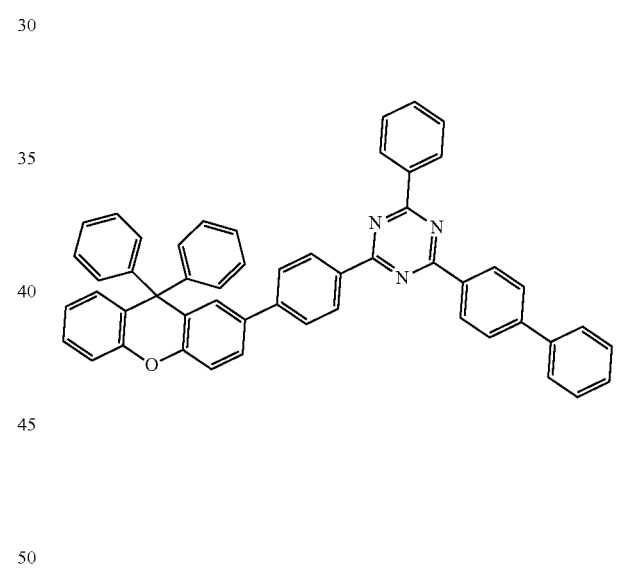
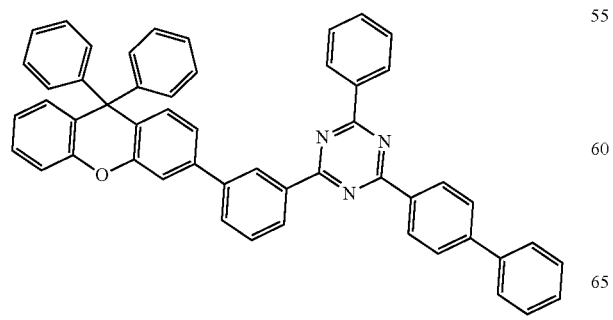
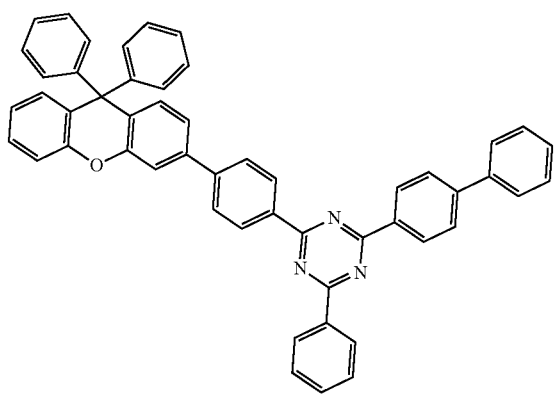

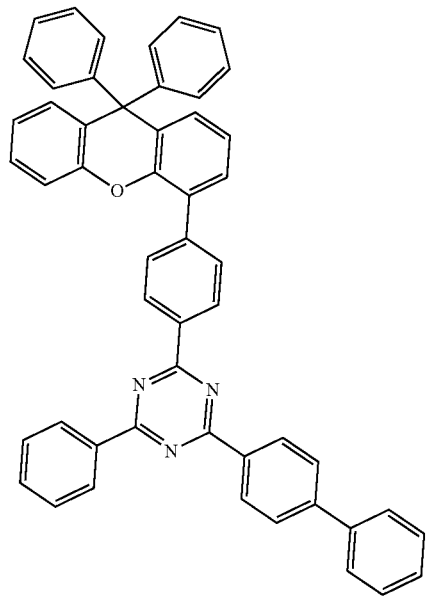
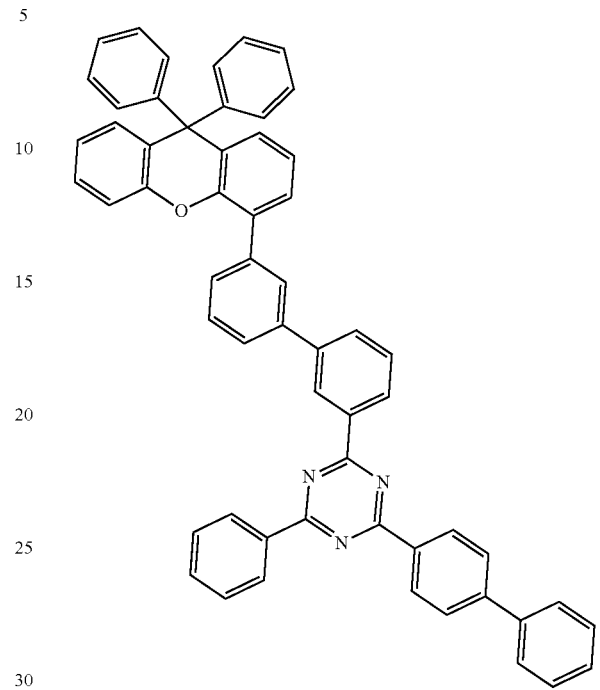
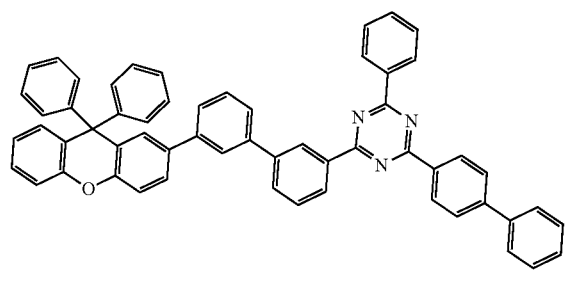
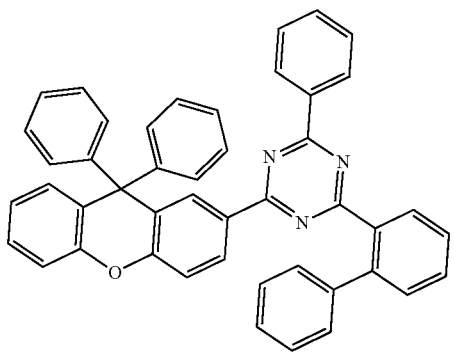
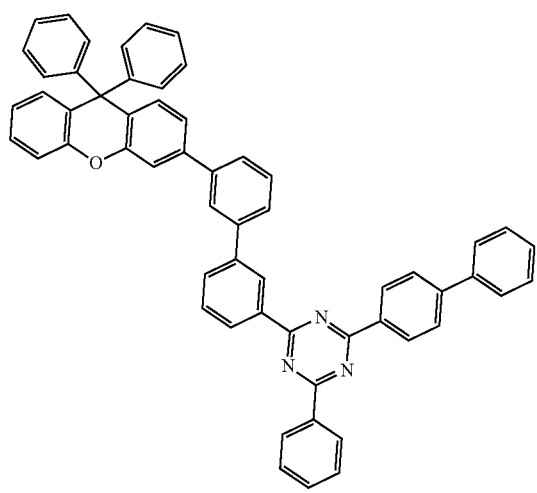
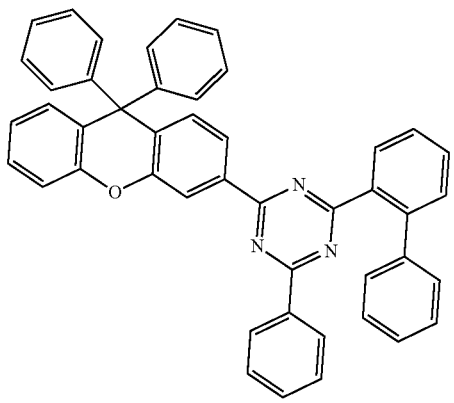

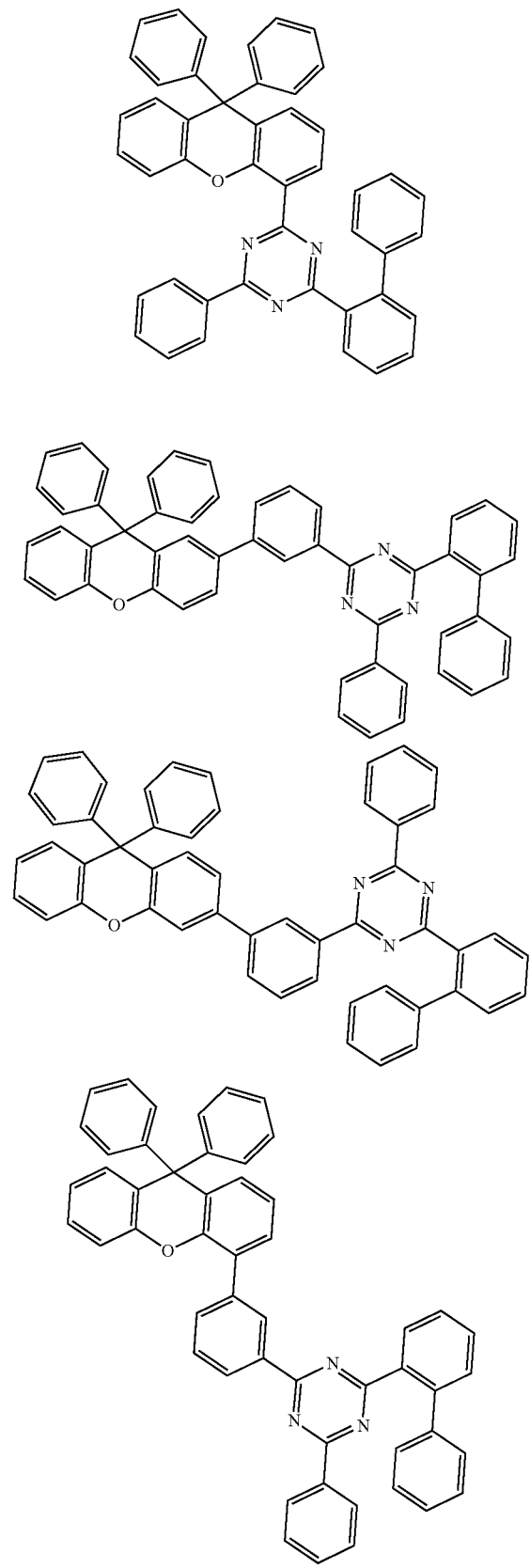
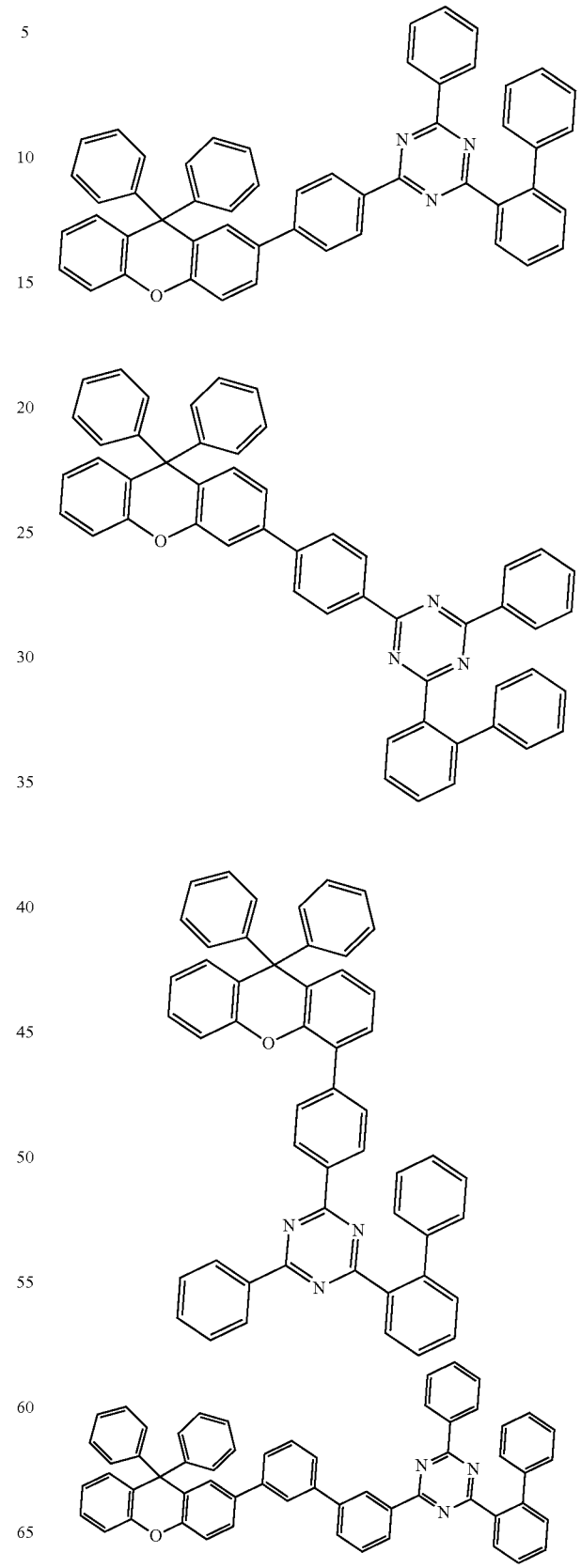

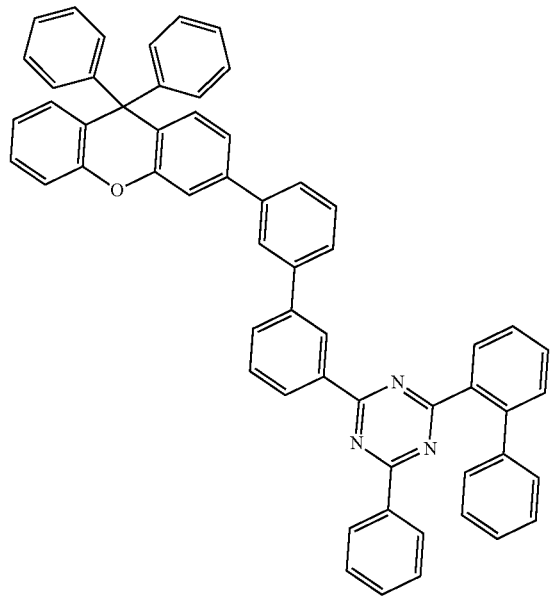
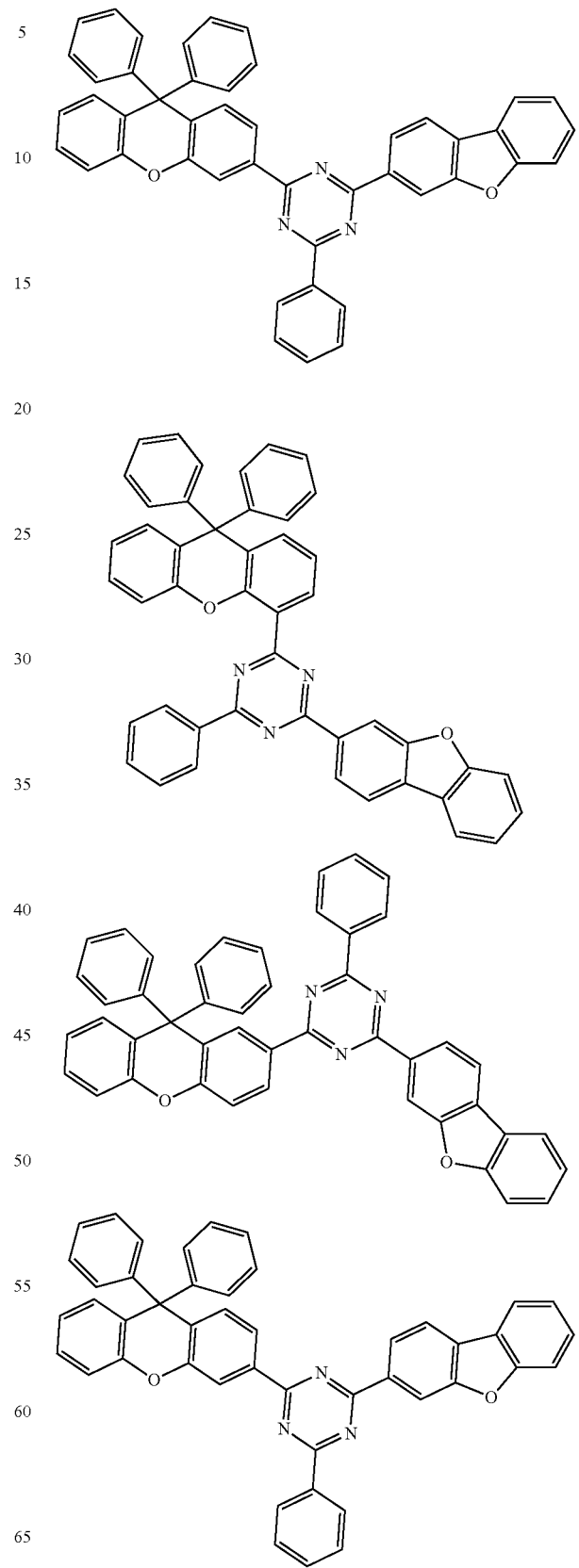

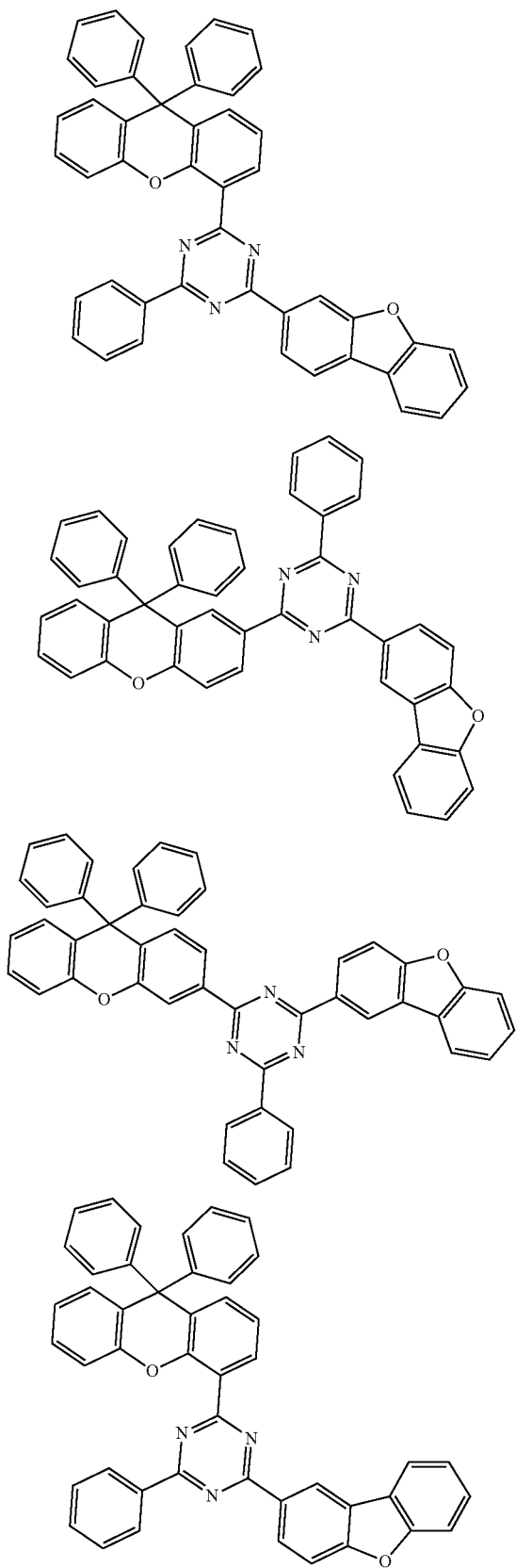
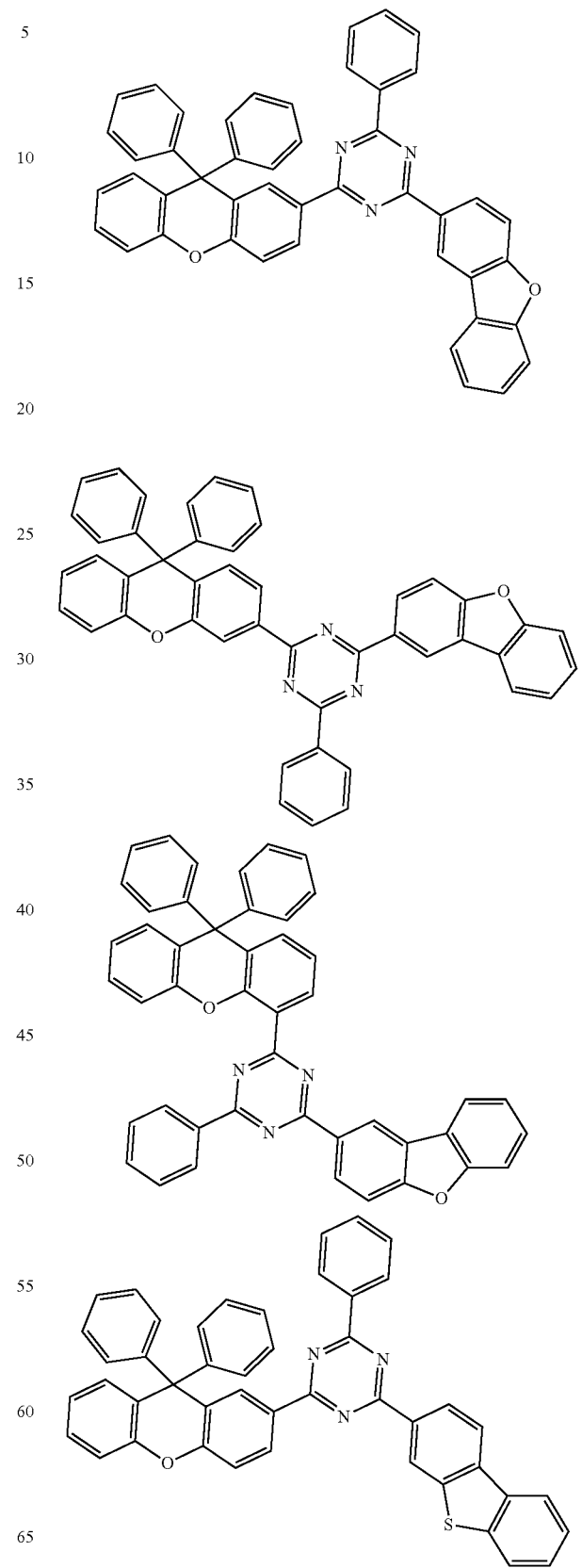

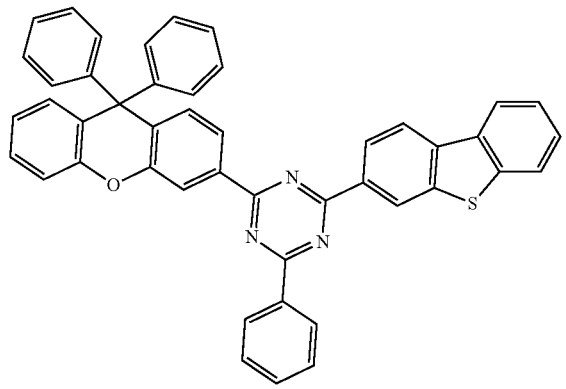
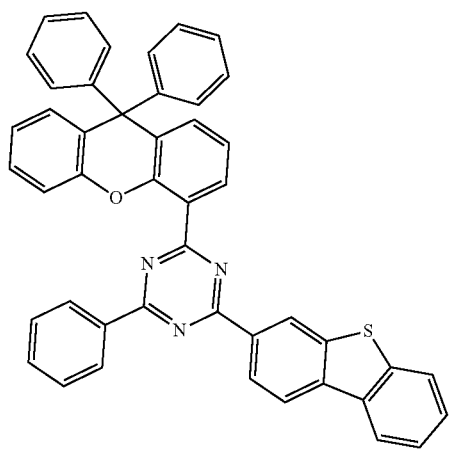
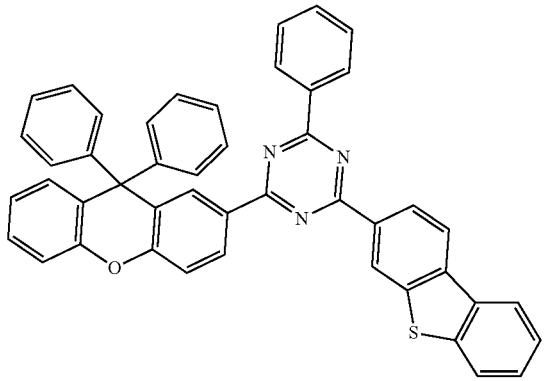
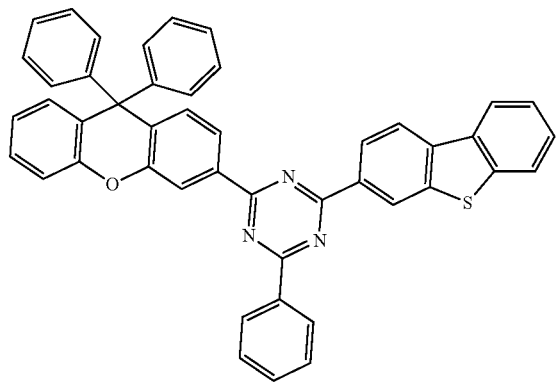
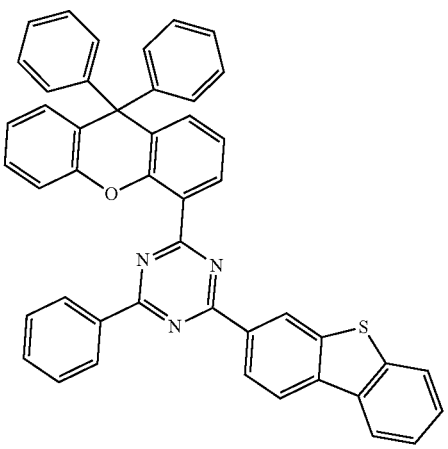
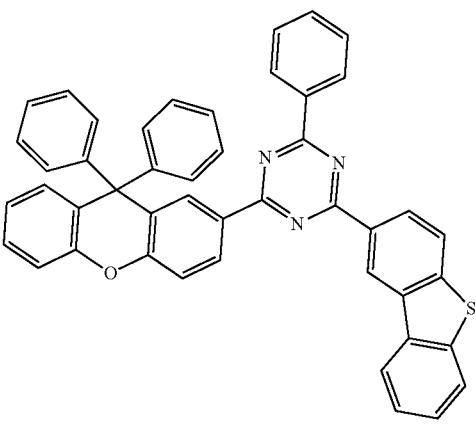
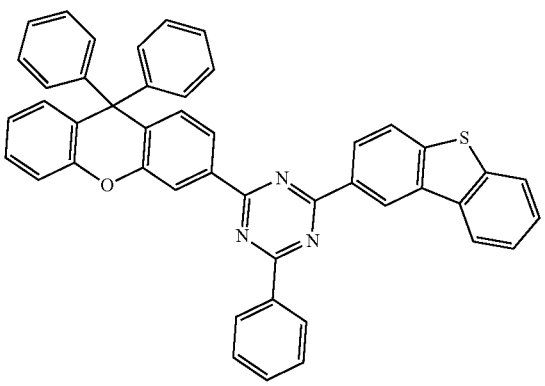
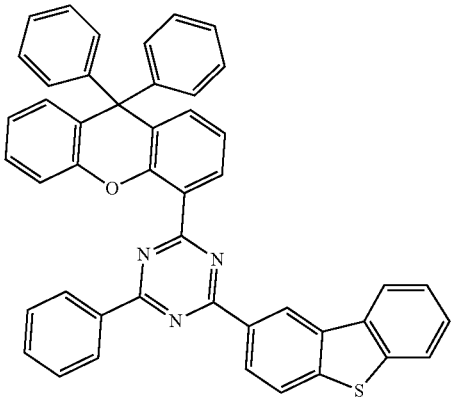

-continued
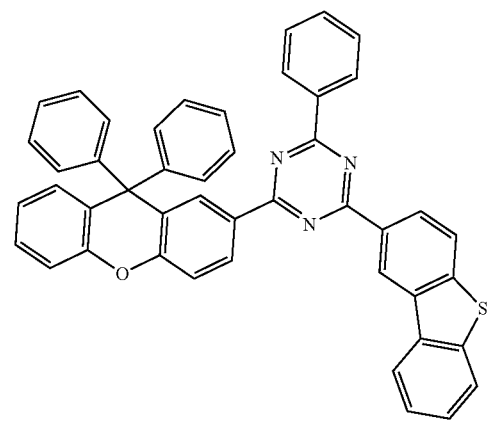
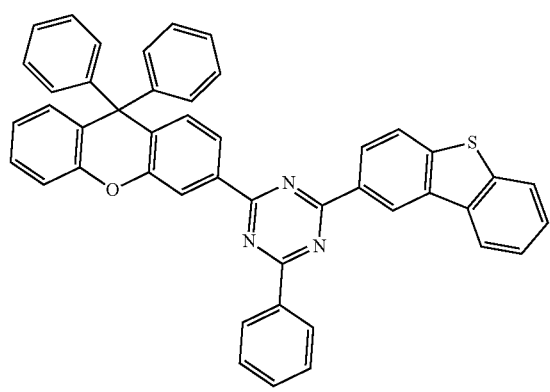
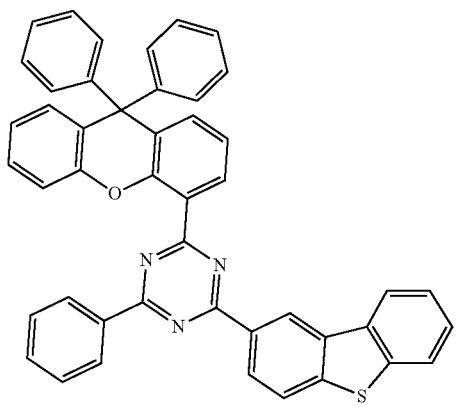
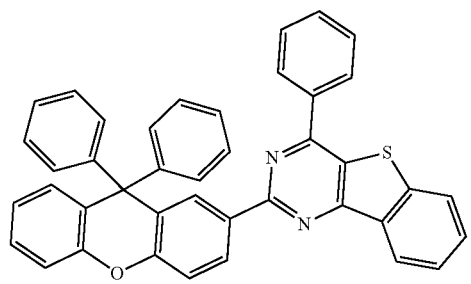
-continued
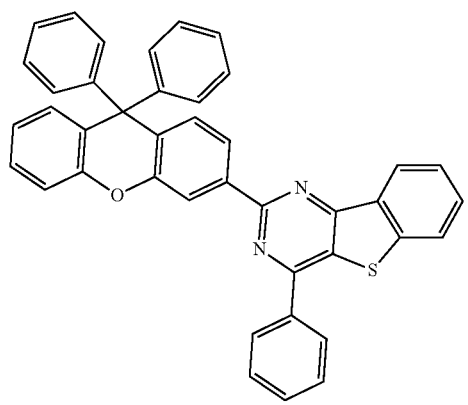
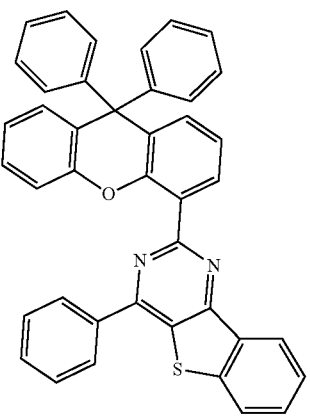
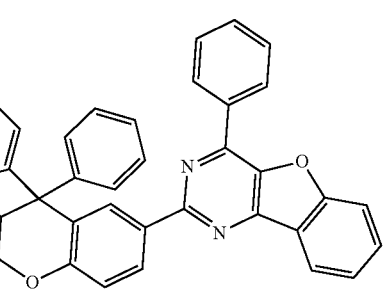
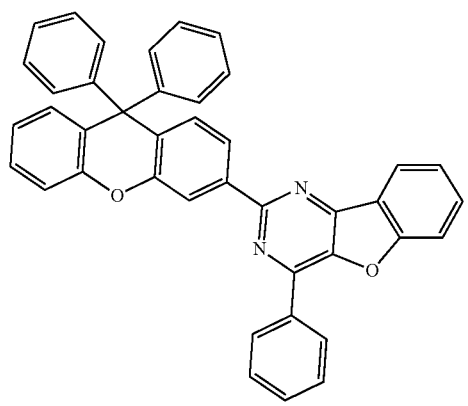

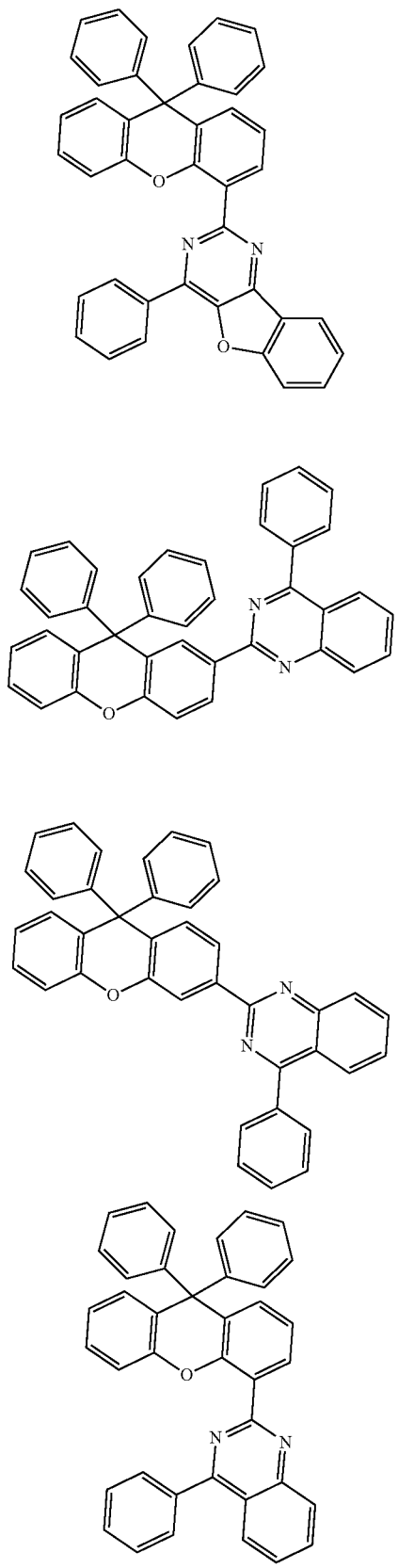
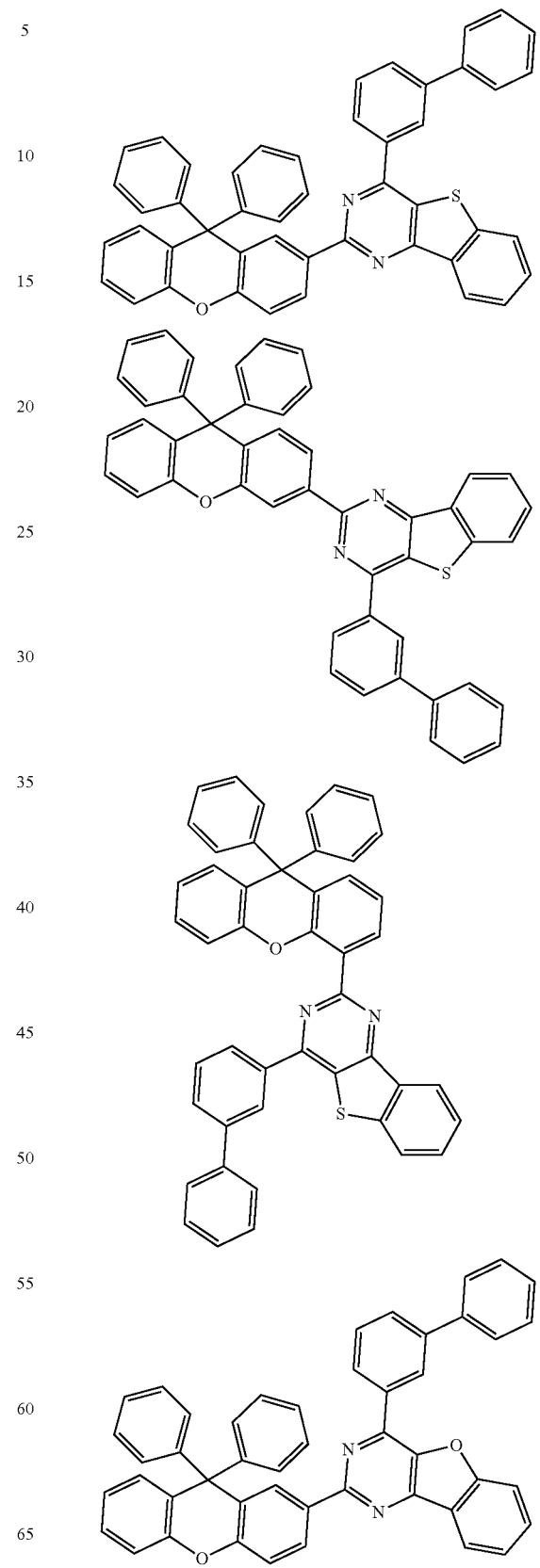

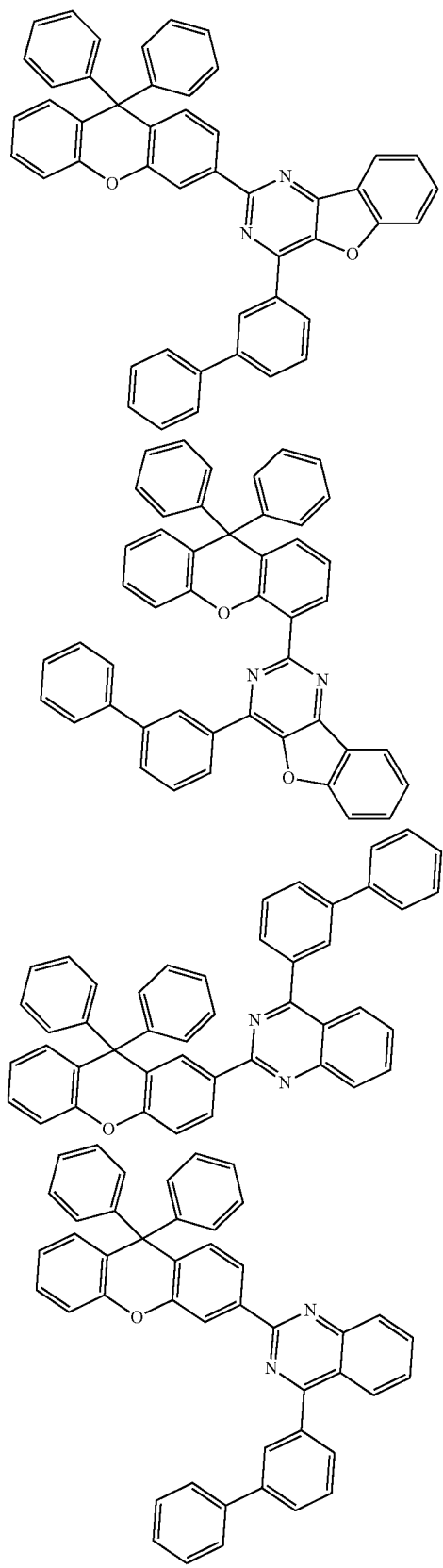
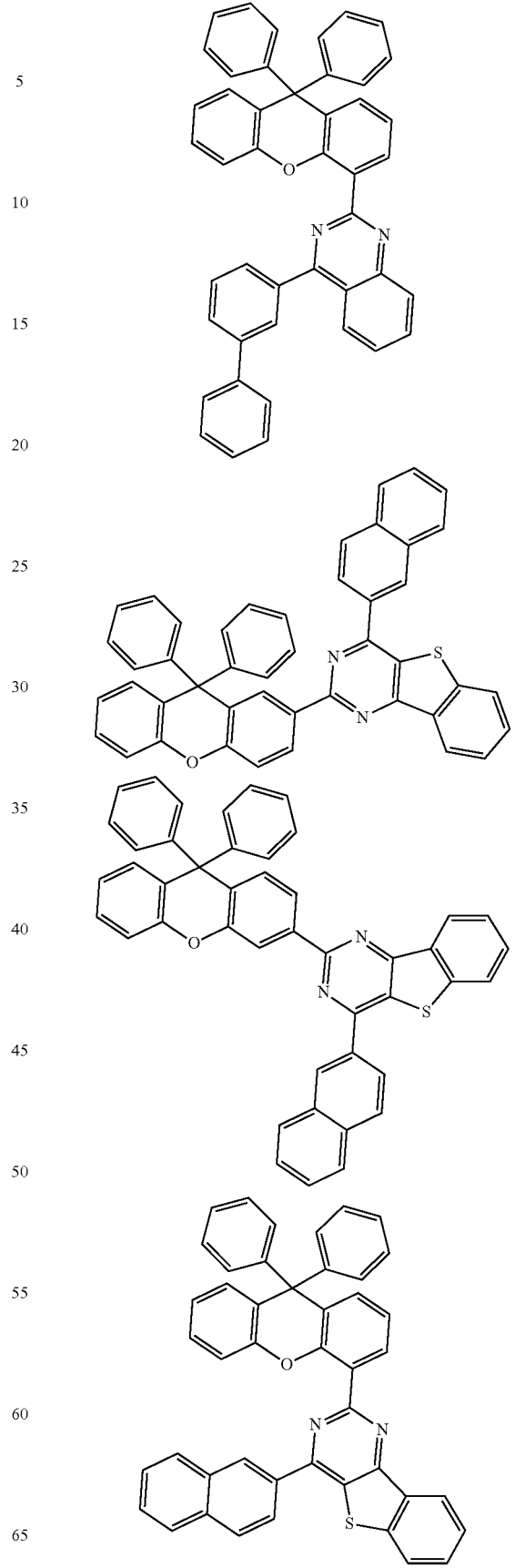

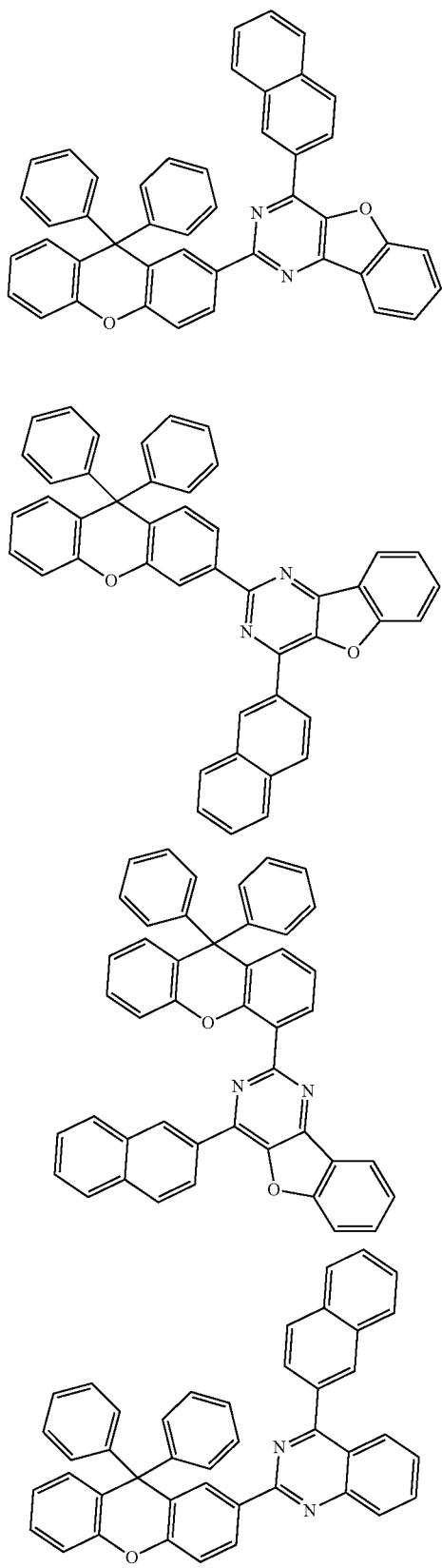
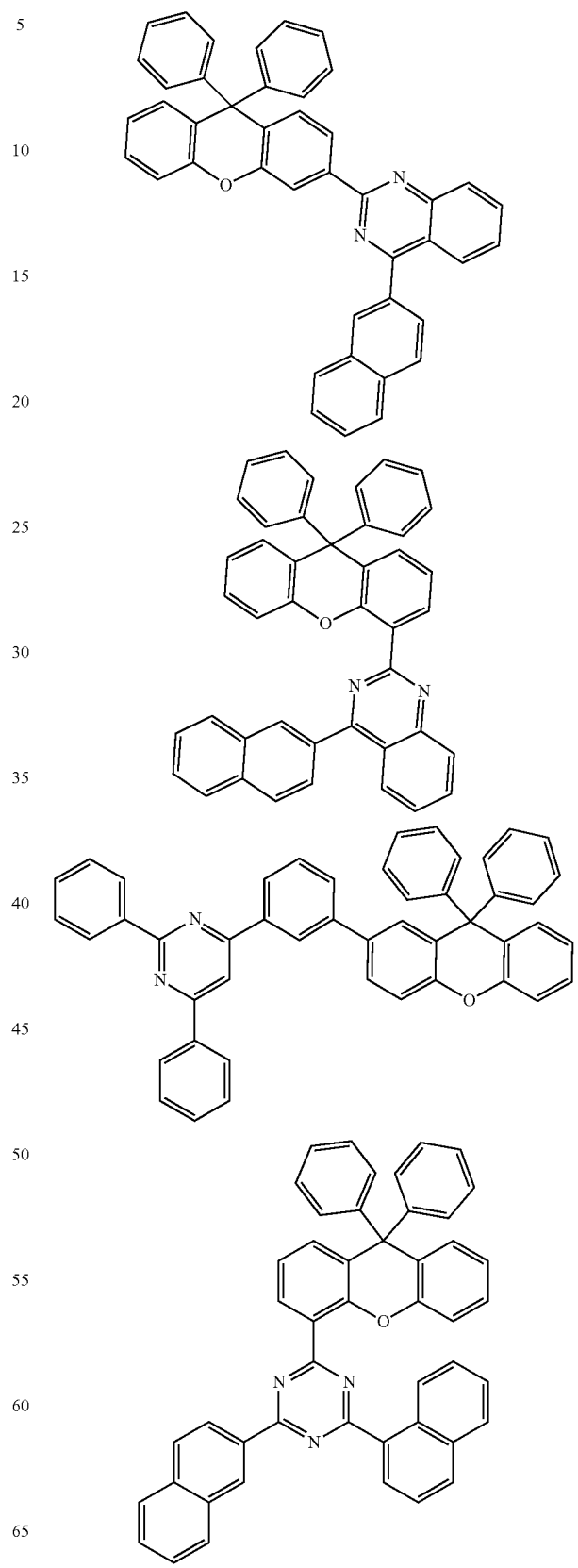

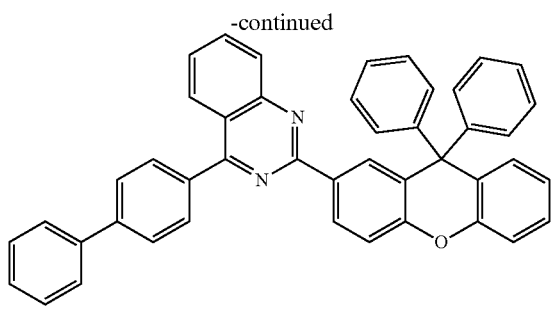

The compounds represented by Chemical Formula 1 can be prepared, for example, according to the preparation method as shown in the following Reaction Scheme 1, and the remaining compounds can be prepared in a similar manner.

[Reaction Scheme 1]

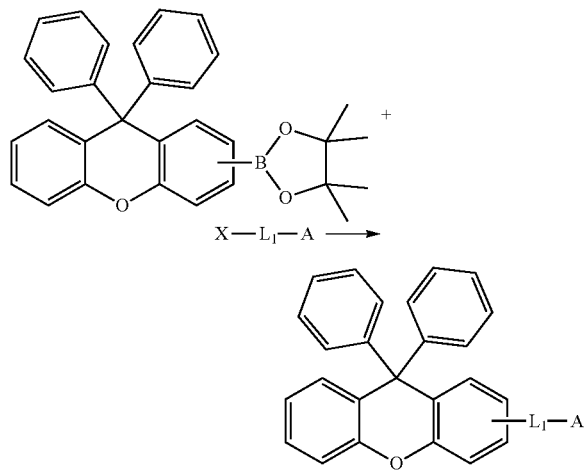

Herein, in Reaction Scheme 1, $L_1$ and A are the same as defined above, and X is a halogen, and preferably, X is chloro or bromo.

Reaction Scheme 1 is a Suzuki coupling reaction, which is preferably carried out in the presence of a palladium catalyst and a base, and the reactive group for the Suzuki coupling reaction can be modified as known in the art. The above preparation method can be further specified in preparation examples described hereinafter.

In another embodiment of the invention, an organic light emitting device is provided, including a compound represented by Chemical Formula 1. As an example, an organic light emitting device is provided, including: a first electrode; a second electrode provided to face the first electrode; and one or more organic material layers provided between the first electrode and the second electrode, wherein one or more layers of the organic material layers includes the compound represented by Chemical Formula 1.

The organic material layer of the organic light emitting device of the present invention may have a single layer structure, or it may have a multilayered structure in which two or more organic material layers are stacked. For example, the organic light emitting device of the present disclosure may have a structure including a hole injection layer, a hole transport layer, an electron blocking layer, a light emitting layer, a hole blocking layer, an electron transport layer, an electron injection layer, and the like as the organic material layer. However, the structure of the organic light emitting device is not limited thereto, and it may include a smaller number of organic layers.

Further, the organic material layer may include a light emitting layer, wherein the light emitting layer includes a compound represented by Chemical Formula 1. In particular, the compound according to the present invention can be used as a host in a light emitting layer.

The organic material layer may include an electron transport layer or an electron injection layer, wherein the electron transport layer or the electron injection layer may include a compound represented by Chemical Formula 1.

The electron transport layer, the electron injection layer, or a layer simultaneously performing electron transport and electron injection may include a compound represented by Chemical Formula The organic material layer may include a light emitting layer and an electron transport layer, wherein the electron transport layer may include a compound represented by Chemical Formula 1.

The organic material layer may include a hole blocking layer, wherein the hole blocking layer may include a compound represented by Chemical Formula 1.

The organic material layer may include an electron blocking layer, wherein the electron blocking layer may include a compound represented by Chemical Formula 1.

The organic light emitting device according to the present invention may be a normal type of organic light emitting device in which an anode, one or more organic material layers, and a cathode are sequentially stacked on a substrate. Further, the organic light emitting device according to the present disclosure may be an inverted type of organic light emitting device in which a cathode, one or more organic material layers, and an anode are sequentially stacked on a substrate. For example, the structure of an organic light emitting device according to an embodiment of the present disclosure is illustrated in FIGS. 1 and 2.

FIG. 1 shows an example of an organic light emitting device including a substrate 1, an anode 2, a light emitting layer 3, and a cathode 4. In such a structure, the compound represented by Chemical Formula 1 may be included in the light emitting layer.

FIG. 2 shows an example of an organic light emitting device including a substrate 1, an anode 2, a hole injection layer 5, a hole transport layer 6, an electron blocking layer 7, a light emitting layer 3, a hole blocking layer 8, an electron transport layer 9, and a cathode 4. In such a structure, the compound represented by Chemical Formula 1 may be included in one or more layers of the hole injection layer, the hole transport layer, the electron blocking layer, the light emitting layer, the hole blocking layer, and the electron transport layer.

The organic light emitting device according to the present invention may be manufactured by materials and methods known in the art, except that one or more layers of the organic material layers include the compound represented by Chemical Formula 1. In addition, when the organic light emitting device includes a plurality of organic material layers, the organic material layers may be formed of the same material or different materials.

For example, the organic light emitting device according to the present invention can be manufactured by sequentially stacking a first electrode, an organic material layer, and a second electrode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer, the hole blocking layer and the electron transport layer thereon, and then depositing a material that can be used as the cathode thereon. In addition to such a method, the organic light emitting device may be manufactured by sequentially depositing a cathode material, an organic material layer, and an anode material on a substrate.

Further, the compound represented by Chemical Formula 1 may be formed into an organic layer by a solution coating method as well as a vacuum deposition method at the time of manufacturing an organic light emitting device. Herein, the solution coating method means spin coating, dip coating, doctor blading, inkjet printing, screen printing, a spray method, roll coating, or the like, but is not limited thereto.

In addition to such a method, the organic light emitting device may be manufactured by sequentially depositing a cathode material, an organic material layer, and an anode material on a substrate (International Publication WO2003/012890). However, the manufacturing method is not limited thereto.

As an example, the first electrode is an anode and the second electrode is a cathode, or alternatively, the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as $ZnO:Al$ or $SnO_2:Sb$, conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to a electron injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrin, oligothiophene, an arylamine-based organic material, a hexanitrilehexaazatriphenylene-based organic material, a quinacridone-based organic material, a perylene-based organic material, anthraquinone, a polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxyquinoline aluminum complex ($Alq_3$), a carbazole-based compound; a dimerized styryl compound; BAlq; a 10-hydroxybenzoquinoline-metal compound; a benzoxazole, benzothiazole and benzimidazole-based compound; a poly(p-phenylene vinylene)(PPV)-based polymer; a spiro compound; polyfluorene, rubrene, and the like, but are not limited thereto.

The electron blocking layer is a layer provided between the hole transport layer and the light emitting layer in order to prevent the electrons injected from the cathode from being transferred to the hole transport layer without being recombined in the light emitting layer, which may be referred to as an electron inhibition layer. The electron blocking layer is preferably a material having a smaller electron affinity than the electron transport layer.

The light emitting layer may include a host material and a dopant material. The host material may be a fused aromatic ring derivative, a heterocycle-containing compound, or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene, and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The hole blocking layer is a layer provided between the electron transport layer and the light emitting layer in order to prevent the holes injected from the anode from being transferred to the electron transport layer without being recombined in the light emitting layer, which may be referred to as a hole inhibition layer. The hole blocking layer is preferably a material having high ionization energy. Preferably, the compound represented by Chemical Formula 1 may be included as a material of the hole blocking layer.

The electron transport layer is a layer which receives electrons from an electron injection layer and transports the electrons to a light emitting layer, and an electron transport material is suitably a material which may receive electrons well from a cathode and transfer the electrons to a light emitting layer, and has high mobility for electrons. Specific examples of the electron transport material include: an Al complex of 8-hydroxyquinoline; a complex including $Alq_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer. Preferably, the compound represented by Chemical Formula 1 may be included as a material of the electron transport layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present invention may be a front emission type, a rear emission type, or a double side emission type according to the used material.

In addition, the compound represented by Chemical Formula may be included in an organic solar cell or an organic transistor in addition to an organic light emitting device.

The invention will be described in detail in the following examples. However, these examples are presented for illustrative purposes only, and are not intended to limit the scope of the present invention.

PREPARATION EXAMPLES

Preparation Example 1: Preparation of Compound 1

1-1. Preparation of Intermediate A

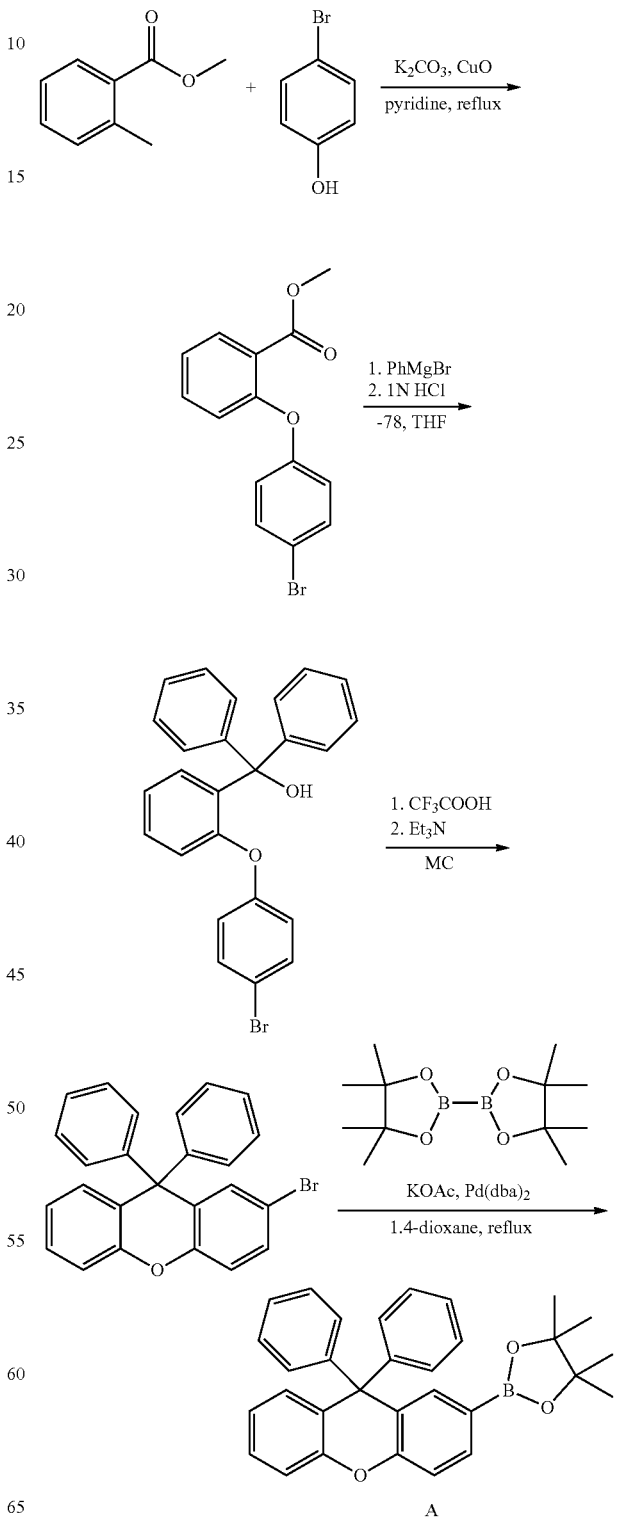

A

1-2. Preparation of Compound

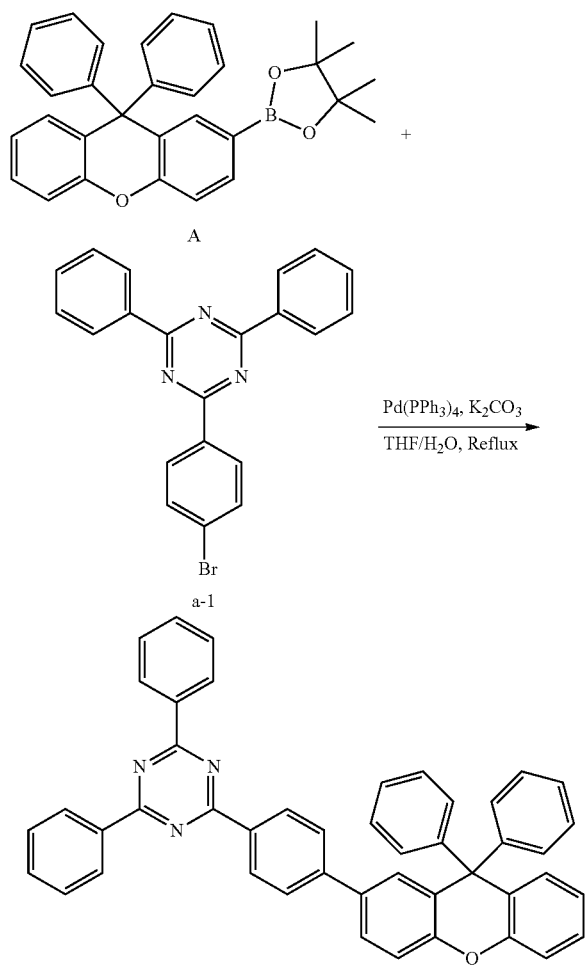

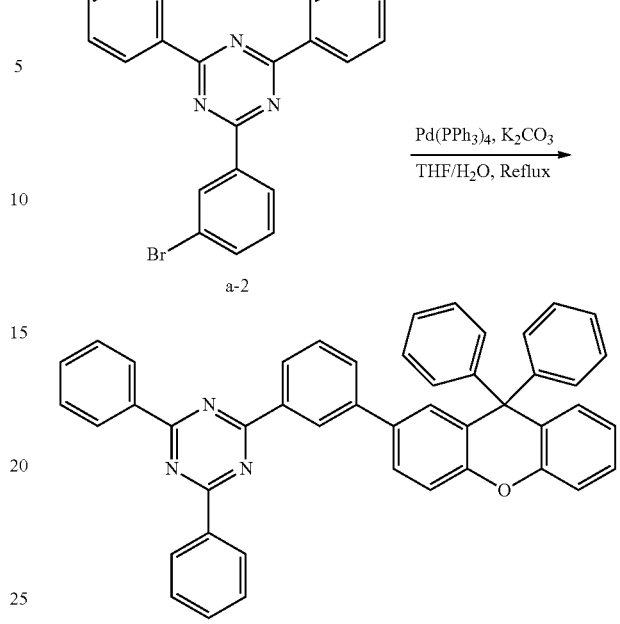

Intermediate A (7.50 g, 16.31 mmol) and Intermediate a-1 (6.01 g, 15.53 mmol) were completely dissolved in tetrahydrofuran (280 ml) in a 500 ml round bottom flask under a nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate, then concentrated under reduced pressure and recrystallized with tetrahydrofuran (210 ml) to prepare Compound 1 (8.26 g, yield: 72%).

MS: $[M+H]^+=642$

Preparation Example 2: Preparation of Compound 2

Intermediate A (7.50 g, 16.31 mmol) and Intermediate a-2 (6.01 g, 15.53 mmol) were completely dissolved in tetrahydrofuran (280 ml) in a 500 ml round bottom flask under a nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate then concentrated under reduced pressure, and recrystallized with ethyl acetate (280 ml) to prepare Compound 2 (6.86 g, yield: 59%).

MS: $[M+H]+=642$

Preparation Example 3: Preparation of Compound 3

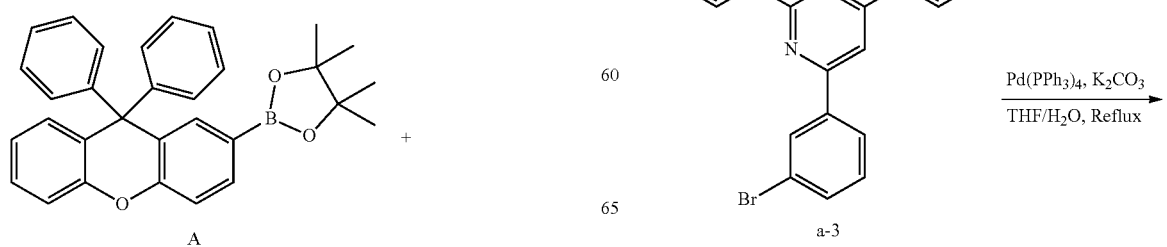

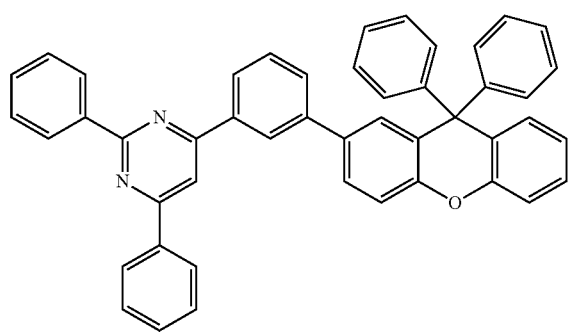

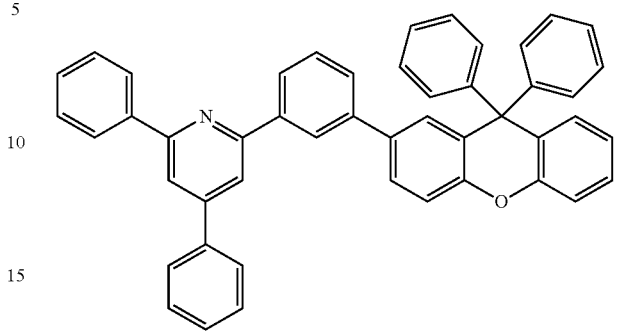

Intermediate A (7.50 g, 16.31 mmol) and Intermediate a-3 (6.01 g, 15.53 mmol) were completely dissolved in tetrahydrofuran (280 ml) in a 500 ml round bottom flask under a nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate then concentrated under reduced pressure, and recrystallized with ethyl acetate (250 ml) to prepare Compound 3 (6.52 g, yield: 57%).

MS: [M+H]$^+$=641

Preparation Example 4: Preparation of Compound 4

Intermediate A (7.50 g, 16.31 mmol) and Intermediate a-4 (6.01 g, 15.53 mmol) were completely dissolved in tetrahydrofuran (280 ml) in a 500 ml round bottom flask under a nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate then concentrated under reduced pressure, and recrystallized with ethyl acetate (230 ml) to prepare Compound 4 (6.31 g, yield: 55%).

MS: [M+H]+=640

Preparation Example 5: Preparation of Compound 5

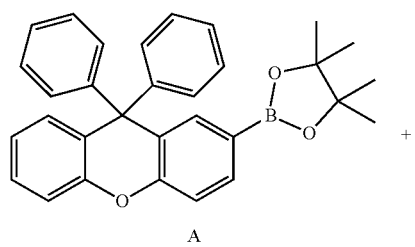

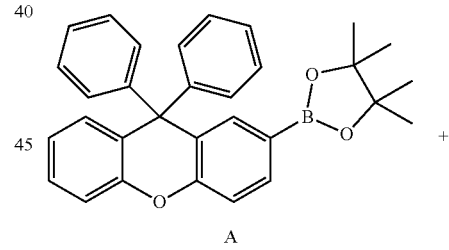

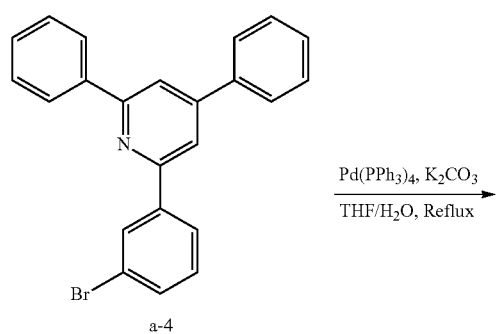

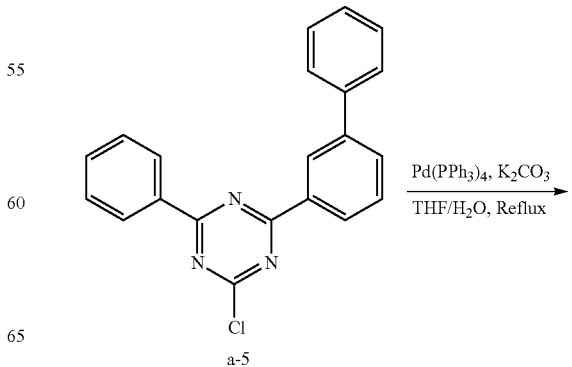

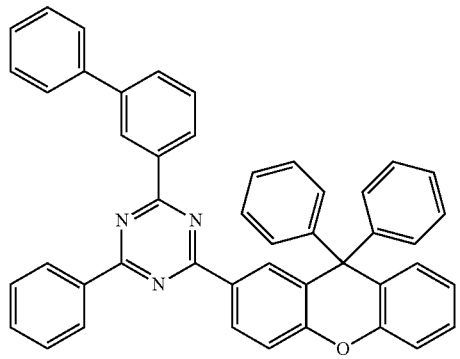

Intermediate A (7.51 g, 16.32 mmol) and Intermediate a-5 (5.33 g, 15.54 mmol) were completely dissolved in tetrahydrofuran (280 ml) in a 500 ml round bottom flask under a nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate then concentrated under reduced pressure, and recrystallized with ethyl acetate (180 ml) to prepare Compound 5 (5.97 g, yield: 60%).

MS: [M+H]+=642

Preparation Example 6: Preparation of Compound 6

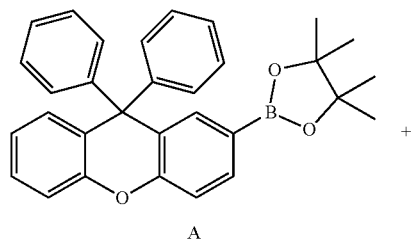

A

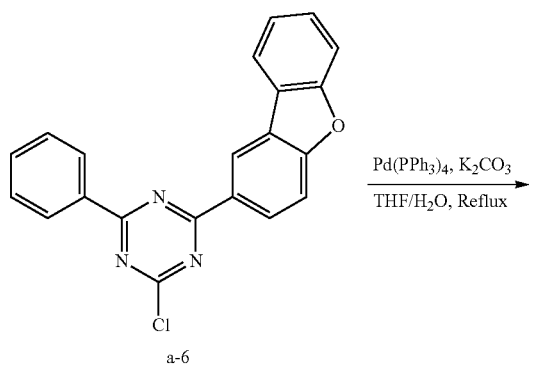

a-6

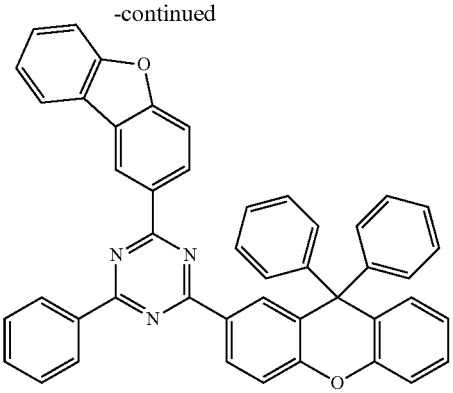

Intermediate A (7.50 g, 16.31 mmol) and Intermediate a-6 (5.54 g, 15.52 mmol) were completely dissolved in tetrahydrofuran (280 ml) in a 500 ml round bottom flask under a nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate then concentrated under reduced pressure, and recrystallized with ethyl acetate (210 ml) to prepare Compound 6 (5.97 g, yield: 60%).

MS: [M+H]+=656

Preparation Example 7: Preparation of Compound 7

7-1. Preparation of Intermediate B

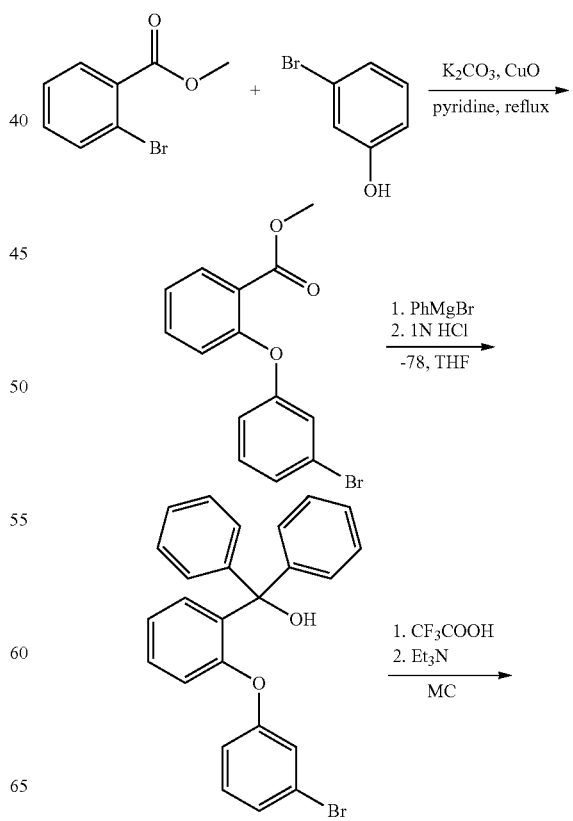

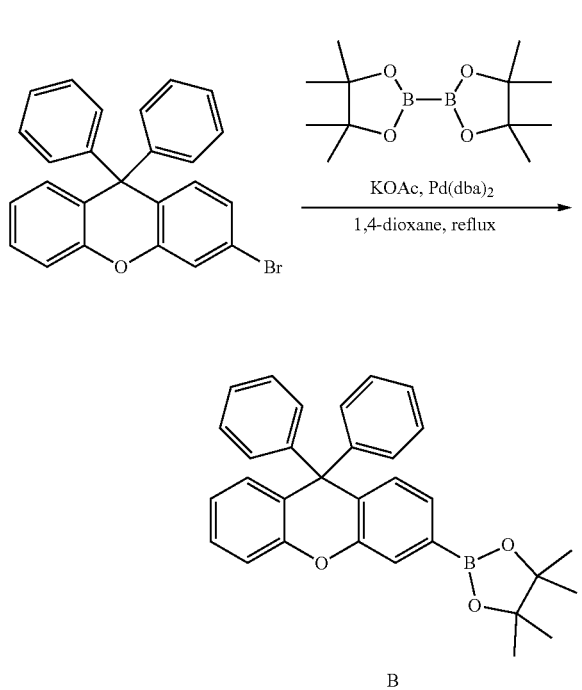

7-2. Preparation of Compound 7

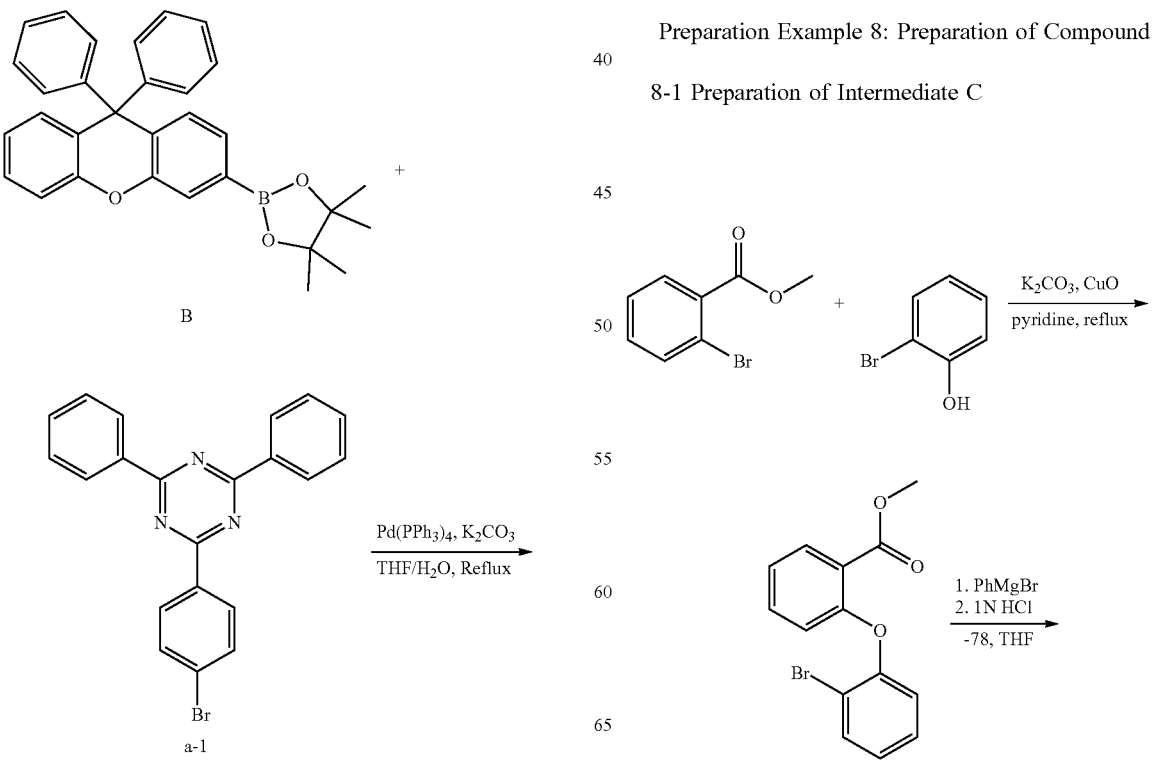

Intermediate B (7.50 g, 16.31 mmol) and Intermediate a-1 (6.01 g, 15.53 mmol) were completely dissolved in tetrahydrofuran (280 ml) in a 500 ml round bottom flask under a nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate then concentrated under reduced pressure, and recrystallized with tetrahydrofuran (210 ml) to prepare Compound 7 (7.16 g, yield: 72%).

MS: $[M+H]^+=642$

Preparation Example 8: Preparation of Compound 8

8-1 Preparation of Intermediate C

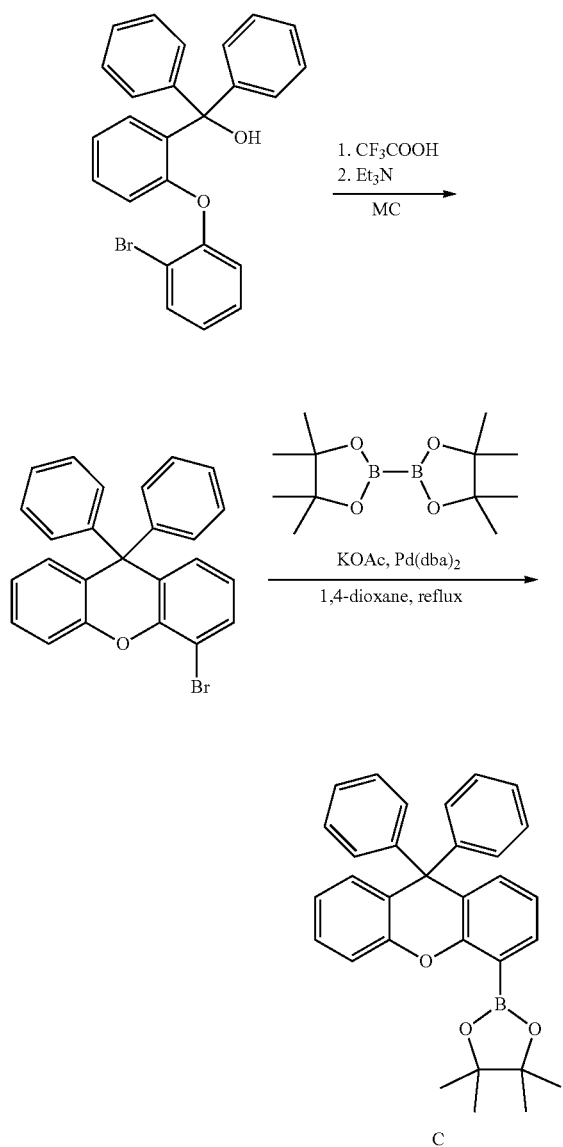

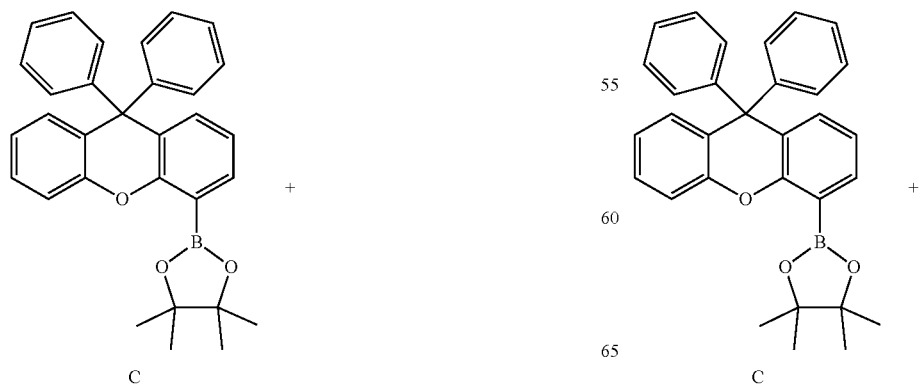

Intermediate C (7.50 g, 16.31 mmol) and Intermediate a-8 (5.70 g, 15.53 mmol) were completely dissolved in tetrahydrofuran (280 ml) in a 500 ml round bottom flask under a nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate then concentrated under reduced pressure, and recrystallized with ethyl acetate (200 ml) to prepare Compound 8 (8.22 g, yield: 79%).

MS: $[M+H]^+=666$

Preparation Example 9: Preparation of Compound 9

8-2 Preparation of Compound 8

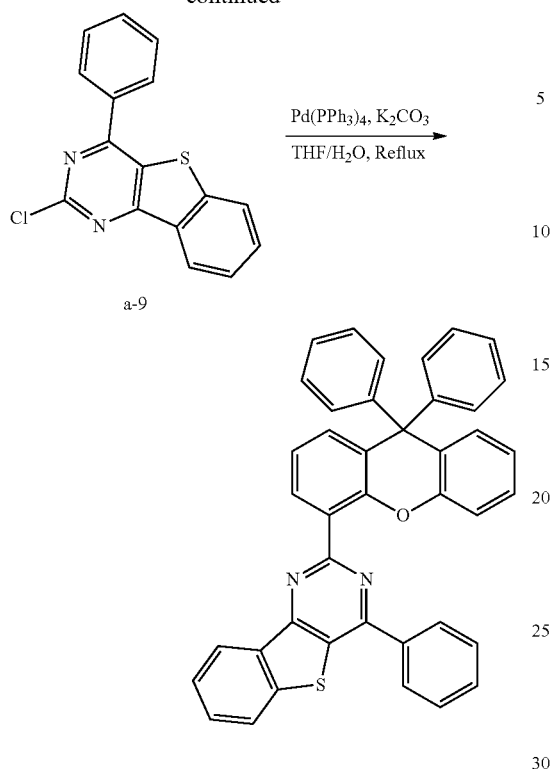

a-9

Intermediate C (7.50 g, 16.31 mmol) and Intermediate a-9 (5.70 g, 15.53 mmol) were completely dissolved in tetrahydrofuran (280 ml) in a 500 ml round bottom flask under a nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate then concentrated under reduced pressure, and recrystallized with ethyl acetate (240 ml) to prepare Compound 9 (8.22 g, yield: 79%).

MS: [M+H]$^+$=597

Preparation Example 10: Preparation of Compound 10

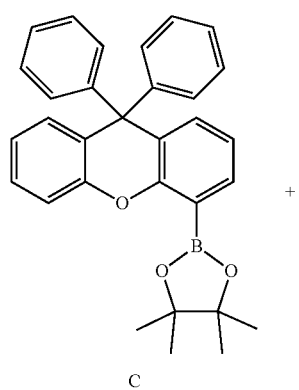

C

+

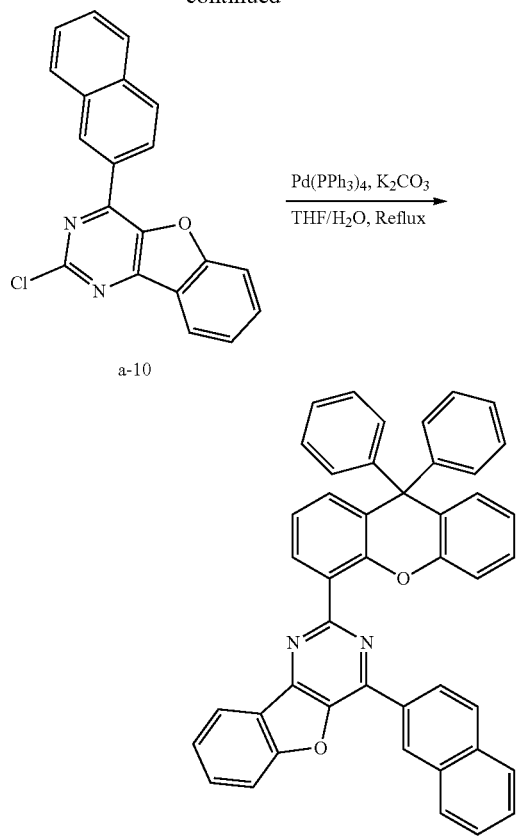

a-10

Intermediate C (7.50 g, 16.31 mmol) and Intermediate a-10 (5.70 g, 15.53 mmol) were completely dissolved in tetrahydrofuran (280 ml) in a 500 ml round bottom flask under a nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate then concentrated under reduced pressure, and recrystallized with ethyl acetate (260 ml) to prepare Compound 10 (8.22 g, yield: 79%).

MS: [M+H]$^+$=631

Preparation Example 11: Preparation of Compound 11

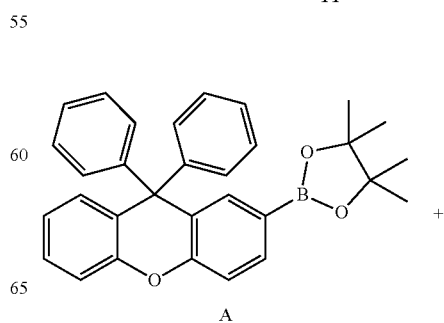

A

+

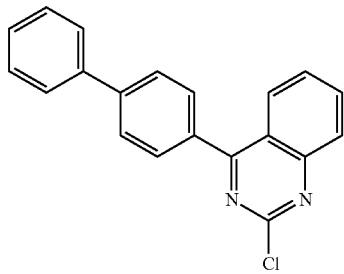

a-11

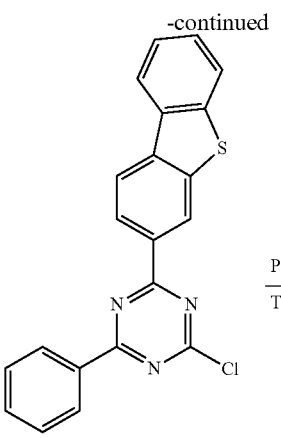

a-12

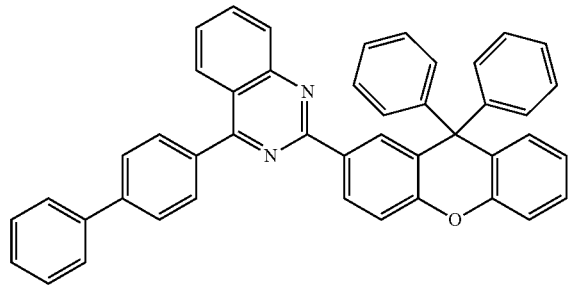

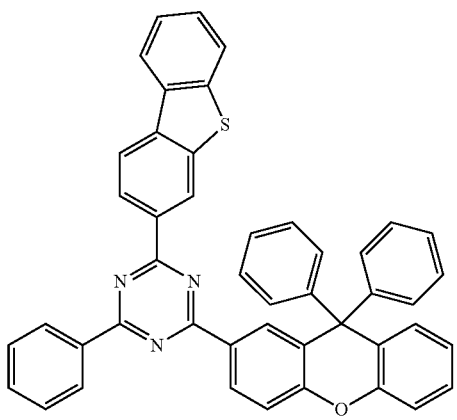

Intermediate A (7.50 g, 16.31 mmol) and Intermediate a-11 (4.91 g, 15.54 mmol) were completely dissolved in tetrahydrofuran (280 ml) in a 500 ml round bottom flask under a nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate then concentrated under reduced pressure, and recrystallized with ethyl acetate (230 ml) to prepare Compound 11 (5.97 g, yield: 60%).

MS: [M+H]$^+$=615

Preparation Example 12: Preparation of Compound 12

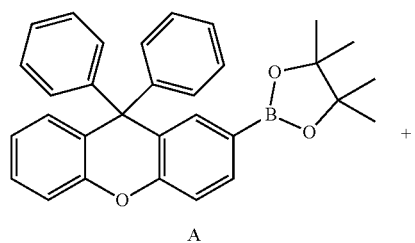

A

Intermediate A (11.94 g, 25.96 mmol) and Intermediate a-12 (8.42 g, 22.57 mmol) were completely dissolved in tetrahydrofuran (220 ml) in a 500 ml round bottom flask under a nitrogen atmosphere, to which a 2M aqueous potassium carbonate solution (110 ml) was added and tetrakis-(triphenylphosphine)palladium (0.78 g, 0.68 mmol) was added, and then the resulting mixture was heated and stirred for 3 hours. The temperature was lowered to normal temperature, the aqueous layer was removed, and the resulting product was dried over anhydrous magnesium sulfate then concentrated under reduced pressure, and recrystallized with ethyl acetate (240 ml) to prepare Compound 12 (8.02 g, yield: 53%).

MS: [M+H]$^+$=672

EXAMPLES

Example 1-1

A glass substrate on which ITO (indium tin oxide) was coated as a thin film to a thickness of 1000 Å was put into distilled water in which a detergent was dissolved, and ultrasonically cleaned. In this case, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, then dried and transferred to a plasma cleaner.

In addition, the substrate was cleaned for 5 minutes using oxygen plasma, and then transferred to a vacuum depositor.

On the ITO transparent electrode which is the anode electrode thus prepared, the following compound HI1 and the following compound HI2 were thermally vacuum deposited at a molar ratio of 98:2 to have a thickness of 100 Å, thereby forming a hole injection layer. The following compound HT1 was vacuum deposited on the hole injection layer to a thickness of 1150 Å to form a hole transport layer. The following compound EB1 was vacuum deposited on the hole transport layer to a thickness of 50 Å to form an electron blocking layer. Then, the following compound BH and the following compound BD were vacuum deposited at a weight ratio of 50:1 on the electron blocking layer to a thickness of 200 Å to form a light emitting layer. Compound 1 prepared in Preparation Example 1 above was vacuum deposited on the light emitting layer to a thickness of 50 Å to form a hole blocking layer. Then, the following compound ET1 and the following compound LiQ were vacuum deposited at a weight ratio of 1:1 on the hole blocking layer to form an electron transport layer with a thickness of 30 Å. Lithium fluoride (LiF) and aluminum were sequentially deposited to have a thickness of 12 Å and 1000 Å, respectively, on the electron transport layer, thereby forming a cathode.

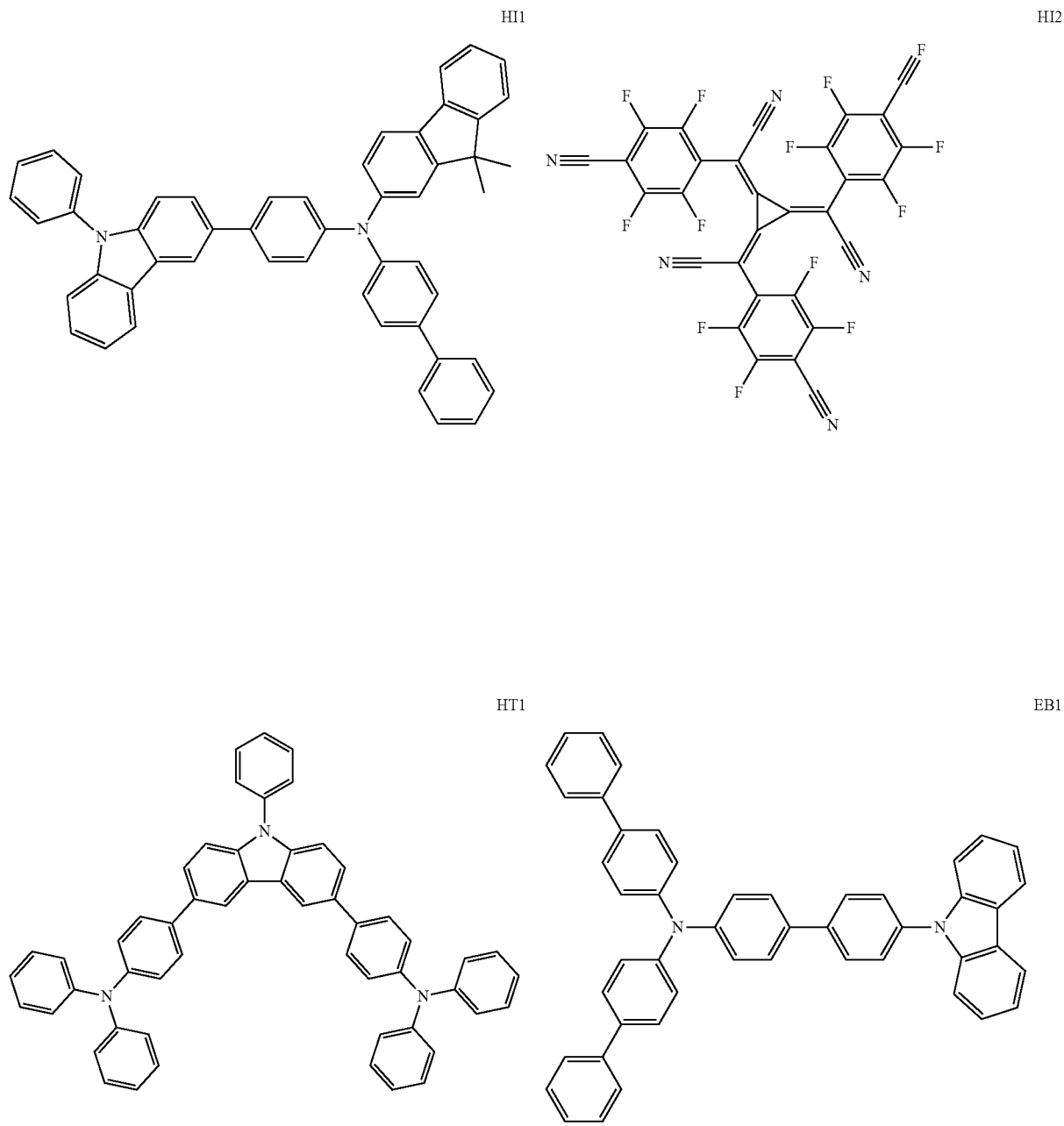

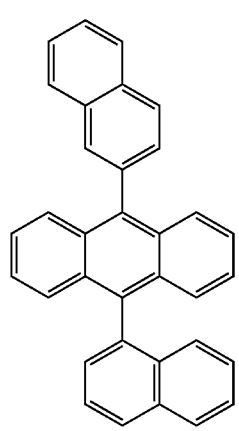

BH

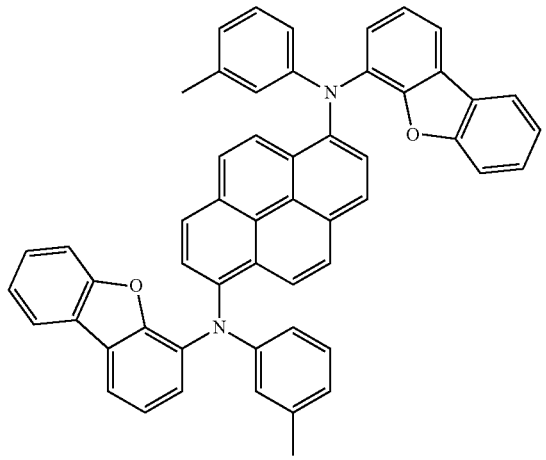

BD

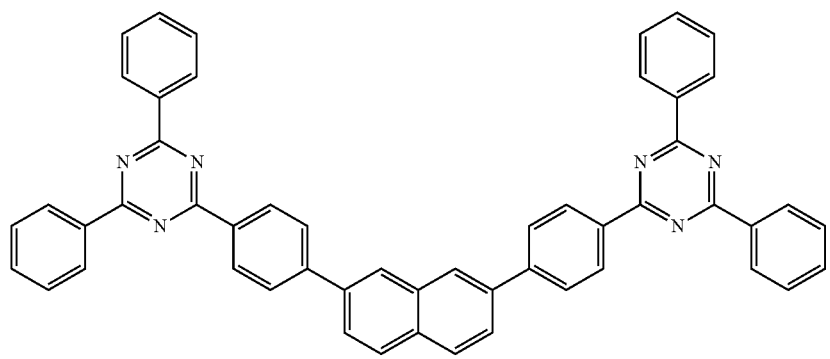

ET1

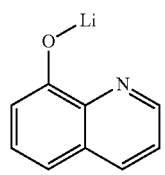

LiQ

In the above-mentioned process, the vapor deposition rate of the organic material was maintained at 0.4 to 0.7 Å/s, the deposition rates of lithium fluoride and aluminum of the cathode were maintained at 0.3 Å/s and at 2 Å/s, respectively, and the degree of vacuum during the deposition was maintained at $2\times10^{-7}$ to $5\times10^{-6}$ Torr, thereby manufacturing an organic light emitting device.

Examples 1-2 to 1-5

Organic light emitting devices were respectively manufactured in the same manner as in Example 1-1, except that the compounds shown in Table 1 below were used instead of Compound 1 during the formation of the hole blocking layer.

Comparative Examples 1-1 to 1-3

An organic light emitting device was manufactured in the same manner as in Example 1-1, except that the compounds shown in Table 1 below were used instead of Compound 1 during the formation of the hole blocking layer. The compounds of HB2, HB3, and HB4 used in Table 1 below are as follows:

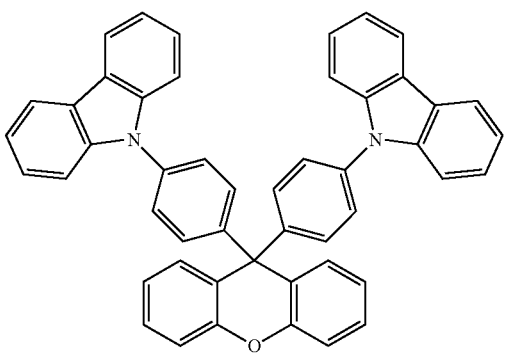

HB2

HB3

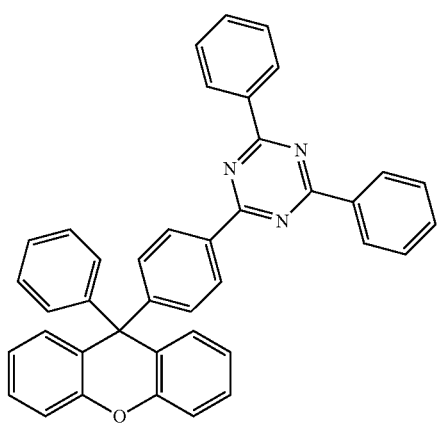

HB4

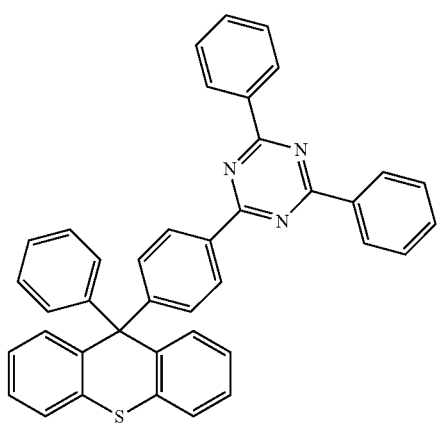

The voltage, efficiency, color coordinates, and lifetime were measured by applying a current of 20 mA/cm² to the organic light emitting devices manufactured in Examples 1-1 to 1-5 and Comparative Examples 1-1 to 1-3, and the results are shown in Table 1 below. T95 means the time required for the luminance to be reduced to 95% of the initial luminance (1600 nit).

TABLE 1

|  | Compound (hole blocking layer) | Voltage (V) (@20 mA/cm²) | Efficiency (cd/A) (@20 mA/cm²) | Color coordinates (x, y) | T95(hr) (@20 mA/cm²) |
| --- | --- | --- | --- | --- | --- |
| Example 1-1 | Compound 1 | 4.15 | 6.77 | (0.144, 0.046) | 280 |
| Example 1-2 | Compound 2 | 4.13 | 6.76 | (0.142, 0.048) | 275 |
| Example 1-3 | Compound 3 | 4.24 | 6.62 | (0.143, 0.047) | 260 |
| Example 1-4 | Compound 4 | 4.26 | 6.63 | (0.143, 0.046) | 240 |
| Example 1-5 | Compound 7 | 4.27 | 6.61 | (0.144, 0.045) | 255 |
| Comparative Example 1-1 | HB2 | 4.79 | 5.45 | (0.145, 0.047) | 135 |
| Comparative Example 1-2 | HB3 | 4.65 | 5.64 | (0.147, 0.044) | 110 |
| Comparative Example 1-3 | HB4 | 4.81 | 5.38 | (0.147, 0.043) | 45 |

As shown in Table 1, the organic light emitting device manufactured by using the compound of the present invention as the hole blocking layer exhibited excellent characteristics in terms of driving voltage, light emitting efficiency, and lifetime of the organic light emitting device.

In particular, the organic light emitting device of the present invention exhibited low voltage, high efficiency, and long lifetime characteristics as compared with the organic light emitting devices manufactured by using HB3 and HB4 in which triazinyl was substituted at positions different from the examples of the present invention as hole blocking layers or by using HB2 substituted with carbazolyl as a hole blocking layer.

Examples 2-1 to 2-12

The organic light emitting devices were respectively manufactured in the same manner as in Example 1-1, except that the following compound HB1 was used instead of the compound 1 during the formation of the hole blocking layer, and the compounds shown in Table 2 below were used instead of the ET1 during the formation of the electron transport layer.

HB1

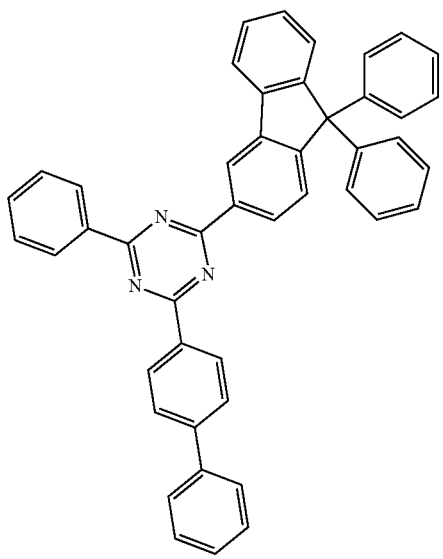

Comparative Examples 2-1 to 2-3

The organic light emitting devices were respectively manufactured in the same manner as in Example 1-1, except that the above compound HB1 was used instead of the compound 1 during the formation of the hole blocking layer, and the compounds shown in Table 2 below were used instead of the ET1 during the formation of the electron transport layer. The compounds of ET2, ET3 and Et4 used in Table 2 below are as follows:

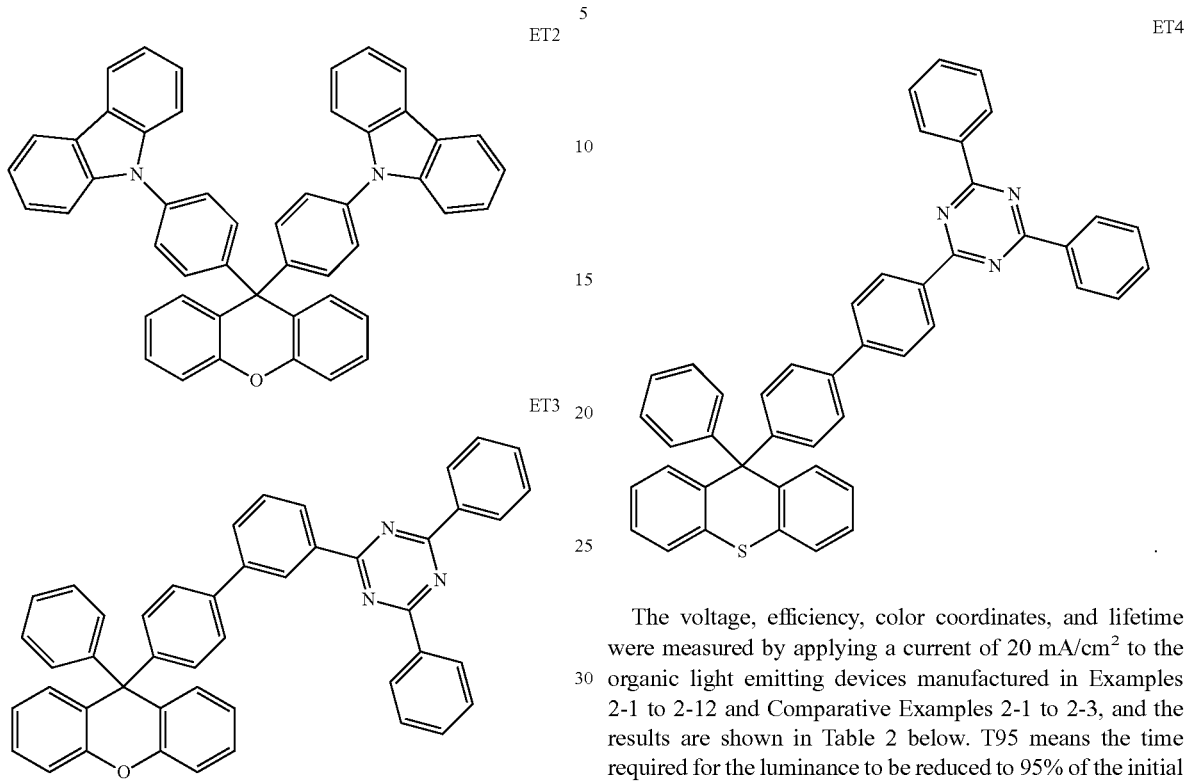

The voltage, efficiency, color coordinates, and lifetime were measured by applying a current of 20 mA/cm² to the organic light emitting devices manufactured in Examples 2-1 to 2-12 and Comparative Examples 2-1 to 2-3, and the results are shown in Table 2 below. T95 means the time required for the luminance to be reduced to 95% of the initial luminance (1600 nit).

TABLE 2

|  | Compound (electron-transport layer) | Voltage (V) (@20 mA/cm²) | Efficiency (cd/A) (@20 mA/cm²) | Color coordinates (x, y) | T95 (hr) (@20 mA/cm²) |
| --- | --- | --- | --- | --- | --- |
| Example 2-1 | Compound 1 | 4.30 | 6.34 | (0.144, 0.046) | 285 |
| Example 2-2 | Compound 2 | 4.33 | 6.85 | (0.144, 0.042) | 295 |
| Example 2-3 | Compound 3 | 4.35 | 6.56 | (0.145, 0.048) | 305 |
| Example 2-4 | Compound 4 | 4.34 | 6.77 | (0.144, 0.044) | 300 |
| Example 2-5 | Compound 5 | 4.26 | 6.68 | (0.144, 0.042) | 280 |
| Example 2-6 | Compound 6 | 4.27 | 6.59 | (0.145, 0.047) | 280 |
| Example 2-7 | Compound 7 | 4.38 | 6.71 | (0.145, 0.046) | 285 |
| Example 2-8 | Compound 8 | 4.31 | 6.63 | (0.144, 0.048) | 285 |
| Example 2-9 | Compound 9 | 4.34 | 6.55 | (0.144, 0.044) | 290 |
| Example 2-10 | Compound 10 | 4.25 | 6.41 | (0.144, 0.042) | 295 |
| Example 2-11 | Compound 11 | 4.26 | 6.66 | (0.145, 0.047) | 290 |
| Example 2-12 | Compound 12 | 4.41 | 6.73 | (0.144, 0.046) | 275 |
| Comparative Example 2-1 | ET2 | 4.84 | 5.74 | (0.142, 0.047) | 180 |
| Comparative Example 2-2 | ET3 | 5.48 | 4.85 | (0.143, 0.050) | 165 |
| Comparative Example 2-3 | ET4 | 5.16 | 5.14 | (0.143, 0.050) | 165 |

As shown in Table 2 above, the organic light emitting device manufactured by using the compound of the present invention as an electron transport layer exhibited excellent characteristics in terms of driving voltage, light emitting efficiency, and lifetime of the organic light emitting device.

The organic light emitting device of the present invention exhibited low voltage, high efficiency, and long lifetime characteristics as compared with the organic light emitting devices manufactured by using ET3 and ET4 in which triazinyl was substituted at positions different from the examples of the present invention as the electron transport layers or by using ET2 substituted with carbazolyl as the electron transport layer.

LIST OF REFERENCE SIGNS

1: substrate
2: anode
3: light emitting layer
4: cathode
5: hole injection layer
6: hole transport layer
7: electron blocking layer
8: hole blocking layer
9: electron transport layer

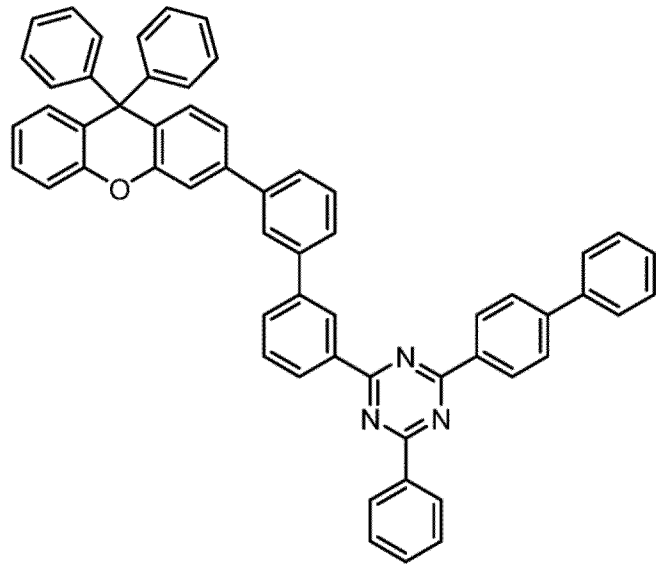

The invention claimed is:

1. A compound represented by the following Chemical Formula 1:

[Chemical Formula 1]

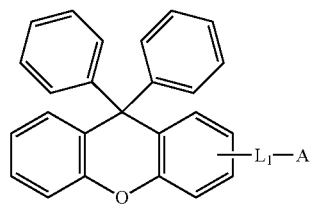

wherein in Chemical Formula 1,
$L_1$ is a single bond, or a substituted or unsubstituted $C_{6-60}$ arylene,
A is any one selected from the following groups,

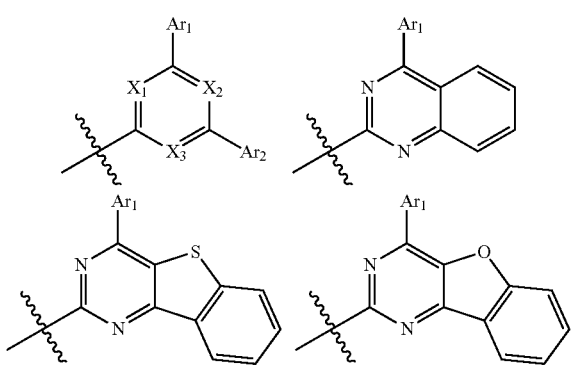

wherein $X_1$, $X_2$, and $X_3$ are each independently CH or N, provided that at least one of $X_1$, $X_2$, and $X_3$ is N, and $Ar_1$ and $Ar_2$ are each independently a substituted or unsubstituted $C_{6-60}$ aryl, or a substituted or unsubstituted $C_{2-60}$ heteroaryl containing at least one of O and S.

2. The compound according to claim 1, wherein $L_1$ is a single bond, phenylene, biphenylylene, terphenylylene, quaterphenylylene, naphthylene, anthracenylene, fluorenylene, phenanthrenylene, pyrenylene, or triphenylenylene.

3. The compound according to claim 1, wherein $Ar_1$ and $Ar_2$ are each independently phenyl, biphenylyl, naphthyl, dibenzofuranyl, or dibenzothiophenyl.

4. The compound according to claim 1, wherein $Ar_1$ is a substituted or unsubstituted $C_{6-60}$ aryl.

5. The compound according to claim 1, wherein the compound is represented by any one of the following Chemical Formulas 1-1 to 1-3:

[Chemical Formula 1-1]

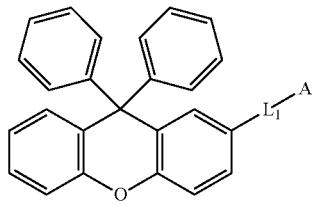

[Chemical Formula 1-2]

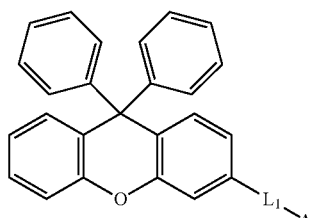

[Chemical Formula 1-3]

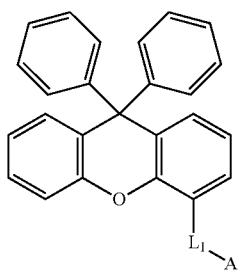

wherein in Chemical Formulas 1-1 to 1-3, $L_1$ and A are the same as defined in claim 1.

6. The compound according to claim 1, wherein the compound represented by Chemical Formula 1 is any one selected from the group consisting of the following:

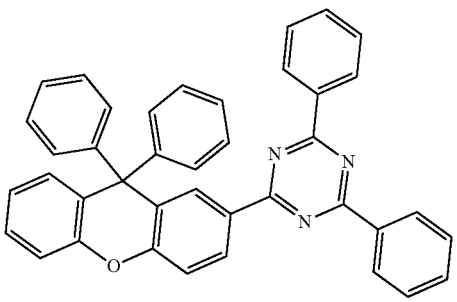

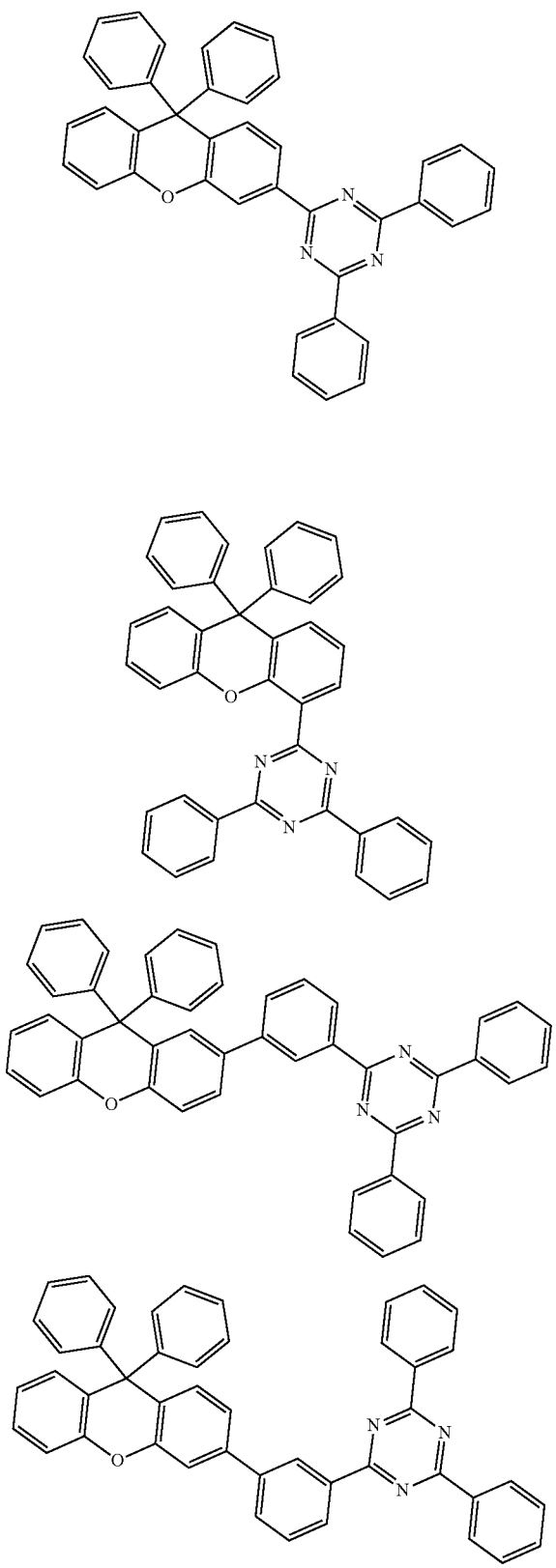
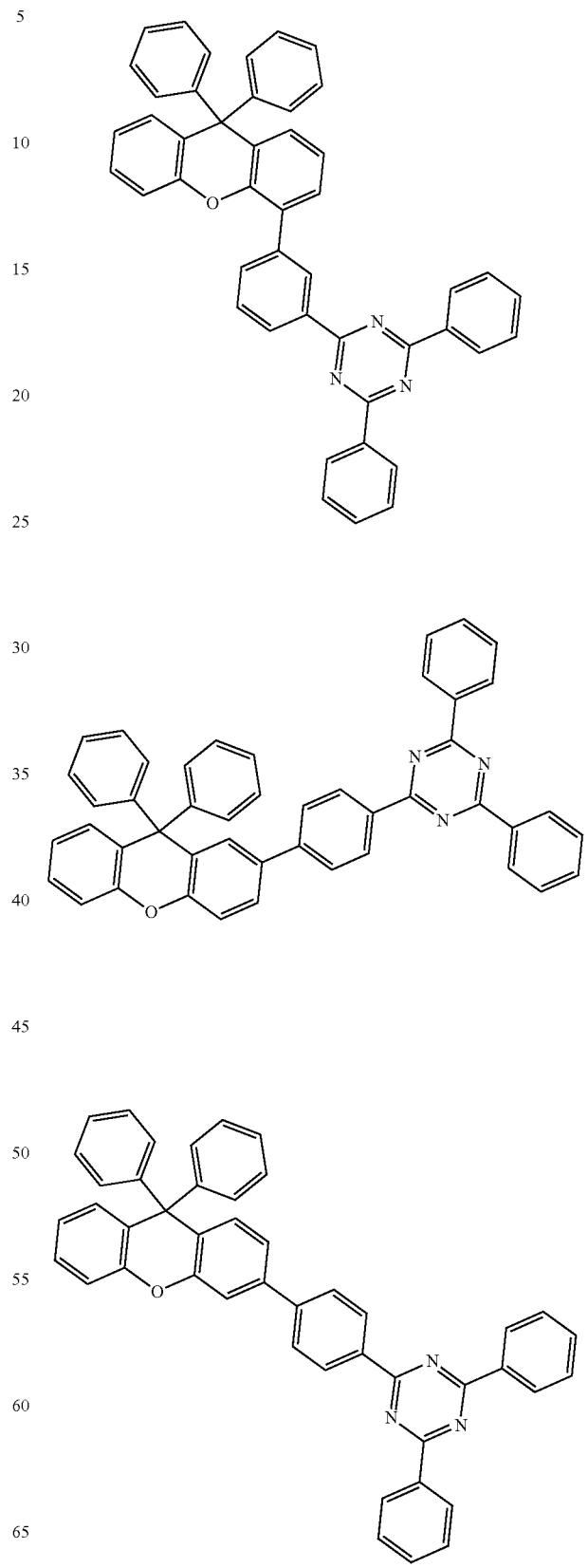

75
-continued
76
-continued
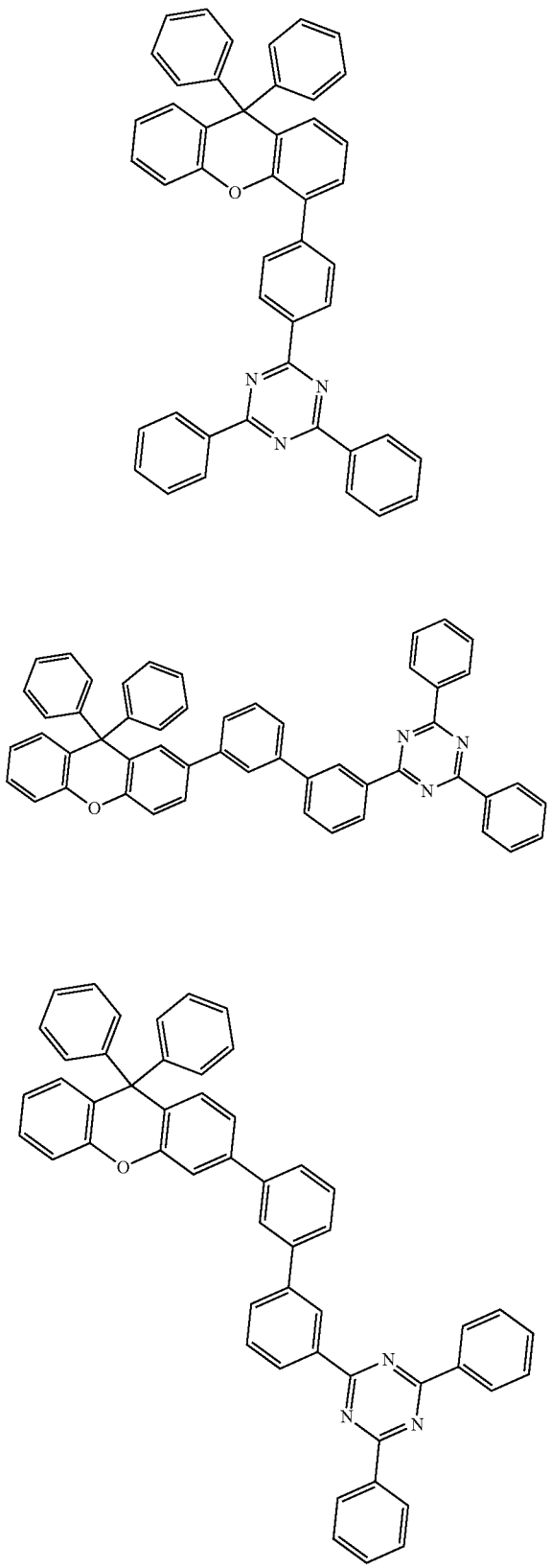
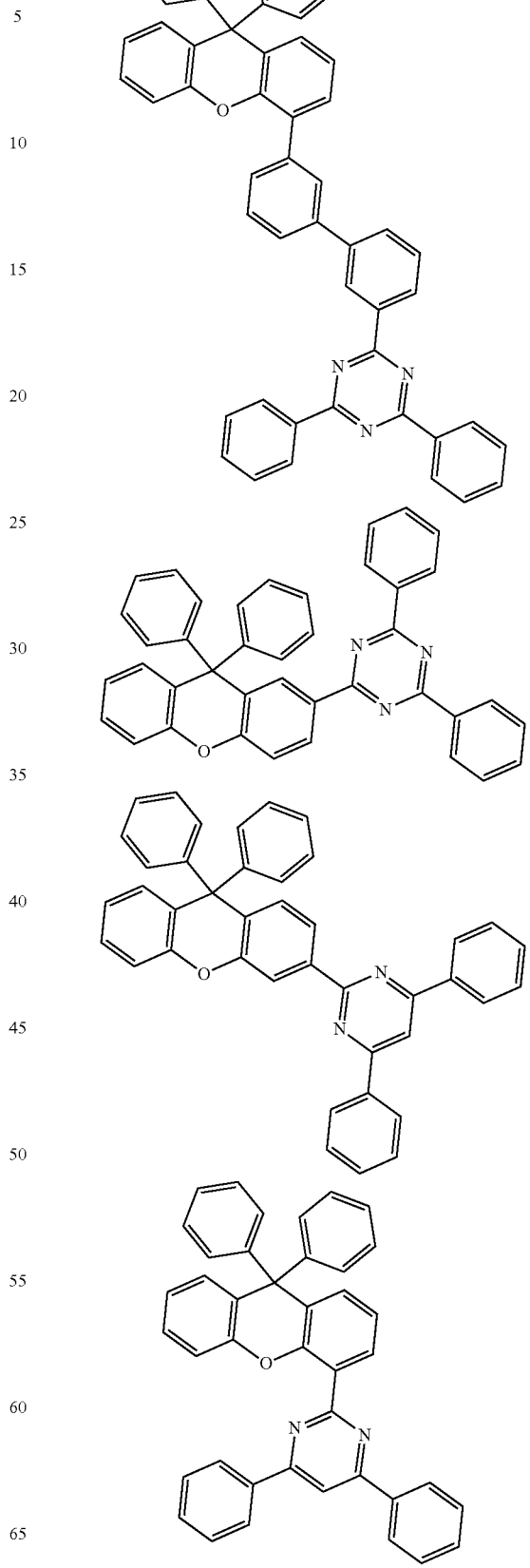

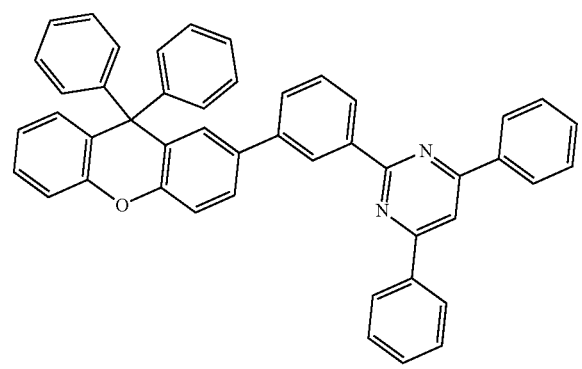
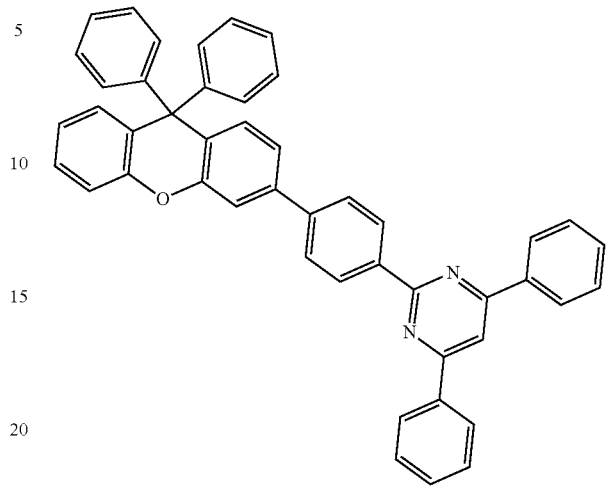
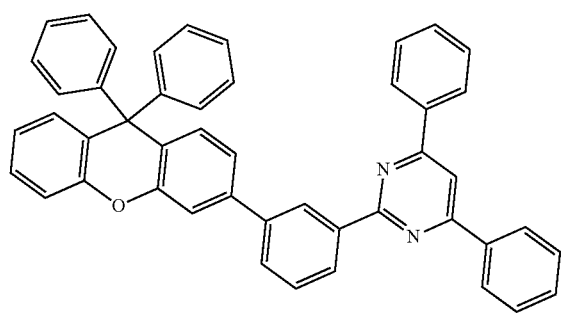
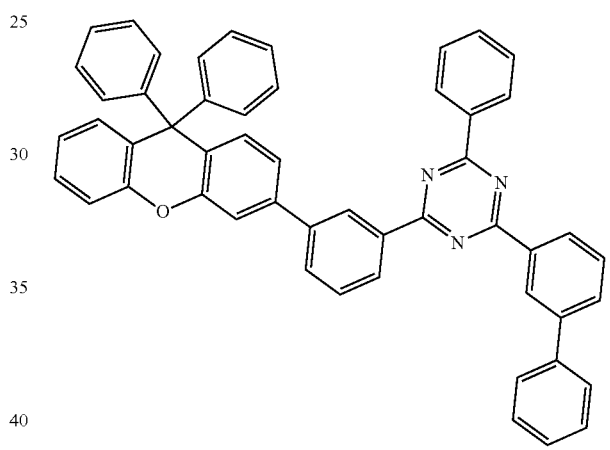
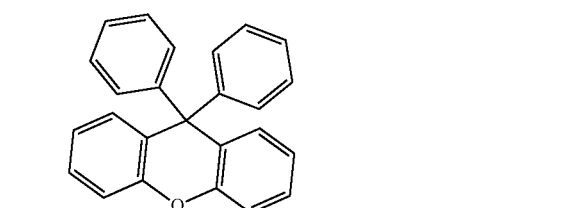
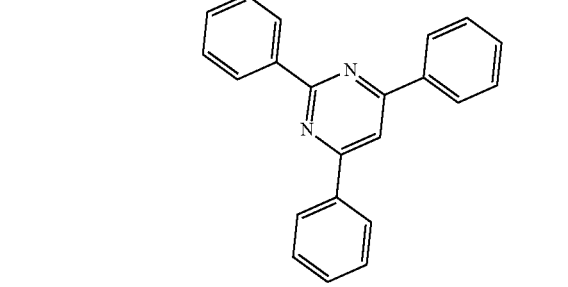
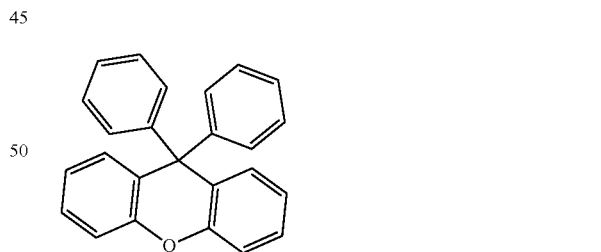
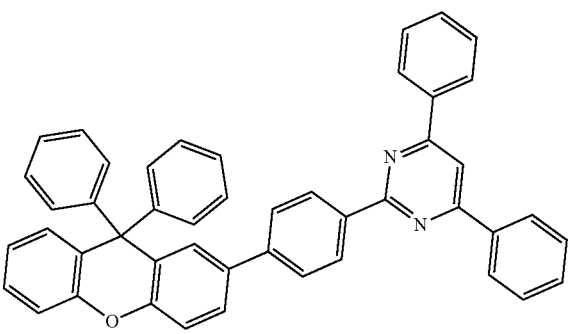
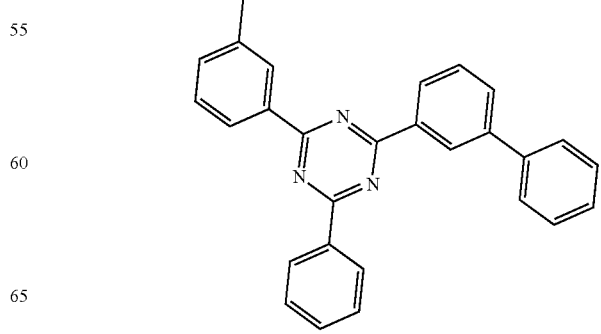

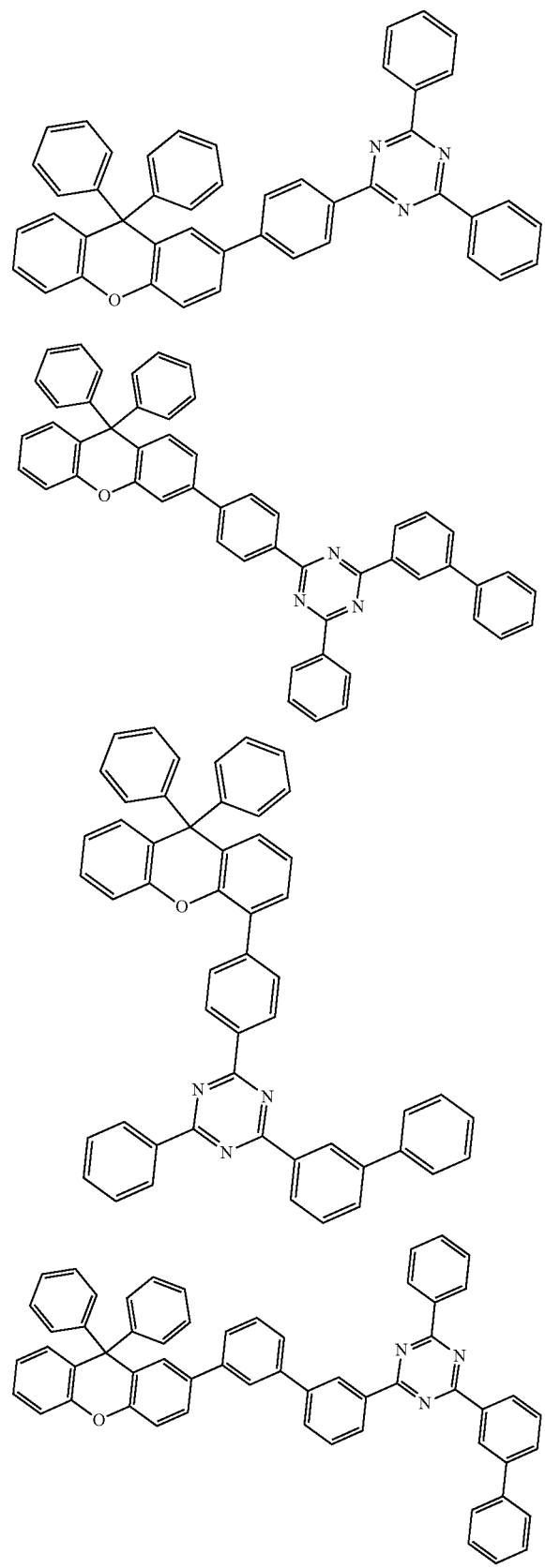
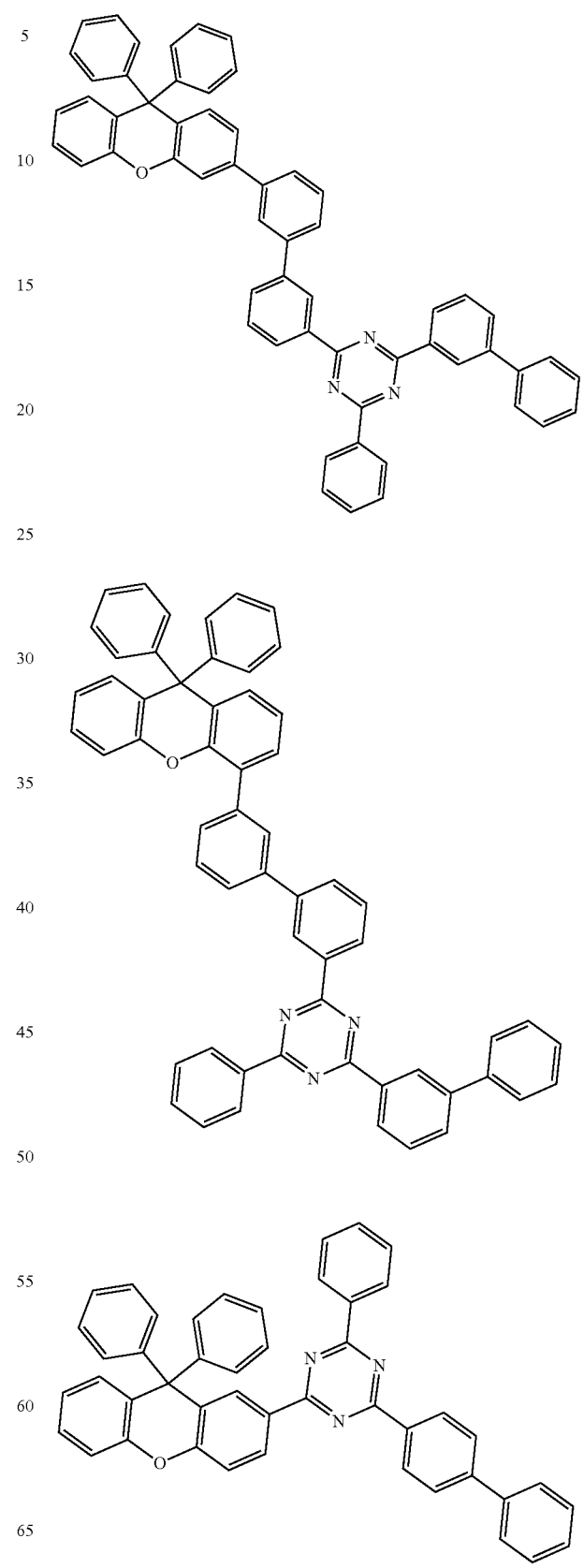

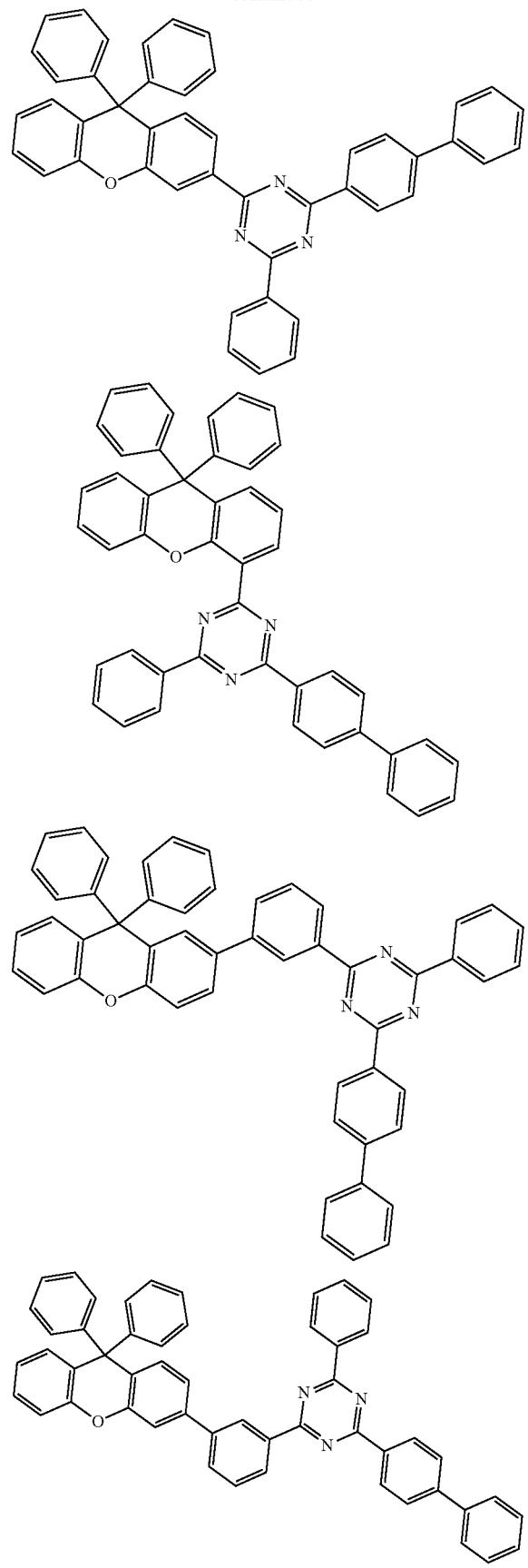
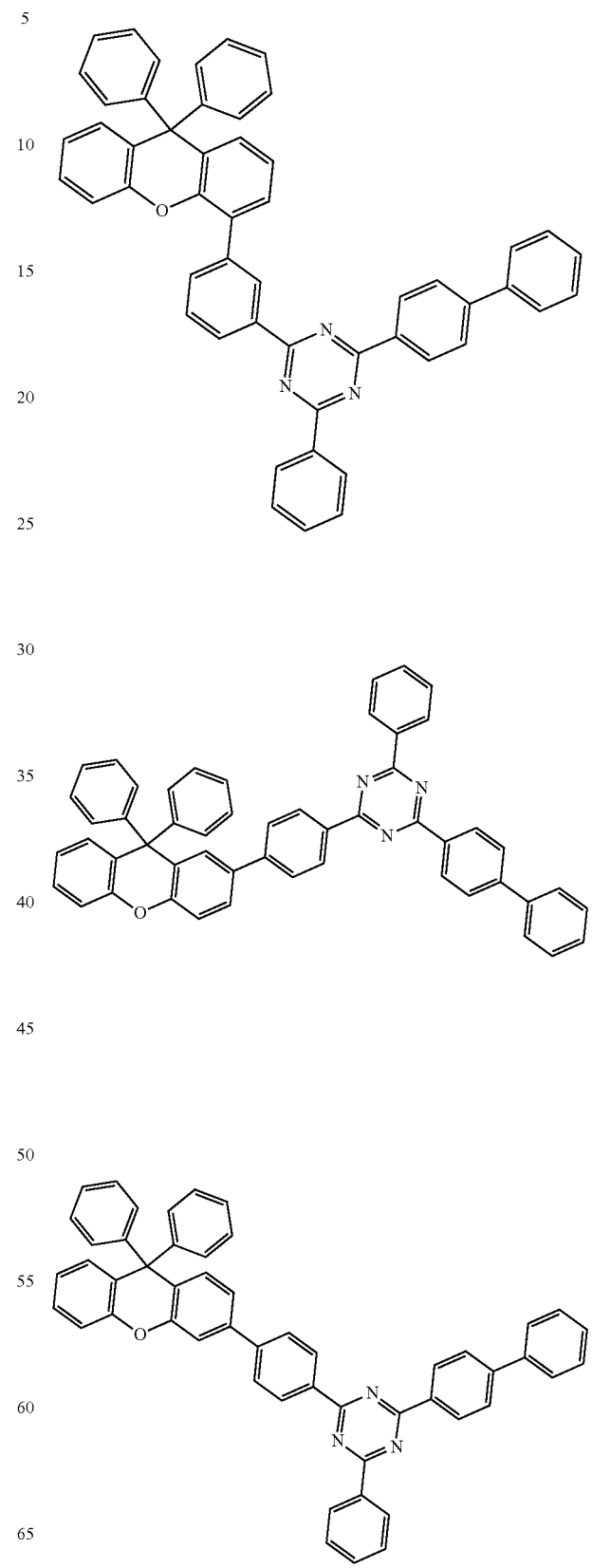

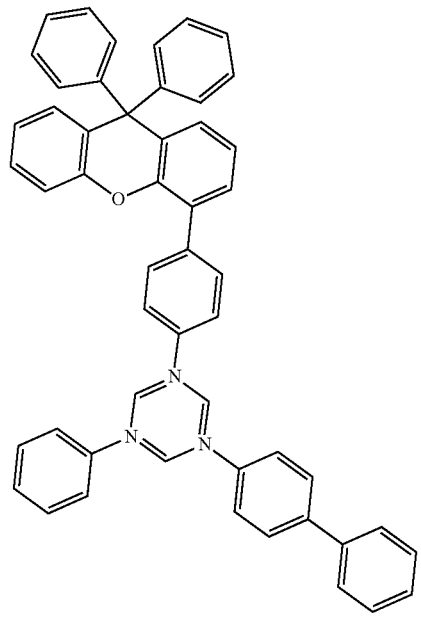
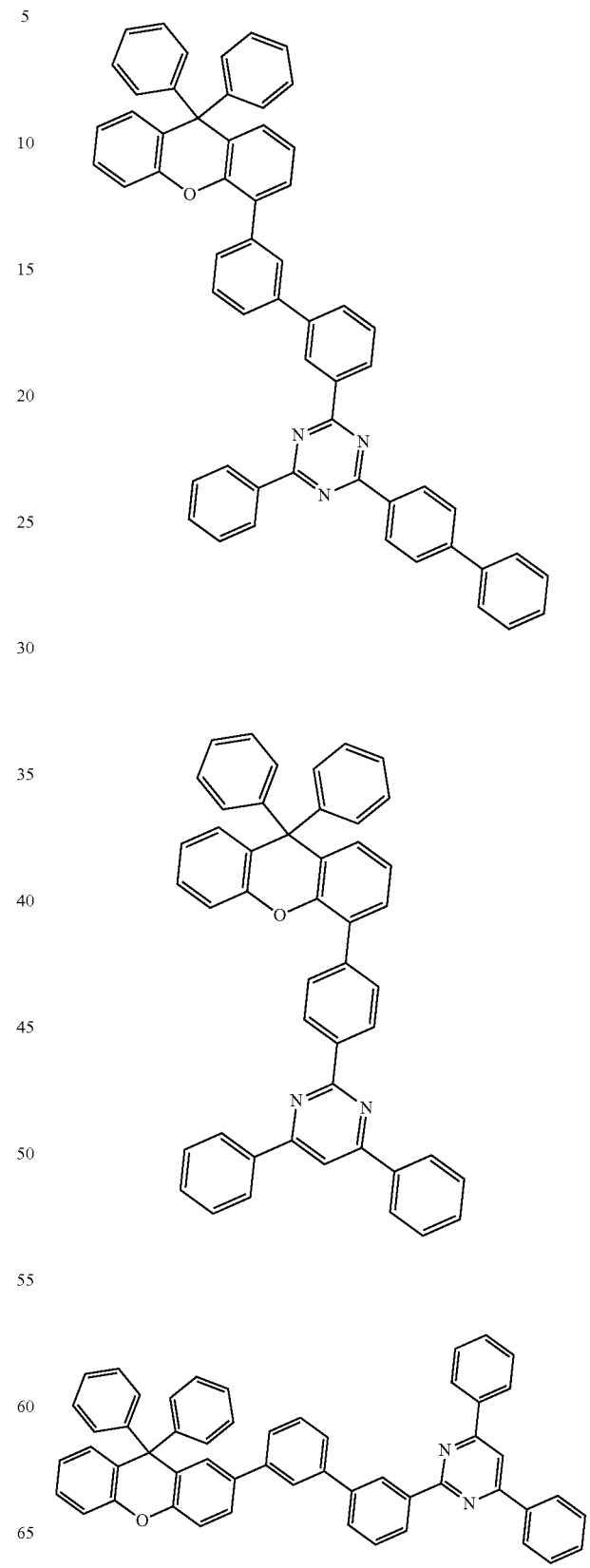

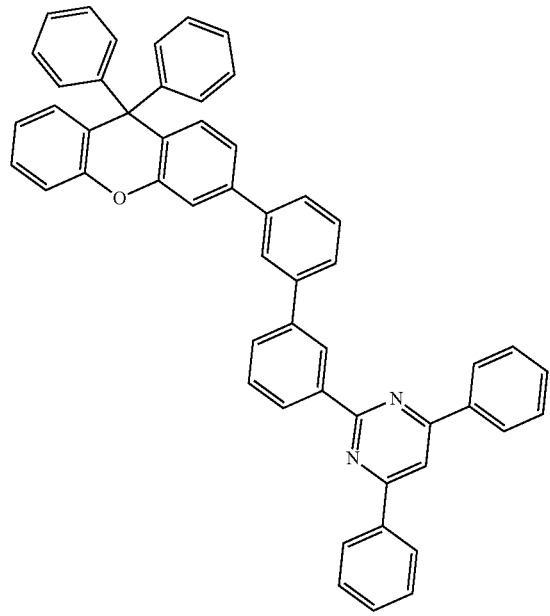
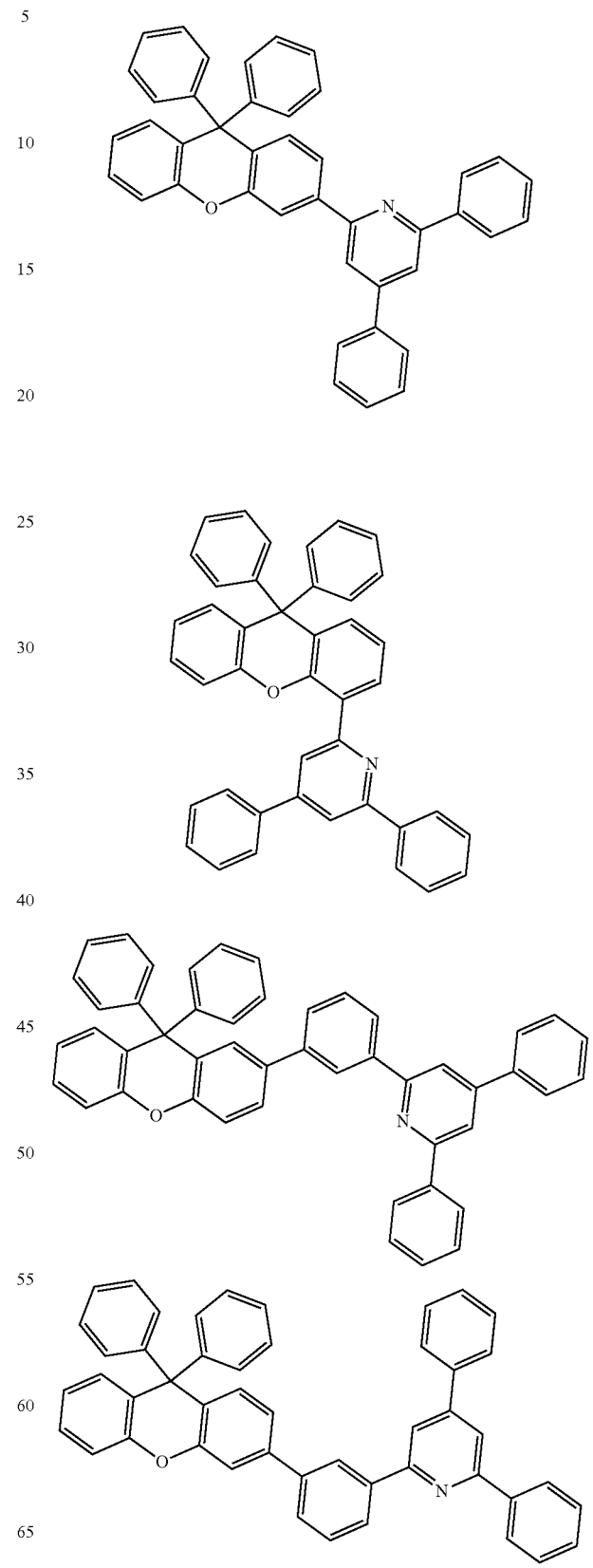

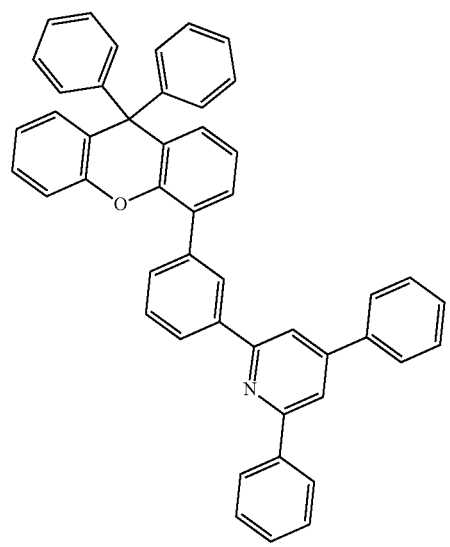
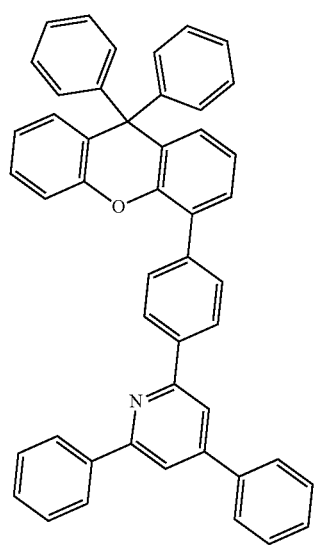 [SMILES: c1ccc(-c2nc(-c3ccccc3)nc(-c3ccc(-c4cccc5c4Oc4ccccc4C5(c4ccccc4)c4ccccc4)cc3)n2)cc1]
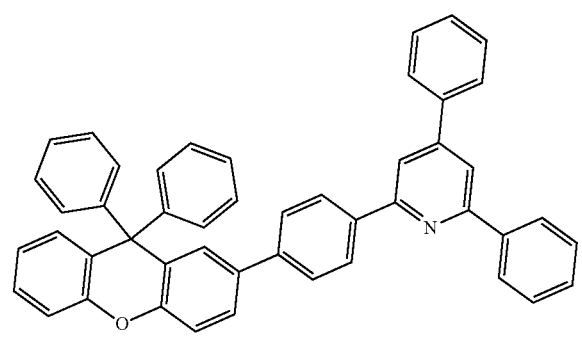
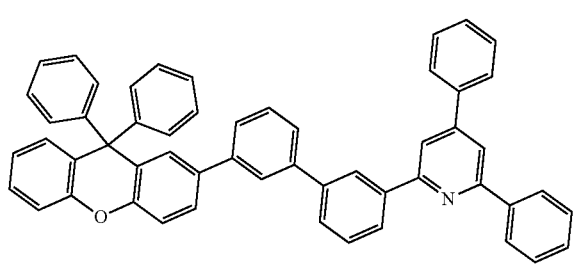
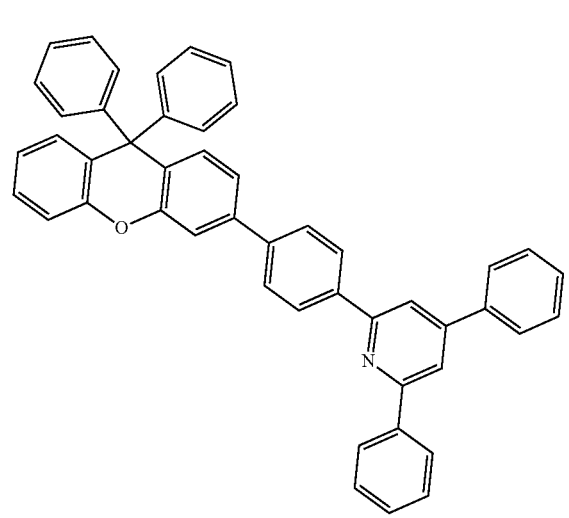
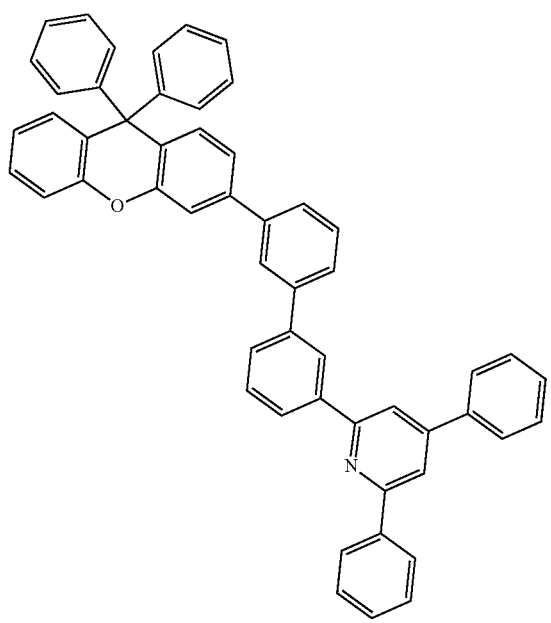

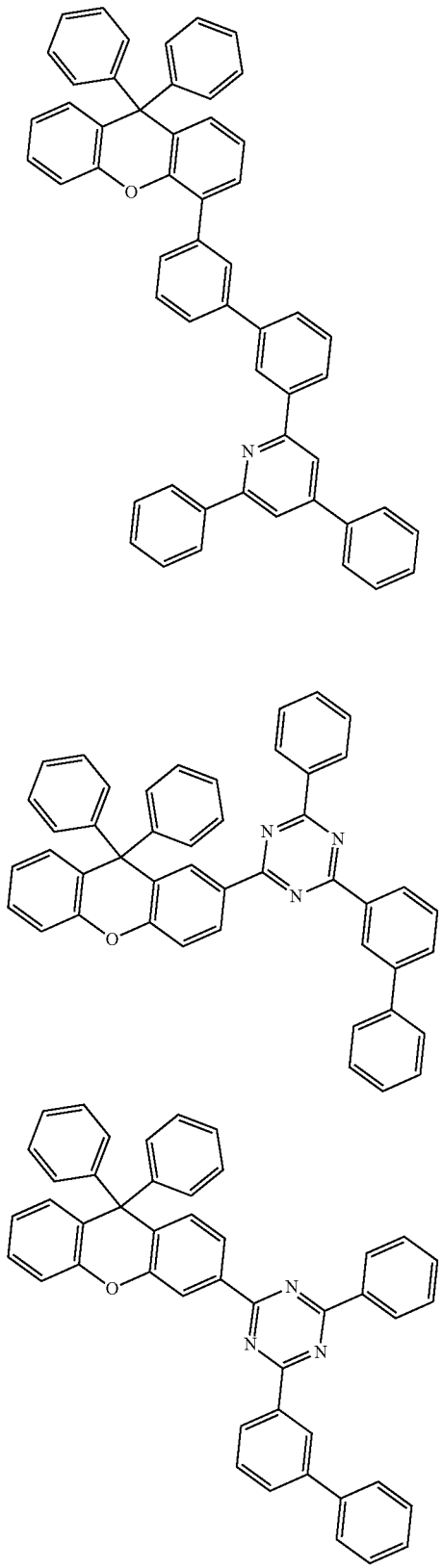
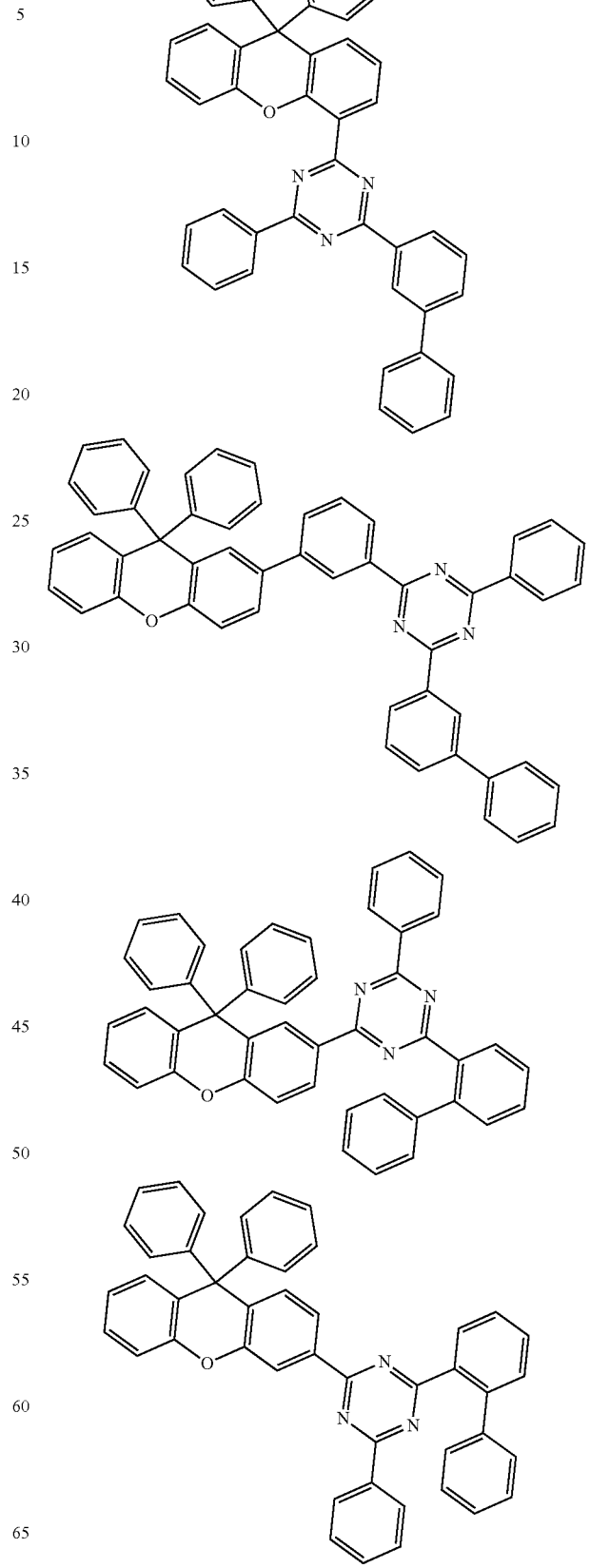

91
-continued
92
-continued
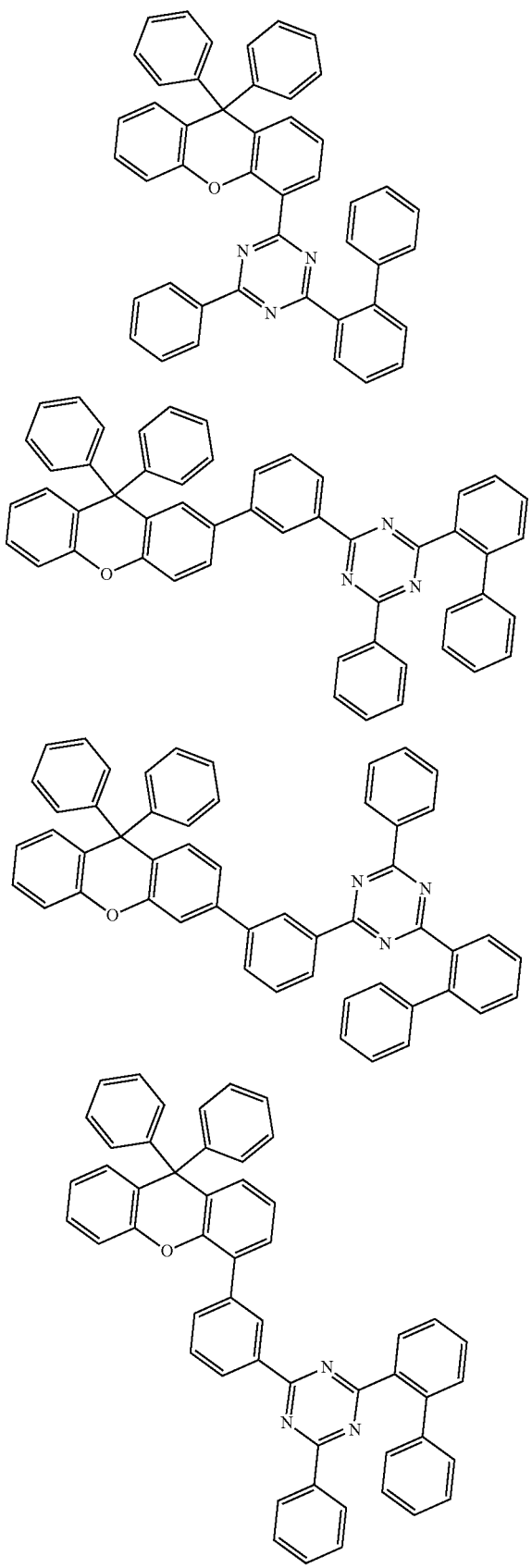
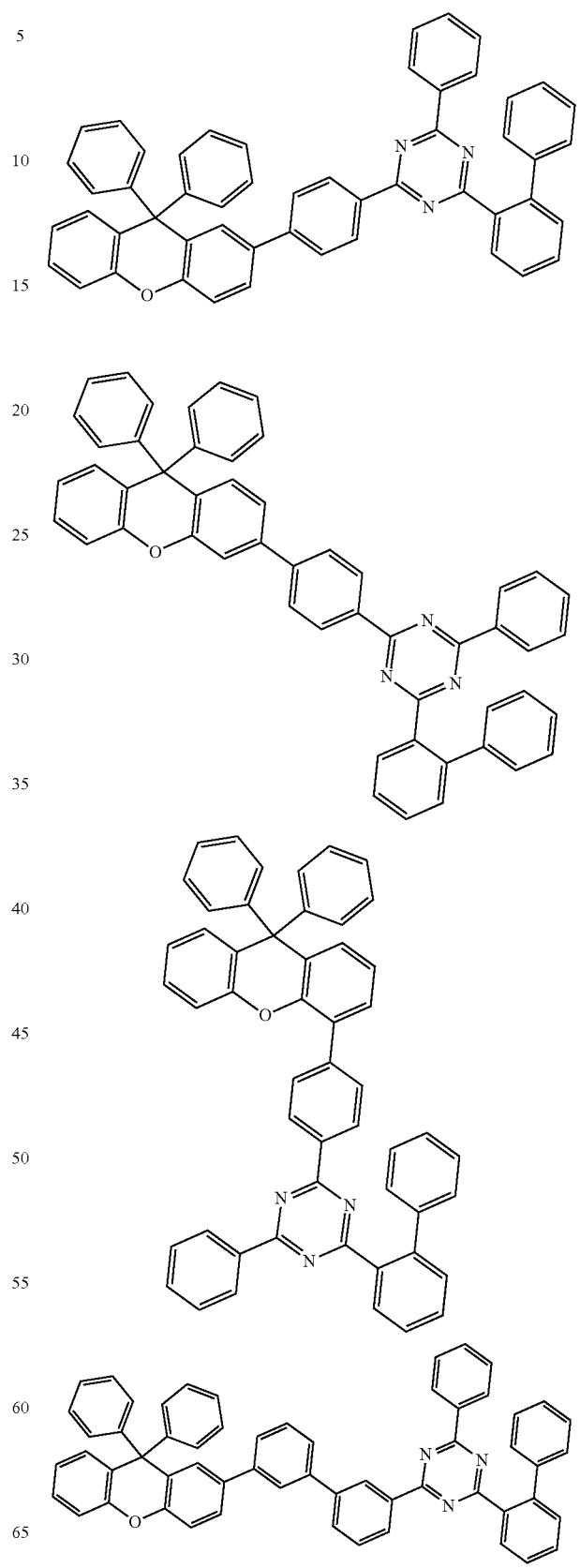

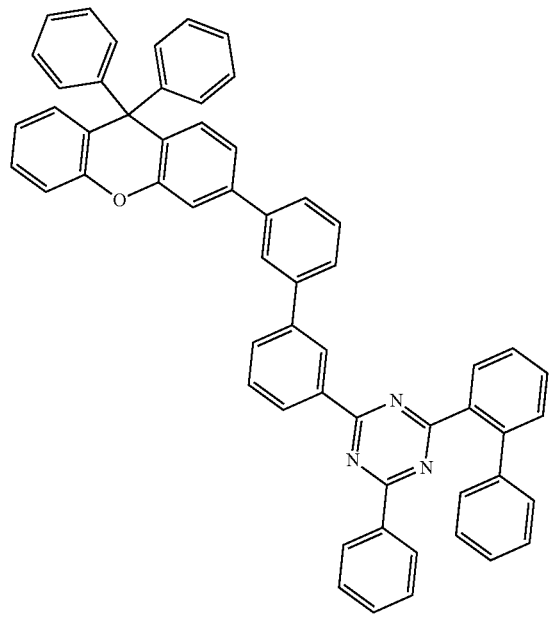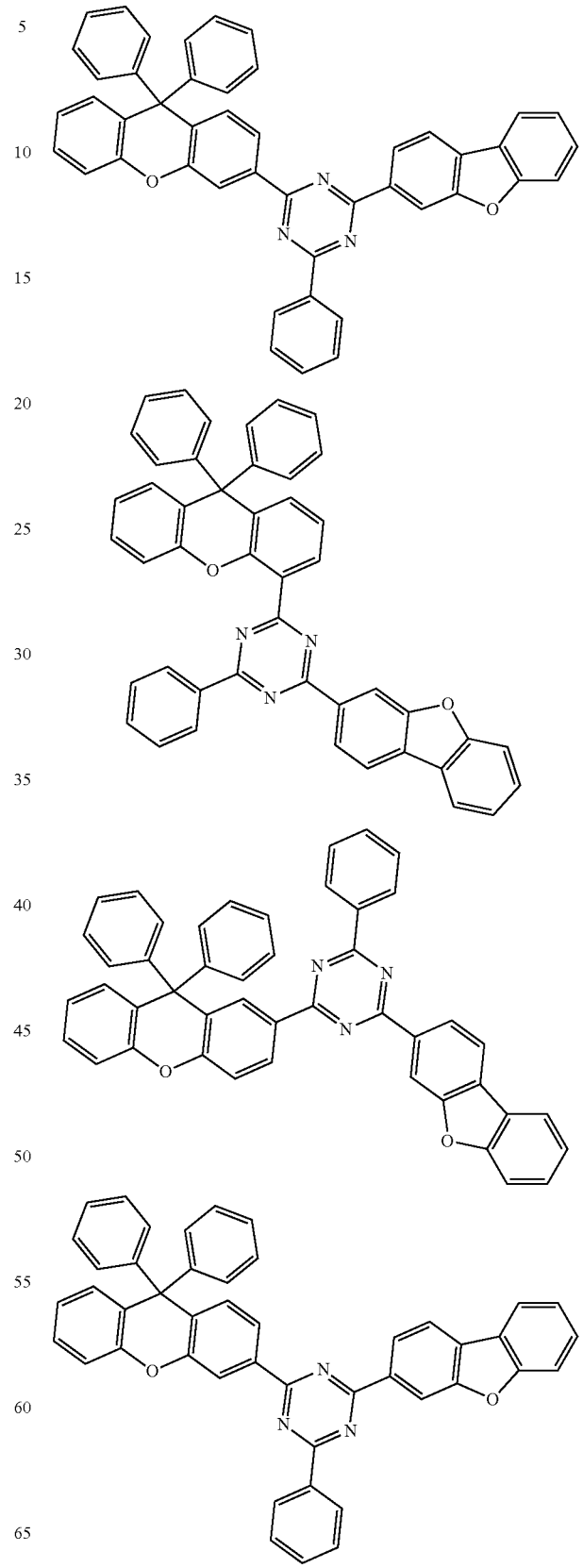

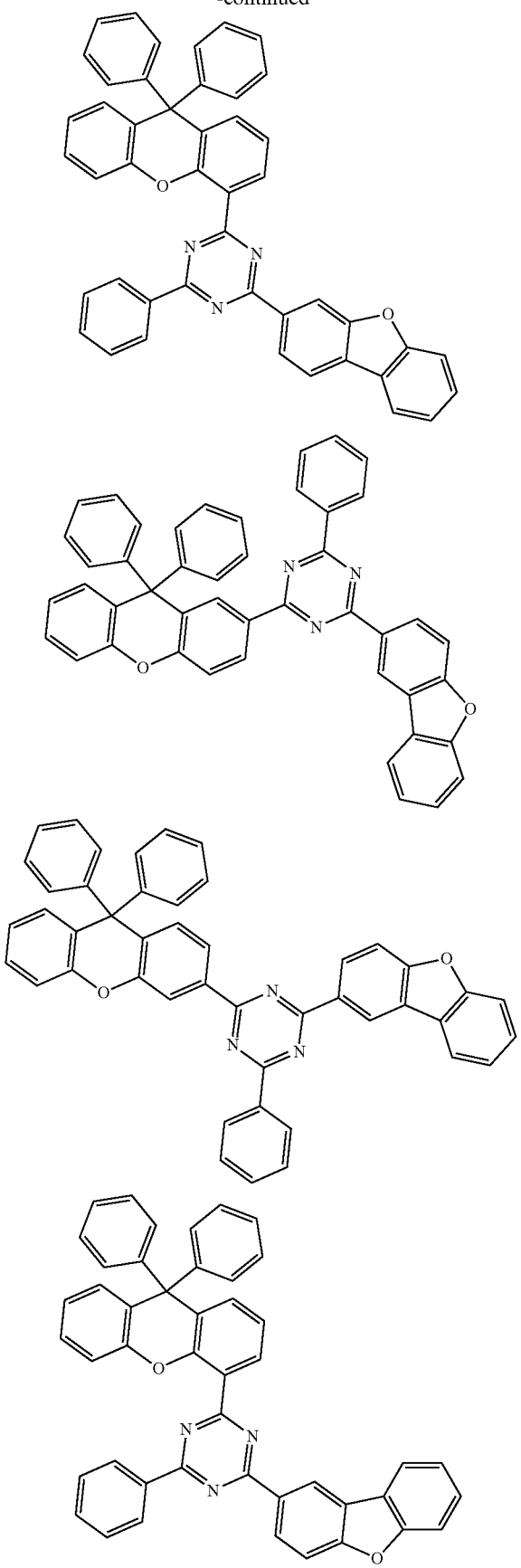
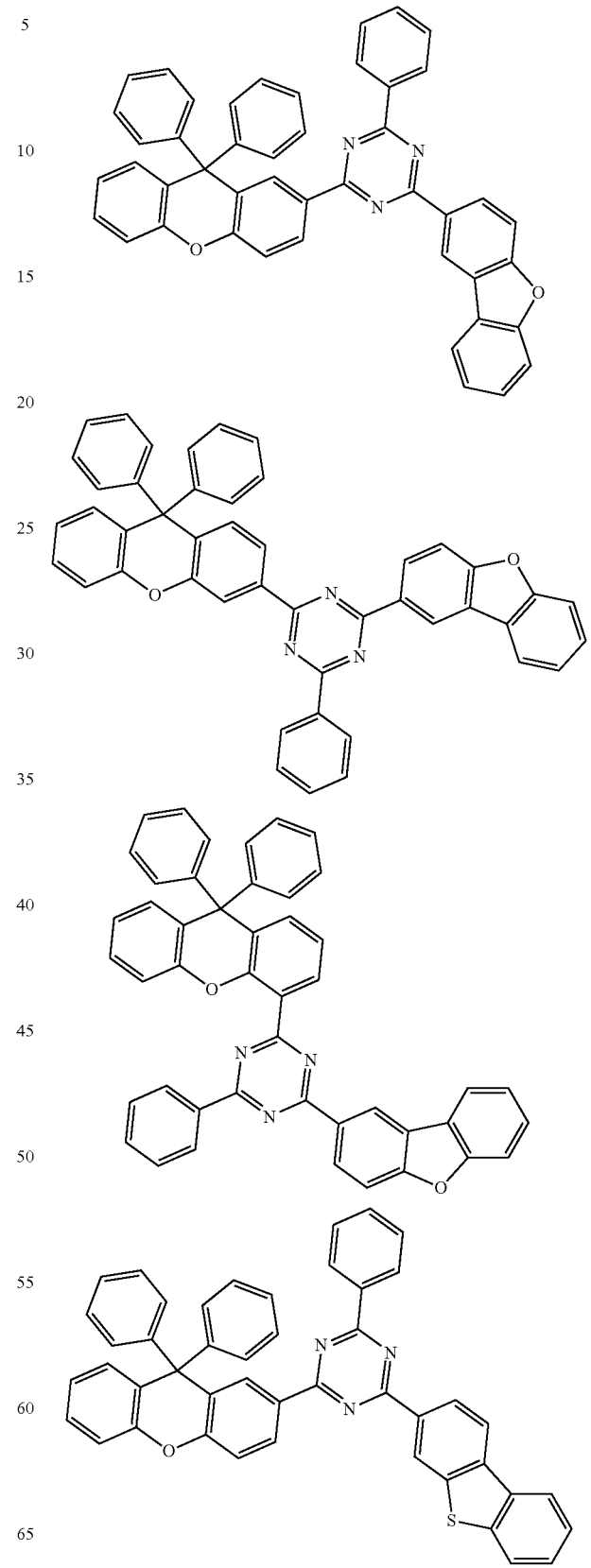

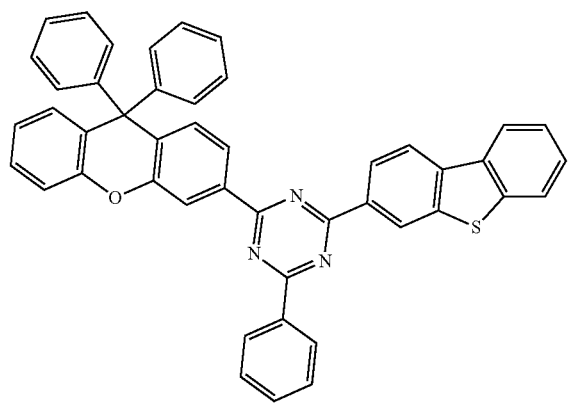
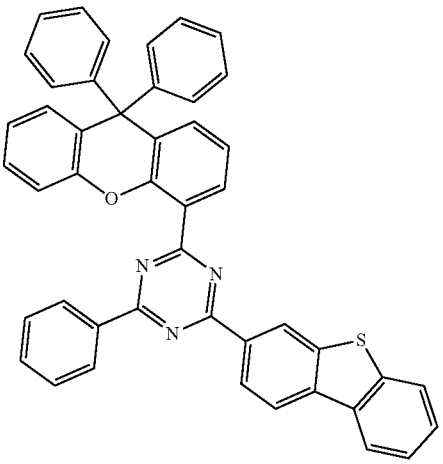

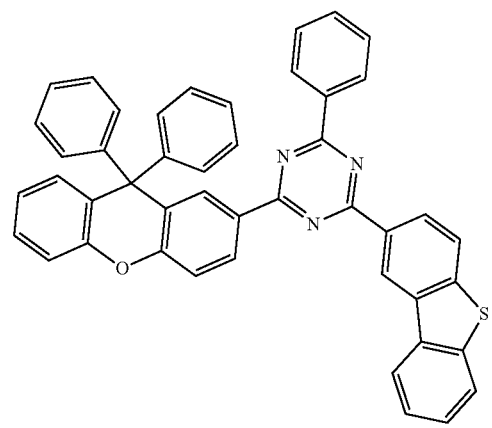
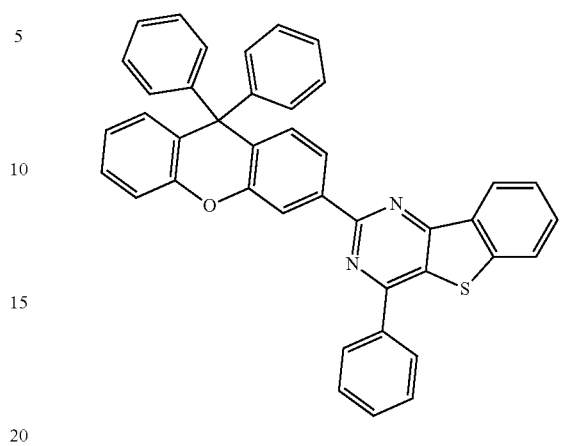
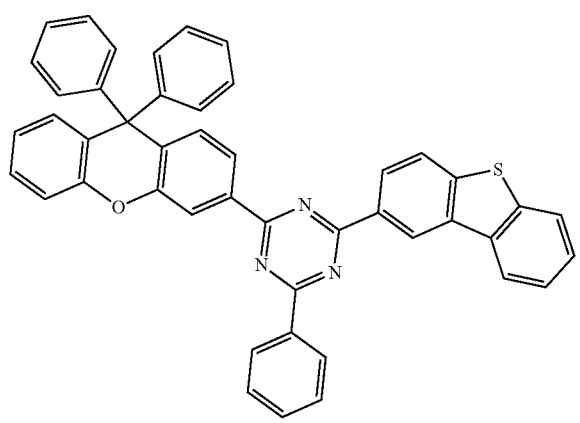
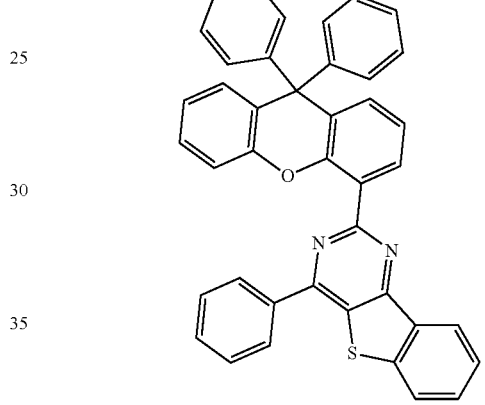
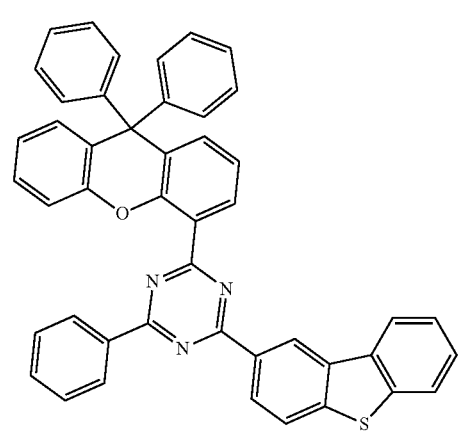
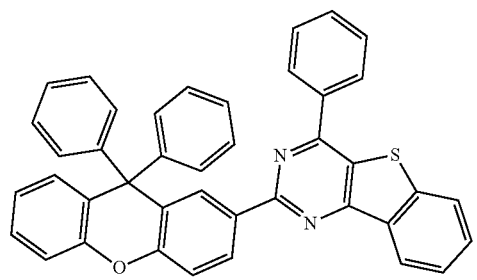
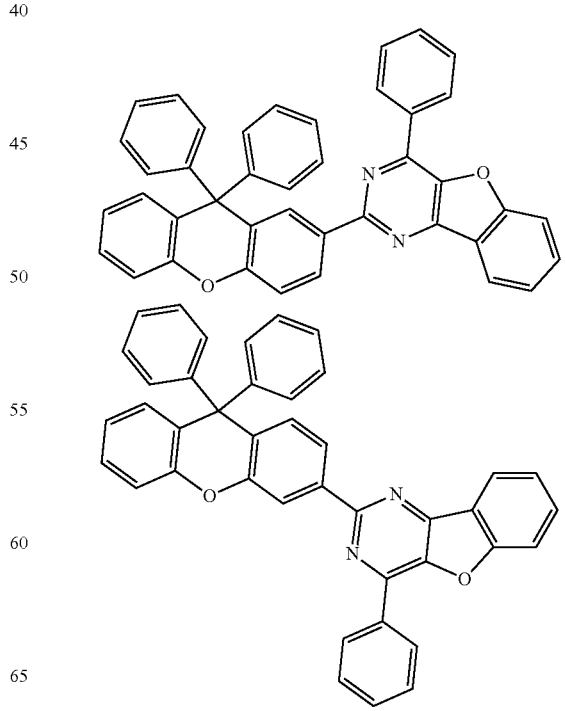

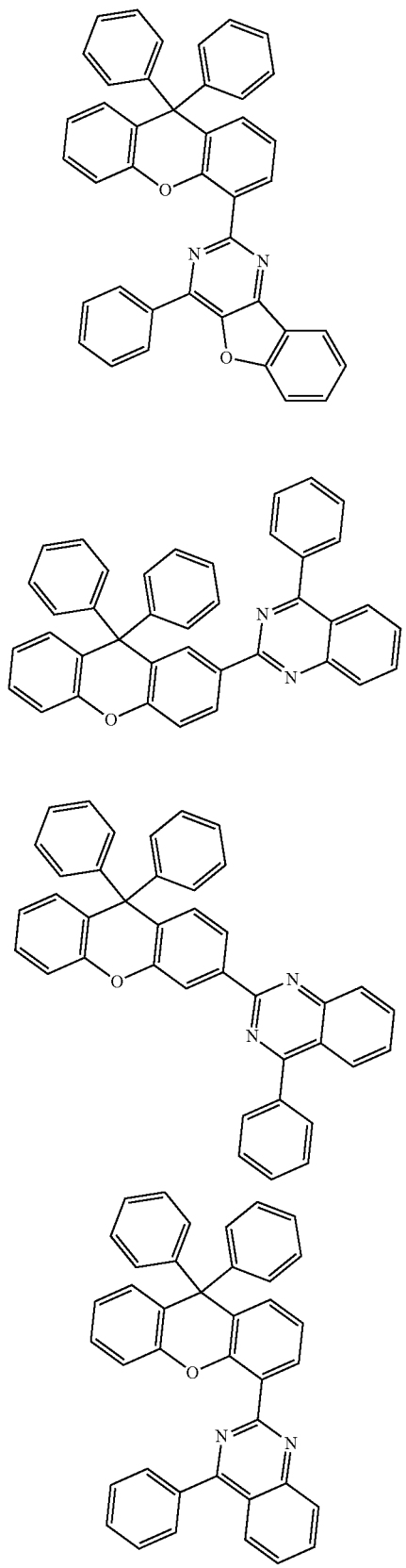
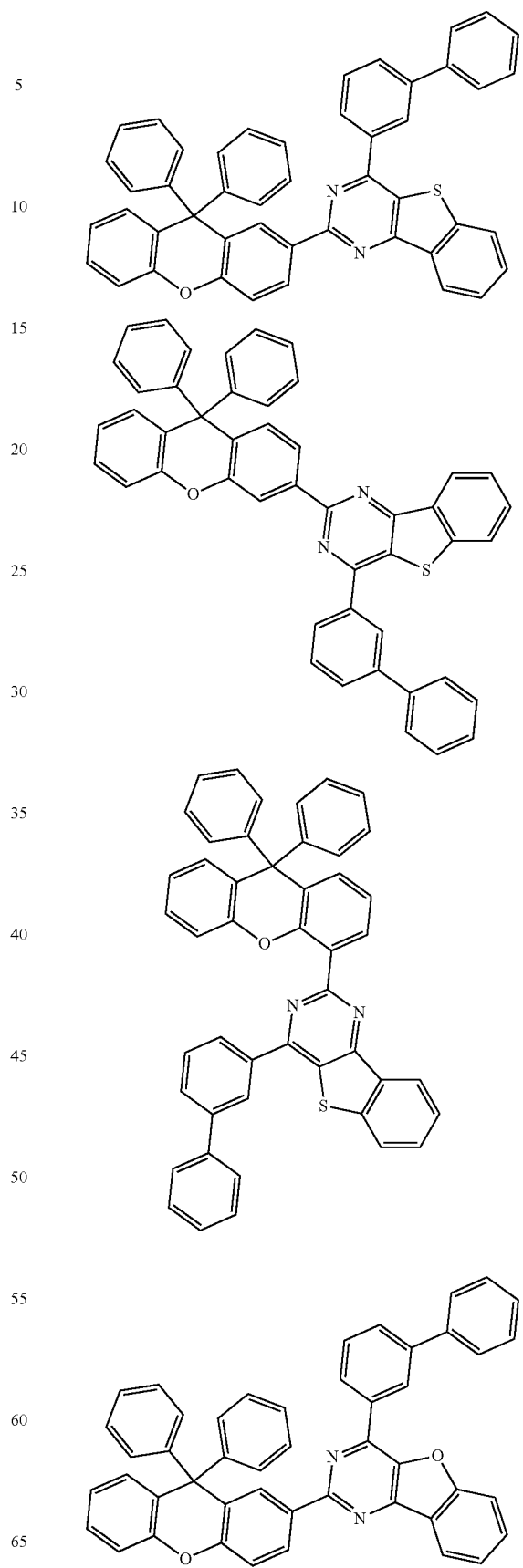

103
-continued
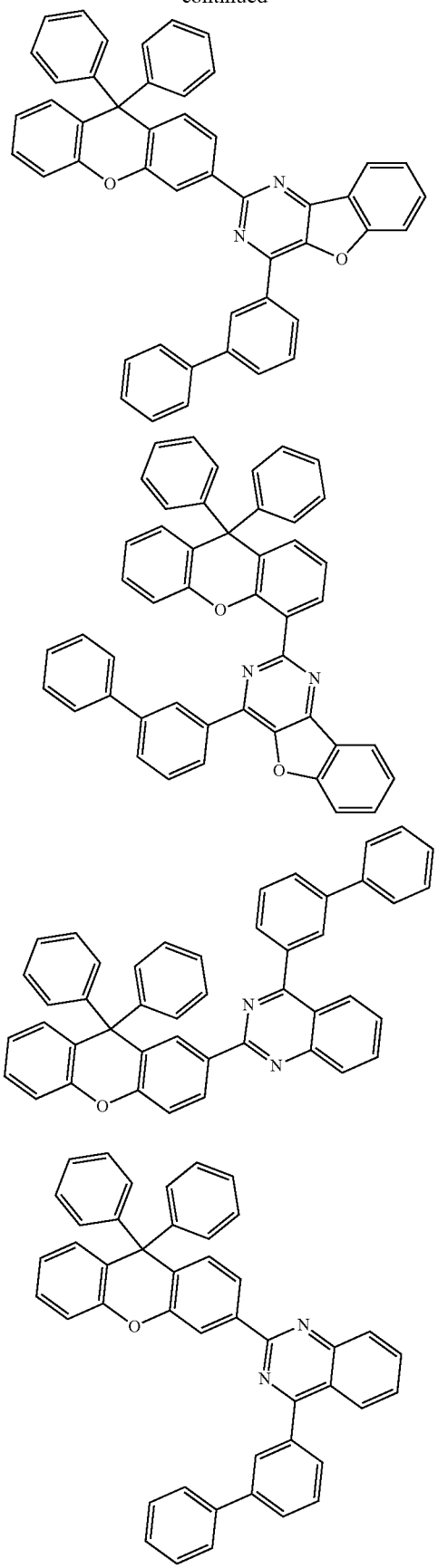
104
-continued
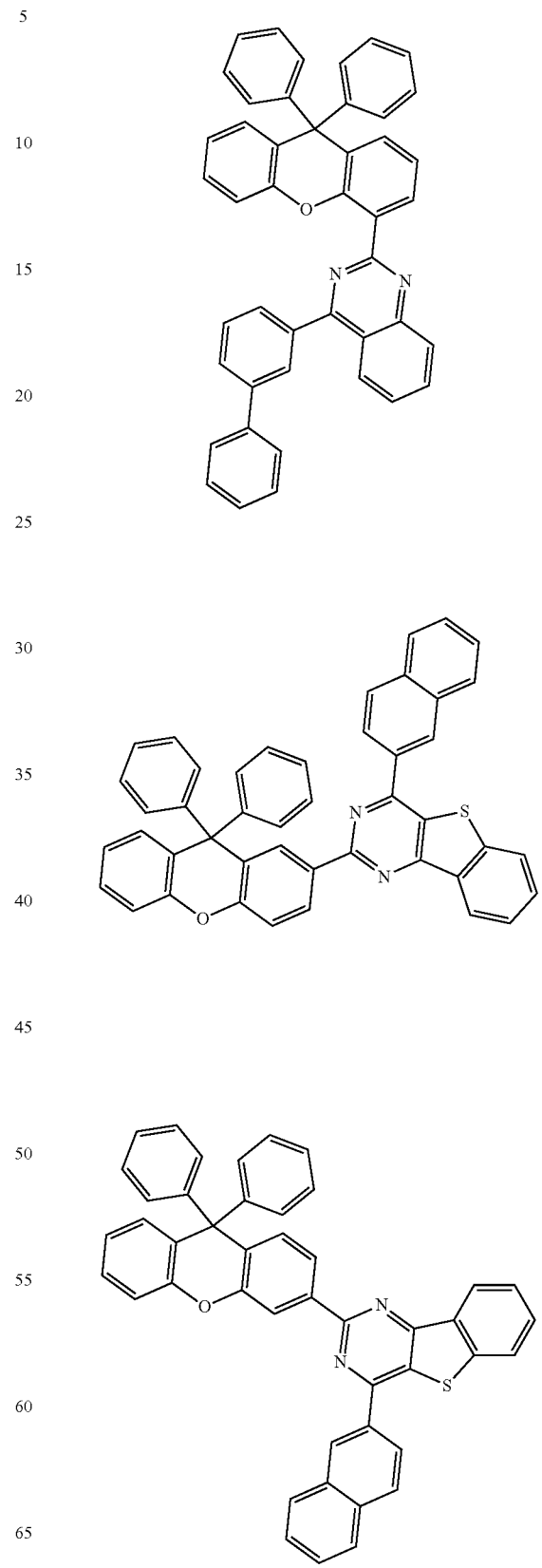

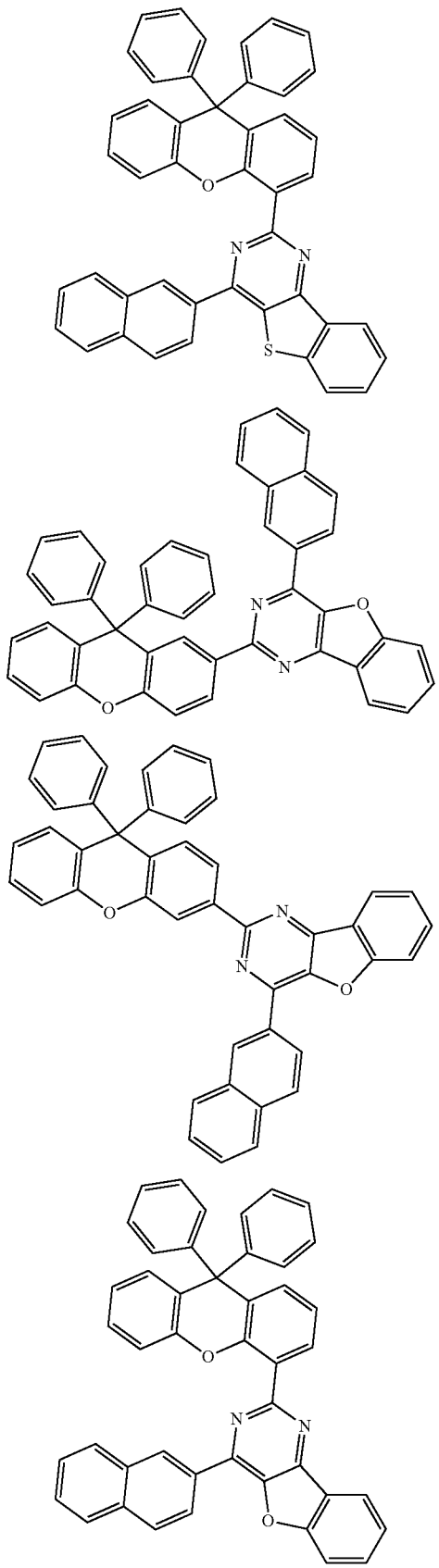
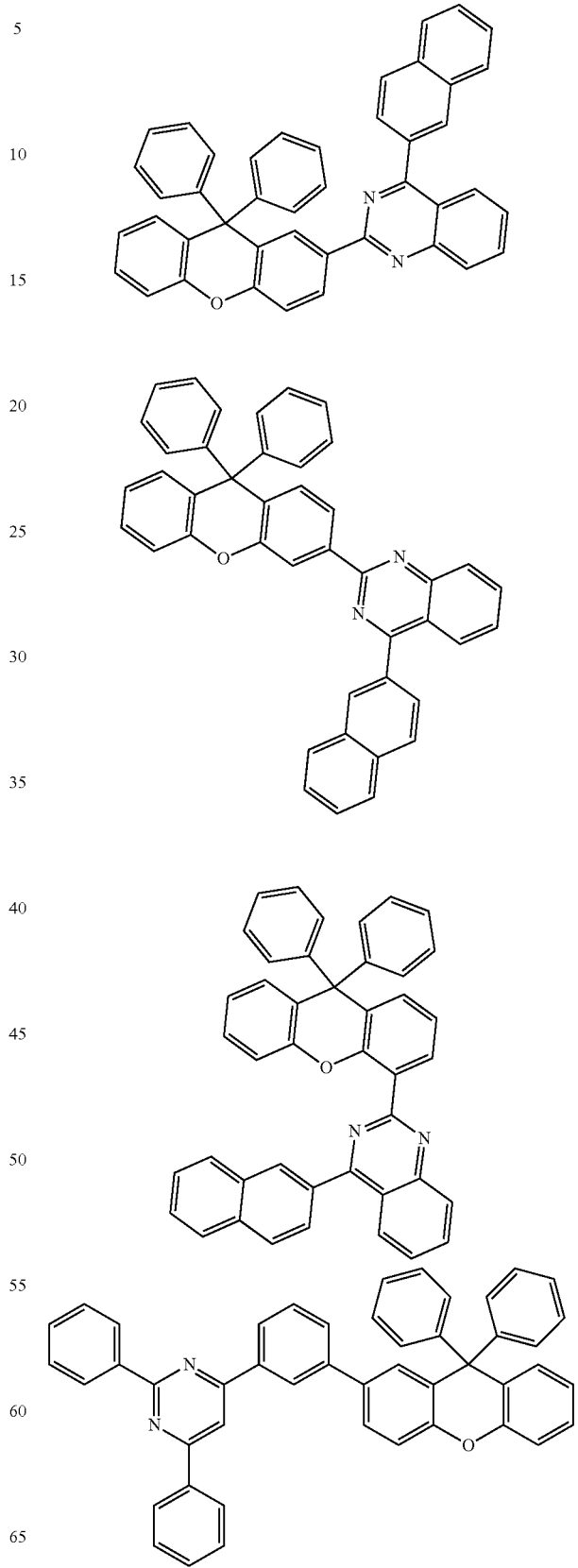

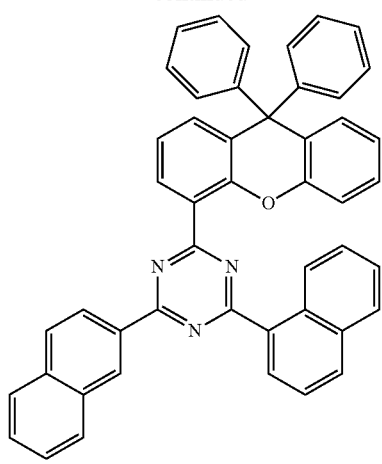
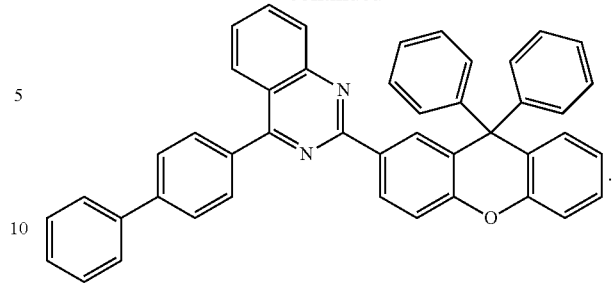
7. An organic light emitting device comprising: a first electrode; a second electrode provided to face the first electrode; and one or more organic material layers provided between the first electrode and the second electrode, wherein one or more layers of the organic material layers comprise the compound according to claim 1.
* * * * *

UNITED STATES PATENT AND TRADEMARK OFFICE
CERTIFICATE OF CORRECTION

Page 1 of 2

PATENT NO. : 11,926,607 B2
APPLICATION NO. : 16/981129
DATED : March 12, 2024
INVENTOR(S) : Cha et al.

It is certified that error appears in the above-identified patent and that said Letters Patent is hereby corrected as shown below:

In the Claims

In Claim 6, at Column 76, Lines 25-35, the compound should appear as follows:

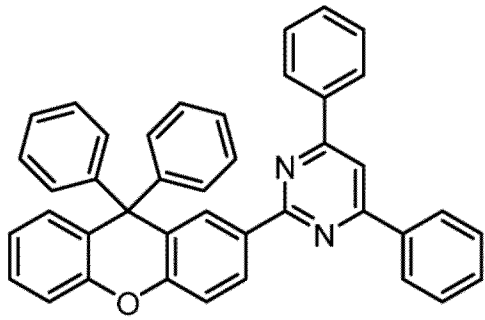

In Claim 6, at Column 79, Lines 4-16, the compound should appear as follows:

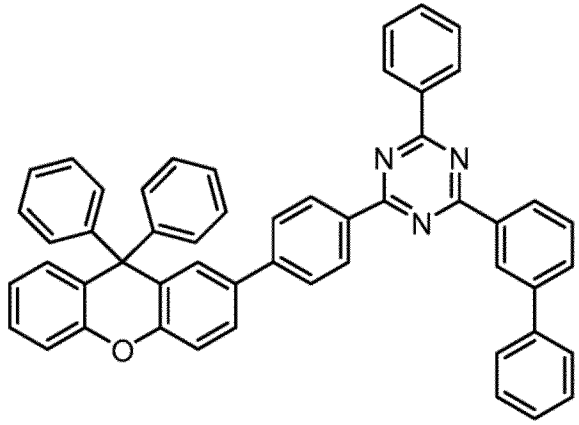

Signed and Sealed this
Fourteenth Day of May, 2024

Katherine Kelly Vidal
*Director of the United States Patent and Trademark Office*

CERTIFICATE OF CORRECTION (continued)
U.S. Pat. No. 11,926,607 B2

In Claim 6, at Column 83, Lines 46-66, the compound should appear as follows: